(12) United States Patent
Graupe et al.

(10) Patent No.: US 8,258,316 B2
(45) Date of Patent: Sep. 4, 2012

(54) ALKANOYLAMINO BENZAMIDE ANILINE HDAC INHIBITOR COMPOUNDS

(75) Inventors: Michael Graupe, Pacifica, CA (US); Chandrasekar Venkataramani, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 82 days.

(21) Appl. No.: 12/795,554

(22) Filed: Jun. 7, 2010

(65) Prior Publication Data
US 2010/0310500 A1 Dec. 9, 2010

Related U.S. Application Data

(60) Provisional application No. 61/185,126, filed on Jun. 8, 2009.

(51) Int. Cl.
C07D 207/08 (2006.01)
A61K 31/4025 (2006.01)
(52) U.S. Cl. .......................... 548/568; 514/428
(58) Field of Classification Search .................. 548/568; 514/428
See application file for complete search history.

(56) References Cited

U.S. PATENT DOCUMENTS

| | | | |
|---|---|---|---|
| 5,760,246 | A | 6/1998 | Biller et al. |
| 6,403,588 | B1 | 6/2002 | Hayakawa et al. |
| 7,253,204 | B2 | 8/2007 | Delorme et al. |
| 2002/0168761 | A1 | 11/2002 | Gour et al. |
| 2004/0006011 | A1 | 1/2004 | Gour et al. |
| 2005/0054850 | A1 | 3/2005 | Wu et al. |
| 2005/0187266 | A1 | 8/2005 | Su |
| 2005/0234066 | A1 | 10/2005 | Bailey et al. |
| 2005/0288282 | A1 | 12/2005 | Delorme et al. |
| 2006/0293320 | A1 | 12/2006 | Schmitz et al. |
| 2007/0093492 | A1 | 4/2007 | Jiaang et al. |
| 2007/0213330 | A1 | 9/2007 | Delorme et al. |
| 2009/0005374 | A1 | 1/2009 | Melvin, Jr. et al. |
| 2009/0076021 | A1 | 3/2009 | Plato |
| 2010/0009990 | A1 | 1/2010 | Venkataramani |
| 2010/0022543 | A1 | 1/2010 | Melvin, Jr. et al. |
| 2010/0029638 | A1 | 2/2010 | Melvin, Jr. et al. |
| 2010/0310500 | A1 | 12/2010 | Graupe et al. |
| 2010/0311794 | A1 | 12/2010 | Venkataramani |

FOREIGN PATENT DOCUMENTS

| | | |
|---|---|---|
| CA | 2644933 A1 | 9/2007 |
| EP | 0847992 A1 | 6/1998 |
| EP | 1277754 A1 | 1/2003 |
| JP | 2003-313126 A | 11/2003 |
| JP | 2004-002826 A | 1/2004 |
| JP | 2007-001885 A | 1/2007 |
| WO | WO-97/26240 A1 | 7/1997 |
| WO | WO-00/18733 A1 | 4/2000 |
| WO | WO-01/14375 A1 | 3/2001 |
| WO | WO-01/19788 A2 | 3/2001 |
| WO | WO-01/53331 A2 | 7/2001 |
| WO | WO-01/56989 A2 | 8/2001 |
| WO | WO-01/83481 A1 | 11/2001 |
| WO | WO-02/00651 A2 | 1/2002 |
| WO | WO-02/26712 A2 | 4/2002 |
| WO | WO-02/34748 A1 | 5/2002 |
| WO | WO-02/46170 A2 | 6/2002 |
| WO | WO-02/065979 A2 | 8/2002 |
| WO | WO-02/066480 A2 | 8/2002 |
| WO | WO-02/066481 A1 | 8/2002 |
| WO | WO-03/000682 A1 | 1/2003 |
| WO | WO-03/000689 A1 | 1/2003 |
| WO | WO-03/002524 A2 | 1/2003 |
| WO | WO-03/031446 A1 | 4/2003 |
| WO | WO-03/041649 A2 | 5/2003 |
| WO | WO-03/084948 A1 | 10/2003 |
| WO | WO-03/084997 A1 | 10/2003 |
| WO | WO-03/099221 A2 | 12/2003 |
| WO | WO-03/099817 A1 | 12/2003 |
| WO | WO-03/103151 A1 | 12/2003 |
| WO | WO-2004/021989 A2 | 3/2004 |
| WO | WO-2004/035525 A1 | 4/2004 |
| WO | WO-2004/039325 A2 | 5/2004 |
| WO | WO-2004/041191 A2 | 5/2004 |
| WO | WO-2004/048343 A1 | 6/2004 |
| WO | WO-2004/060318 A2 | 7/2004 |
| WO | WO-2004/069133 A2 | 8/2004 |

(Continued)

OTHER PUBLICATIONS

Kubinyi (3D QSAR in Drug Design: Ligand-Protein Interactions and Molecular Similarity, vol. 2-3, Springer, 1998, 800 pages). TOC and pp. 243-244 provided.*
Methot et al. (Bioorg. Med. Chem. Lett. 18 (2008) 973-978).*
Wermuth, The Practice of Medicinal Chemsitry, 2d ed. (2003), 768 pages. Chapters 9-10 provided.*
Tsatsas et al. (CAPLUS Abstract of: Bulletin de la Societe Chimique de France (1962) 732-3).*
Arbiser, J.L. (2007) "Why Targeted Therapy Hasn't Worked in Advanced Cancer", *The Journal of Clinical Investigation*, vol. 17, No. 10 pp. 2762-2765.
Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.

(Continued)

*Primary Examiner* — Robert Havlin
(74) *Attorney, Agent, or Firm* — J. Elin Hartrum

(57) ABSTRACT

The present invention provides a compound of general Formula (I) having histone deacetylase (HDAC) inhibitory activity, a pharmaceutical composition comprising the compound, and a method useful to treat diseases using the compound.

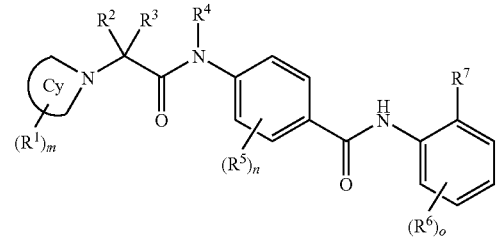

Formula (I)

17 Claims, No Drawings

FOREIGN PATENT DOCUMENTS

| | | |
|---|---|---|
| WO | WO-2004/069803 A2 | 8/2004 |
| WO | WO-2004/076452 A1 | 9/2004 |
| WO | WO-2004/080390 A2 | 9/2004 |
| WO | WO-2004/084901 A1 | 10/2004 |
| WO | WO-2004/092115 A2 | 10/2004 |
| WO | WO-2004/092145 A1 | 10/2004 |
| WO | WO-2004/110350 A2 | 12/2004 |
| WO | WO-2005/006945 A2 | 1/2005 |
| WO | WO-2005/030140 A2 | 4/2005 |
| WO | WO-2005-030705 A1 | 4/2005 |
| WO | WO-2005/046594 A2 | 5/2005 |
| WO | WO-2005/054850 A2 | 6/2005 |
| WO | WO-2005/060571 A2 | 7/2005 |
| WO | WO-2005/070180 A2 | 8/2005 |
| WO | WO-2005/077368 A2 | 8/2005 |
| WO | WO-2005/077373 A2 | 8/2005 |
| WO | WO-2005/082871 A2 | 9/2005 |
| WO | WO-2005/092899 A1 | 10/2005 |
| WO | WO-2005/102318 A1 | 11/2005 |
| WO | WO-2005/102325 A1 | 11/2005 |
| WO | WO-2005/102326 A2 | 11/2005 |
| WO | WO-2005/102346 A1 | 11/2005 |
| WO | WO-2005/102455 A2 | 11/2005 |
| WO | WO-2005/103022 A1 | 11/2005 |
| WO | WO-2005/112920 A1 | 12/2005 |
| WO | WO-2005/115304 A2 | 12/2005 |
| WO | WO-2005/115385 A1 | 12/2005 |
| WO | WO-2006/010750 A1 | 2/2006 |
| WO | WO-2006/038001 A1 | 4/2006 |
| WO | WO-2006/044509 A1 | 4/2006 |
| WO | WO-2006/058007 A2 | 6/2006 |
| WO | WO-2006/058905 A1 | 6/2006 |
| WO | WO-2006/064251 A1 | 6/2006 |
| WO | WO-2006/070943 A1 | 7/2006 |
| WO | WO-2006/077401 A1 | 7/2006 |
| WO | WO-2006/104983 A1 | 10/2006 |
| WO | WO-2006/108059 A1 | 10/2006 |
| WO | WO-2006/122011 A2 | 11/2006 |
| WO | WO-2007/008664 A1 | 1/2007 |
| WO | WO-2007/026251 A2 | 3/2007 |
| WO | WO-2007/030362 A1 | 3/2007 |
| WO | WO-2007/036732 A1 | 4/2007 |
| WO | WO-2007/037187 A1 | 4/2007 |
| WO | WO-2007/040440 A1 | 4/2007 |
| WO | WO-2007/055941 A2 | 5/2007 |
| WO | WO-2007/076034 A2 | 7/2007 |
| WO | WO-2007/076035 A2 | 7/2007 |
| WO | WO-2007/079185 A2 | 7/2007 |
| WO | WO-2007/087129 A2 | 8/2007 |
| WO | WO-2007/087717 A1 | 8/2007 |
| WO | WO-2007/093492 A1 | 8/2007 |
| WO | WO-2007/095124 A2 | 8/2007 |
| WO | WO-2007/100795 A2 | 9/2007 |
| WO | WO-2007/106192 A2 | 9/2007 |
| WO | WO-2007/127137 A2 | 11/2007 |
| WO | WO-2007/135036 A1 | 11/2007 |
| WO | WO-2008/033743 A1 | 3/2008 |
| WO | WO-2009/002534 A1 | 12/2008 |
| WO | WO-2009/079391 A1 | 6/2009 |
| WO | WO-2010/009139 A2 | 1/2010 |
| WO | WO-2010/009155 A2 | 1/2010 |
| WO | WO-2010/009166 A1 | 1/2010 |
| WO | WO-2010/014611 A1 | 2/2010 |

OTHER PUBLICATIONS

Lee, M. et al. (2003) "Molecular Targets for Cell Cycle Inhibition and Cancer Therapy", *Expert opinion on Therapeutic Patents.* 13(3):329-346.

Madhusudan, S. et al. (2004) "Tyrosine Kinase Inhibitors in Cancer Therapy", *Clinincal Biochemistry,* vol. 37, 00.618-635.

U.S. Office Action for U.S. Appl. No. 12/747,159, mailed Dec. 10, 2010.

U.S. Appl. No. 12/943,799, filed Nov. 10, 2010.

International Search Report for PCT/US2010/037647, International Filing Date Jun. 7, 2010, mailed Nov. 9, 2010.

Acharya et al. (2005) "Rational Development of Histone Deacetylase Inhibitors as Anticancer Agents" *A Review, Molecular Pharmacology* 68:917-932.

Alam et al. (2007) "Synthesis and SAR of Aminopyriidines as Novel c-Jun N-terminal Kinase (JNK) Inhibitors" *Science Direct, Bioorganic & Medicinal Chemistry Letters* 17:3463-3467.

Bush et al. (2009) "Targeting Histone Deacetylases for Heart Failure" *Myogen, Inc.* 1-39.

Feng et al. (2006) "Synthesis and SAR of 2-(4-fluorophenyl)-3-pyrimidin-4-ylimidazo[1,2-a]pyridine Derivatives as Anticoccidial Agents" *Science Direct, Bioorganic & Medicinal Chemistry Letters* 16:5978-5981.

Gudmundsson et al. (2007) "Imidazo[1,2-a]ayridines With Potent Activity Against Herpesviruses" *Scienc Direct, Bioorganic & Medicinal Chemistry Letters* 17:2735-2739.

International Search Report for PCT/US2008/007963, International Filing Date Jun. 26, 2008, mailed Oct. 1, 2008.

International Search Report for PCT/US2008/086643, International Filing Date Dec. 12, 2008, mailed Mar. 23, 2009.

International Search Report for PCT/US2009/050558, International Filing Date Jul. 14, 2009, mailed Oct. 12, 2009.

International Search Report for PCT/US2009/050577, International Filing Date Jul. 14, 2009, mailed Nov. 11, 2009.

International Search Report for PCT.US2009/050595, International Filing Date Jul. 14, 2009, mailed Nov. 18, 2009.

International Search Report for PCT/US2009/051964, International Filing Date Jul. 28, 2009, mailed Oct. 2, 2009.

International Search Report for PCT/US2010/037647, International Filing Date Jun. 7, 2010, mailed Sep. 11, 2010.

Mahboobi et al. (2007) "2-Aroylindoles and w-Arolbenzofurans with N-Hydroxyacrylamide Substructures as a Novel Series of Rationally Designed Histone Deacetylase Inhibitors" *American Chemical Society* A-N.

Marcou et al. (2007) "Optimizing Fragment and Scaffold Docking by Use of Molecular Interaction Fingerprints" *Journal of Chemistry Inf. Model* 47(1):195-207.

Moradeli et al. (2005) "Histone Deacetylase Inhibitors" *Latest Developments, Trends, and Prospects, Current Medicinal Chemistry—Anti-Cancer Agents* 529-560.

Paris et al. (2008) "Histone Deacetylase Inhibitors: From Bench to Clinic" *Journal of Medicinal Chemistry* A-Y.

Price et al. (2007) Histone Deacetylase Inhibitors: An Analysis of REcent Patenting Activity *Informa UK Ltd, Expert Opinion, Ther. Patents* 745-765.

Rosato et al. (2003) "The Histone Deacetylase Inhibitor MS-275 Promotes Differentation or Apoptosis in Human Leukemia Cells Through a Process Regulated by Generation of Reactive Oxygen Species and Induction of p. 21" *Cancer Research* 63:3637-3645.

U.S. Appl. No. 12/795,575, filed Jun. 7, 2010.

\* cited by examiner

ALKANOYLAMINO BENZAMIDE ANILINE HDAC INHIBITOR COMPOUNDS

CROSS-REFERENCE TO RELATED APPLICATIONS

This application is filed under 35. U.S.C. 111(a) claiming the benefit under 35 U.S.C. 119(e) of U.S. Provisional Patent Application No. 61/185,126 filed Jun. 8, 2009, which is herein incorporated by reference in its entirety for all purposes.

FIELD

The present invention generally relates to compounds having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2, -3, and -8) compounds are closely related to yeast RPD3; class IIa (HDAC-4, -5, -7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor $NAD^+$ for their deacetylase function. See, for example, Marielle Paris et al., *Histone Deacetylase Inhibitors: From Bench to Clinic*, JOURNAL OF MEDICINAL CHEMISTRY 51(11I): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradei et al., *Histone Deacetylase Inhibitors: Latest Developments, Trends, and Prospects*, CURR. MED. CHEM.: ANTI-CANCER AGENTS 5(5):529-560 (2005).

US RE39,754 to Suzuki describes benzamide derivatives which contain a substituted or unsubstituted nitrogen-containing heteroaryl group. Suzuki mentions that the benzamide derivatives are useful as therapeutics for malignant tumors, specifically for a hematologic malignancy or a solid carcinoma.

WO 2009/002495 describes 4-carboxybenzylamino compounds which contain an oxycarbamoylmethylene group attached to a pyridin-3-ylmethyl group in relation to inhibition of a histone deacetylase.

WO 2009/002534 mentions imidazopyridinyl compounds linked to anilide or hydroxamate moiety via thiazolylamino linker. The compounds are described as having enzyme inhibitory activity such as histone deacetylase inhibitory activity.

There is a continued need to develop new inhibitors to provide appropriate therapy for a variety of disease conditions implicated in HDAC activity.

SUMMARY

In various embodiments, a compound having HDAC inhibitory activity, a composition comprising the compound, and a method useful to treat diseases arising from abnormal cell proliferation or differentiation are provided.

In an embodiment, there is provided a compound of Formula (I) or a pharmaceutically acceptable salt thereof:

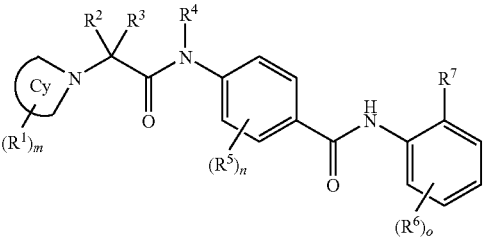

Formula (I)

wherein

Cy is heterocyclyl containing at least one nitrogen ring atom, wherein Cy is optionally substituted with one or more $R^1$ where chemically feasible;

m is an integer from 0 to the maximum number of substitutable positions on Cy;

$R^1$ is independently selected from the group consisting of:

(a) H, cyano, oxo, halo, nitro, hydroxy, alkoxy, amino, mercapto, alkyl, aryl, cycloalkyl, heterocyclyl, and heterocyclylalkyl; and (b) $R^8$—C(O)—$X^1$—, $R^8$—O—C(O)—$X^1$— and $R^8$—S$(O)_a$—$X^1$—, wherein $X^1$ is selected from the group consisting of a bond, —NH—, —NH—$C_{1-6}$ alkylene, —O—$C_{1-6}$ alkylene, $C_{1-6}$ alkylene, $C_{2-6}$ akenylene, $C_{2-6}$ alkynylene, $C_{3-6}$ cycloalkylene, arylene, and heterocyclylene; and $R^8$ is selected from the group consisting of H, amino, hydroxy, alkyl, alkylamino, N-alkylamino, N,N-dialkylamino, cycloalkyl, heterocyclyl, and aryl; and a is 0, 1 or 2, wherein $R^1$ is optionally substituted with one or more A where such an optional substitution is chemically feasible; or when m is 2, the two $R^1$ groups can be substituted on the same carbon ring atom of Cy and together with the carbon ring atom of Cy form a ring situated on Cy in a spiro configuration, wherein the spiro ring is cycloalkyl or heterocycloalkyl;

$R^2$ and $R^3$ are independently selected from the group consisting of:

(a) H, alkyl, alkenyl, alkynyl, cycloalkyl, cycloalkylalkyl, heterocyclyl, heterocyclylalkyl, aryl, and aryl alkyl;

(b) $R^9$—C(O)—$X^2$—, $R^9$—O—C(O)—$X^2$— and $R^9$—S$(O)_a$—$X^2$—, wherein $X^2$ is selected from the group consisting of a bond, —NH—, —NH—$C_{1-6}$ alkylene, —O—$C_{1-6}$ alkylene, $C_{1-6}$ alkylene, $C_{2-6}$ akenylene, $C_{2-6}$ alkynylene, $C_{3-6}$ cycloalkylene, arylene, and heterocyclylen;

$R^9$ is selected from the group consisting of H, hydroxy, amino, alkyl, N-alkylamino, N,N-dialkylamino, cycloalkyl, aryl, and heterocyclyl; and a is 0, 1 or 2;

wherein at least one of $R^2$ and $R^3$ is a non-hydrogen substitution, and each $R^2$ and $R^3$ is optionally substituted with one or more B where such an optional substitution is chemically feasible;

R⁴ is selected from the group consisting of —H, alkyl, cycloalkyl, heterocycloalkyl, aryl, heteroaryl, cycloalkylalkyl, heterocycloalkylalkyl, aralkyl, heteroaralkyl, alkylamino, alkylaminoalkyl, cycloalkylamino, heterocycloalkylamino, and arylamino wherein R⁴ is optionally substituted with one or more selected from halo, oxo, hydroxy, amino, alkylamino, carbamoyloxy, carbamoyl, cycloalkyl, cycloalkenyl, heterocyclyl and aryl where such an optional substitution is chemically feasible;

R⁵ is independently selected from the group consisting of halo, hydroxy, nitro, cyano, haloalkyl, haloalkoxy, amino, carboxy, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl) amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_n$ wherein a is 0, 1 or 2, NH$_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl;

n is 0, 1, 2, 3 or 4;

R⁶ is independently selected from the group consisting of —H, halo, haloalkyl, aryl and heteroaryl wherein the aryl or heteroaryl is optionally substituted with one or more substituents selected from amino, halo, alkyl, haloalkyl, cycloalkyl, heterocycloalkyl, aryl and heteroaryl;

R⁷ is NH$_2$— or OH—;

o is 0, 1, 2, 3 or 4;

A is independently selected from the group consisting of halo, hydroxy, amino, carboxy, carbamoyl, $C_{1-10}$ alkyl, $C_{1-10}$ alkoxy, N—($C_{1-10}$ alkyl)amino, N,N—($C_{1-10}$ dialkyl)amino, N—($C_{1-10}$alkyl)carbamoyl, N,N—($C_{1-10}$ dialkyl)carbamoyl, $C_{1-10}$ haloalkyl, $C_{3-10}$ cycloalkyl, heterocycloalkyl, aryl, heteroaryl, ($C_{1-10}$ alkyl)$C_{3-10}$ cycloalkyl, and R(R')(R'')silyl wherein R, R' and R'' are independently alkyl or aryl; and B is independently selected from the group consisting of oxo, halo, amino, hydroxy, cyano, carbamoyl, $C_{1-10}$ alkyl, $C_{1-10}$ alkoxy, $C_{1-10}$ haloalkyl, $C_{1-10}$ alkanoylamino, N—($C_{1-10}$ alkyl)amino, N,N—($C_{1-10}$ dialkyl)amino, $C_{1-10}$ alkanoyl, N—($C_{1-10}$ alkyl)carbamoyl, N,N—($C_{1-10}$ dialkypearbarnoyl, $C_{3-10}$ cycloalkyl, ($C_{3-10}$ cycloalkyl)$C_{1-10}$ alkyl, $C_{3-10}$ cycloalkoxy, $C_{1-10}$ haloalkoxy, heterocyclyl, (heterocyclyl)$C_{1-10}$ alkyl, aryl, (aryl)$C_{1-10}$ alkyl, (heteroaryl)$C_{1-10}$ alkyl and R(R')(R'')silyl wherein R, R' and R'' are independently alkyl or aryl.

In another embodiment, there is provided a compound of Formula (II) or a pharmaceutically acceptable salt thereof:

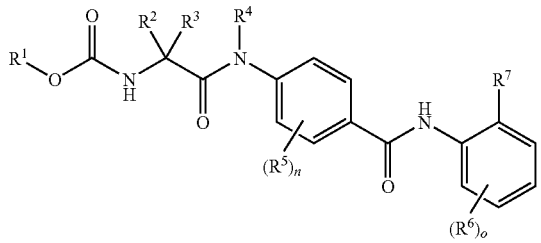

Formula (II)

wherein

R¹ is selected from the group consisting of alkyl, aryl, aralkyl, cycloalkyl, cycloalkylalkyl, alkylcycloalkyl, haloalkyl, heteroarylalkyl, haloalkylheteroaryl, and cycloalkylheteroaryl, wherein R¹ is optionally substituted with alkyl; and o, n, R², R³, R⁴, R⁵, R⁶ and R⁷ are as defined above.

In yet another embodiment, there is provided a pharmaceutical composition comprise an HDAC-inhibitory effective amount of one or more compounds described herein and a pharmaceutically-acceptable carrier.

In yet another embodiment, there is provided a method of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

The compounds above are more fully described in the detailed description that follows.

DETAILED DESCRIPTION

The following description is merely exemplary in nature and is not intended to limit the present disclosure, application, or uses.

Definitions

"Alkenyl" refers to a straight or branched hydrocarbyl group with at least one site of unsaturation, i.e. a carbon-carbon, sp² double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=CH$_2$), allyl (—CH$_2$CH=CH$_2$), cyclopentenyl (—C$_5$H$_7$), and 5-hexenyl (—CH$_2$CH$_2$CH$_2$CH$_2$CH=CH$_2$).

"Alkanoyl" is the group RC(O)—; "alkanoyloxy" is RC(O) O—; and "alkanoylamino" is RC(O)NR'—; where R is an alkyl group as defined herein, and R' is hydrogen or alkyl. In various embodiments, R is a $C_1$-$C_{10}$ alkyl group or a $C_1$-$C_6$ alkyl group.

"Alkanoylalkyl" is the group RC(O)R'—, wherein R and R' are independently selected alkyl.

"Alkanoyloxyalkyl" is the group RC(O)OR'—, wherein R and R' are independently selected alkyl.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkoxycarbonylalkyl" is the group ROC(O)R'—, wherein R and R' are independently selected alkyl.

"Alkyl" refers to a straight or branched chain hydrocarbyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RHN— and "N,N-(alkyl)$_2$amino" is R$_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methyl amino, ethylamino, propyl amino, butylamino, N,N-dimethylamino, N,N-diethylamino, and methylethylamino.

"Alkylaminoalkyl" refers to an alkyl moiety substituted with an alkylamino group, wherein alkylamino is as defined herein. Examples of alkylaminoakyl groups include methylaminomethyl and ethylaminomethyl.

"Alkylcycloalkyl" is an alkyl group, as defined herein, substituted with a cycloalkyl group, also as defined herein.

"N-(alkyl)carbamoyl" is the group R—NH—C(O), wherein R is alkyl as defined herein. In various embodiments, R is a $C_1$-$C_{10}$ alkyl group or a $C_1$-$C_6$ alkyl. Examples of alkylcarbamoylalkyl groups include, but are not limited to, N-methylcarbamoyl, N-ethylcarbamoyl, N-propylcarbamoyl and N-butylcarbamoyl. "N,N-(Alkyl)$_2$-carbamoyl" and "N,N-dialkylcarbamoyl" is the group (R)R'N—C(O)—, wherein R and R' are independently selected alkyl as defined herein. In various embodiments, R and R' are $C_1$-$C_{10}$ alkyl groups or $C_1$-$C_6$ alkyl groups. Examples of N,N-dialkylcarbamoyl groups include, but are not limited to, N,N-dimethylcarbamoyl, N,N-methylethylcarbamoyl, N,N-diethylcarbamoyl, N,N,-dipropylcarbamoyl and N,N-dibutylcarbamoyl.

"Alkylcarbamoylalkyl" is the group R—NH—C(O)—R', wherein R and R' are independently selected alkyl as defined herein. In various embodiments, R and R' are $C_1$-$C_{10}$ alkyl groups or $C_1$-$C_6$ alkyl groups. Examples of alkylcarbamoylalkyl groups include, but are not limited to, N-methylcarbamoylmethyl, N-methylcarbamoylethyl, N-ethylcarbamoylmethyl, N-ethylcarbamoylethyl, N-propylcarbamoylethyl and N-butylcarbamoylethyl.

"Alkylsulfinyl" is the group RS(O)—, wherein R is alkyl as defined herein. In various embodiments, R is $C_1$-$C_{10}$ alkyl group or a $C_1$-$C_6$ alkyl group. Examples of alkylsulfinyl groups include, but are not limited to, methylsulfinyl, ethylsulfinyl, propylsulfinyl and butylsulfinyl.

"Alkylsulfonyl" is the group RS(O)$_2$—, wherein R is alkyl as defined herein. In various embodiments, R is $C_1$-$C_{10}$ alkyl group or $C_1$-$C_6$ alkyl group. Examples of alkylsulfonyl groups include, but are not limited to, methylsulfonyl, ethylsulfonyl, propylsulfonyl and butylsulfonyl.

"Alkylthio" is the group RS—, wherein R is alkyl as defined herein. In various embodiments, R is $C_1$-$C_{10}$ alkyl group or a $C_1$-$C_6$ alkyl group. Examples of alkylthio groups include, but are not limited to, methylthio, ethylthio, propylthio and butylthio.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—CH$_2$C≡CH).

"Aminoalkyl" is the group H$_2$NR—, wherein R is alkyl as defined herein. Examples of aminoalkyl groups include, but are not limited to, aminomethyl, 1-aminoethyl, 2-aminoethyl, 1-aminopropyl, 2-aminopropyl and 3-aminopropyl.

"Aminosulfonylalkyl" is the group H$_2$NS(O)$_2$R—, wherein R is alkyl as defined herein. Examples of aminosulfonylalkyl groups include, but are not limited to aminosulfonylmethyl, aminosulfonylethyl, aminosulfonylpropyl and aminosulfonylbutyl.

"Aryl" refers to any monocyclic or bicyclic carbon ring of up to 7 atoms in each ring, wherein at least one ring is aromatic. Aryl encompasses a ring system of up to 14 carbons atoms that includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" and "Aralkyl" refer to any alkyl group, as defined herein, substituted with any aryl group, also as defined herein. Examples of aralkyl groups include, but are not limited to, benzyl, phenylethyl, naphthylmethyl, tetrahydronaphtylmethyl and indanylmethyl.

"Arylamino" is the group RHN—, wherein R is aryl as defined herein. Examples of arylamino groups include, but are not limited to, phenylamino, naphthylamino, tetrahydronaphthylamino and indanylamino.

"Aryloxy" is RO—, where R is aryl. "Arylthio" is RS—, where R is aryl.

"Arylsulfonyl" is the group RS(O)$_2$—, wherein R is aryl as defined herein. Examples of arylsulfonyl groups include, but are not limited to, phenylsulfonyl, naphthylsulfonyl, tetrahydronaphthylsulfonyl and indanylsulfonyl.

"Arylthio" is the group RS—, wherein R is aryl as defined herein. Examples of arylthio groups include, but are not limited to, phenylthio, naphthylthio, tetrahydronaphthylthio and indanylthio.

"Arylthioalkyl" refers to any alkyl group, as defined herein, substituted with any arylthio group, as also defined herein. Examples of arylthioalkyl groups include, but are not limited to, phenylthiomethyl, naphthylthiomethyl, tetrahydronaphthylthiomethyl, indanylthiomethyl, phenylthioethyl, naphthylthioethyl, tetrahydronaphthylthioethyl and indanylthioethyl.

"Carbonyl" is the group —C(O)—, which can also be written as —(C═O)—. The carbonyl group can be found in several chemical moieties, such as acids, aldehydes, amides, cabamates, carboxylates, esters, and ketone; and functional groups, such as carbamoyl, alkanoyl, cycloalkanoyl, and heterocycloalkanoyl.

"Carbamoyloxy" refers to the group H$_2$NC(O)O—.

"Carbamoyl" is the group NH$_2$—C(O)—; the nitrogen can be substituted with alkyl groups. N-(alkyl)carbamoyl is RNH—C(O)— and N,N-(alkyl)$_2$ carbamoyl is R$_2$N—C(O)—, where the R groups are alkyl as defined herein and are the same or different. In various embodiments, R is a $C_1$-$C_{10}$ alkyl group or a $C_1$-$C_6$ alkyl group.

"Carbamoylalkyl" refer to the group NH$_2$C(O)R—, wherein R is alkyl as defined herein. Examples of carbamoylalkyl groups include, but are not limited to, carbamoylmethyl, carbamoylethyl, carbamoylpropyl and carbamoylbutyl.

"Carboxy" is the group HOC(O)—, and can also be referred to as a carboxylic acid.

"Cycloalkanoyl" is the group RC(O)—, wherein R is cycloalkyl as defined herein. Examples include, but are not limited to, cyclopropanoyl, cyclobutanoyl, cyclopentanoyl and cyclohexanoyl.

"Cycloalkylalkanoyl" is the group RC(O)—, wherein R is cycloalkyl as defined herein. Examples include, but are not limited to, cyclopropanoyl, cyclobutanoyl, cyclopentanoyl and cyclohexanoyl.

"Cycloalkylaminosulfonyl" is the group R—NH—S(O)$_2$—, wherein R is cycloalkyl as defined herein. Examples of cylcoalkylaminosulfonyl groups include, but are not limited to, cyclopropylaminosulfonyl, cyclobutylaminosulfonyl, cyclopentylaminosulfonyl and cyclohexylaminosulfonyl.

"Cycloalkylaminosulfinyl" is the group R—NH—S(O)—, wherein R is cycloalkyl as defined herein. Examples of cylcoalkylaminosulfinyl groups include, but are not limited to, cyclopropylaminosulfinyl, cyclobutylaminosulfinyl, cyclopentylaminosulfinyl and cyclohexylaminosulfinyl.

"Cycloalkylcarbonyl" and "cycloalkanoyl" refer to the group RC(O)—, wherein are is cycloalkyl as defined herein. Examples of cycloalkylcarbonyl groups include, but are not limited to, cyclopropylcarbonyl, cyclobutylcarbonyl, cyclopentylcarbonyl and cylcohexylcarbonyl.

"Cycloalkyl" is a saturated or partially unsaturated, mono-, bi- or tri-cyclic hydrocarbon group. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

In various embodiment, the term, cycloalkyl, is a bridged cycloalkyl group and non-limiting examples of which include:

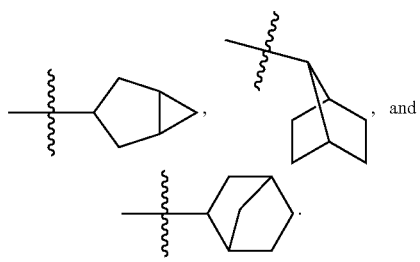

"Cycloalkylamino" is the group R—NH—, wherein R is cycloalkyl as defined herein. Examples include, but are not limited to, cyclopropylamino, cyclobutylamino, cyclopenylamino and cyclohexylamino.

"Cycloalkyloxy" is RO—, where R is cycloalkyl.

"Cycloalkyloxysulfonyl" and "cylcoalkoxysulfonyl" refer to the group $ROS(O)_2$—, wherein R is cycloalkyl as defined herein. Examples of cycloalkyloxysulfonyl groups include, but are not limited to, cyclopropyloxysulfonyl, cyclobutyloxysulfonyl, cyclopentyloxysulfonyl and cyclohexyloxysulfonyl.

"Cycloalkyloxysulfinyl" and "cylcoalkoxysulfinyl" refer to the group ROS(O)—, wherein R is cycloalkyl as defined herein. Examples of cycloalkyloxysulfinyl groups include, but are not limited to, cyclopropyloxysulfinyl, cyclobutyloxysulfinyl, cyclopentyloxysulfinyl and cyclohexyloxysulfinyl.

"Cycloalkylalkyl" refers to an alkyl moiety substituted with a cycloalkyl group, wherein cycloalkyl is as defined herein. Examples of cycloalkylalkyl groups include, but are not limited to, cyclopropylmethyl, cyclobutylmethyl, cyclopentylethyl and cyclohexylmethyl.

"Cycloalkylalkyl —$S(O)_2$—" and "cycloalkylalkylsulfonyl" refer to the group R—R'—$S(O)_2$, wherein R is a cycloalkyl as defined herein, and R' is an alkyl as also defined herein. Examples of cycloalkylalkyl-$S(O)_2$— include, but are not limited to, cyclopropylmethyl-$S(O)_2$—, cyclobutylmethyl-$S(O)_2$—, cyclopentylmethyl-$S(O)_2$—, cyclopenyl-ethyl-$S(O)_2$— and cyclohexylmethyl-$S(O)_2$—.

"Cycloalkylsulfonyl" is the group $RS(O)_2$—, wherein the R is cycloalkyl as defined herein. Examples of cycloalkylsulfonyl groups include, but are not limited to, cyclopropylsulfonyl, cyclobutylsulfonyl, cyclopentylsulfonyl and cyclohexylsulfonyl.

"Dialkylamino" refers to an RR'N— group where R and R' are independently selected alkyl as defined herein. Examples of dialkylamino groups include, but are not limited to, N,N-dimethylamino, N,N-diethylamino, methylethylamino and methylpropylamino. In various embodiments, R and R' are independently a $C_1$-$C_{10}$ alkyl group or a $C_1$-$C_6$ alkyl group.

"Dialkylaminoalkyl" refers to an alkyl moiety substituted with a dialkylamino group, wherein dialkylamino is as defined herein. Examples of dialkylaminoalkyl groups include, but are not limited to, N,N-dimethylaminomethyl and N,N-diethylaminomethyl.

"Dialkylcarbamoyl" is the group RR'N—C(O)—, wherein R and R' are independently selected alkyl as defined herein. In various embodiments, R and R' are $C_1$-$C_{10}$ alkyl groups or $C_1$-$C_6$ alkyl groups. Examples of N,N-dialkylcarbamoyl groups include, but are not limited to, N,N-dimethylcarbamoyl, N,N-methylethylcarbamoyl, N,N-diethylcarbamoyl, N,N,-dipropylcarbamoyl and N,N-dibutylcarbamoyl.

"Dialkylheterocycloalkyl-$S(O)_2$—" and "dialkylheterocloalkylsulfonyl" refer to the group $RS(O)_2$—, wherein R is a hereocycloalkyl, as defined herein, substituted with two independently selected alkyl, as also defined herein.

The suffix "-ene" on a the name of a chemical moiety refers to any divalent, carbon-containing species, including, but not limited to, alkylene, alkenylene, alkynylene, cycloalkylene, heterocycloalkylene, arylene, heteroarylene, cyclylene, and heterocyclylene. The two attachments to the divalent moiety can occur on the same atom or on different atoms, when chemically feasible.

In various embodiments, examples of "Alkylene" include, but are not limited to, methylene, ethylene, propylene, isopropylene, butylene, isobutylene, sec-butylene, and tert-butylene. For alkylenes greater than one carbon in length, attachment can occur on the same carbon or on different carbons. For example, butylene can be attached as follows:

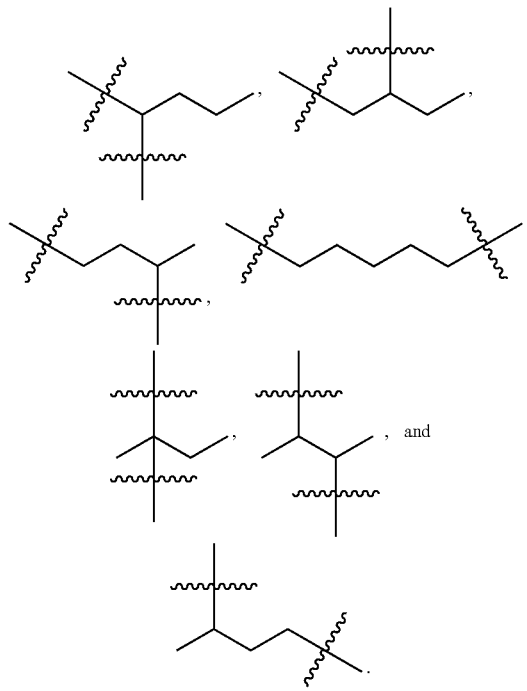

In various embodiments, "Arylene" refers to a divalent aryl substituent, as defined herein. The attachments can be in an ortho, meta, or para configuration.

"Feasible" refers to a structure or process which is capable of being accomplished, possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use. Chemically feasible structures are bound by the rules of electron bonding, whereby bonds can only be formed between atoms that are capable of forming bonds with one another. Likewise, chemically feasible processes can only produce structures which are themselves chemically feasible. Explosive, touch-sensitive, and pyrophoric substance or substances which undergo exothermic unimolar decompositions at high rates are typically not considered chemically feasible.

"Halo" refers to chloro (—Cl), bromo (—Br), fluoro (—F) or iodo (—I).

"Haloalkoxy" refers to an alkoxy group substituted with one or more halo groups and examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Haloaryl" refers to any aryl group which is substituted with one or more independently selected halo group.

"Heteroaryl" is a heterocyclyl where at least one ring is aromatic. In various embodiments, it refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuran yl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylalkyl" refers to an alkyl group, as defined herein, substituted with a heteroaryl group, also as defined herein. Examples of heteroarylalkyl groups include, but are not limited to, pyridylmethyl, pyridylethyl, thienylpropyl and furanylbutyl.

"Heteroaryloxy" is RO—, where R is heteroaryl.

"Heteroarylsulfonyl" is the group RS(O)$_2$—, wherein the R is heteroaryl as defined herein. Examples of heteroarylsulfonyl groups include, but are not limited to, pyridylsulfonyl, thienylsulfonyl, furanylsulfonyl, pyrimidylsulfonyl and imidazolylsulfonyl.

"Heterocycloalkyl" refers to a saturated, or partially unsaturated monocyclic, bicyclic or tricyclic group of 2 to 14 ring-carbon atoms containing one or more heteroatoms selected from P, N, O and S, in addition to ring-carbon atoms. In various embodiments the heterocyclic group is attached to another moiety through carbon or through a heteroatom, and is optionally substituted on carbon or a heteroatom. Examples of heterocycloalkyl include morpholinyl, thiomorpholinyl, and

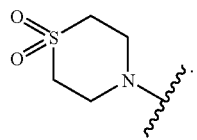

In various embodiment, the term, "heterocycloalkyl," is a bridged cycloalkyl group and examples of which include:

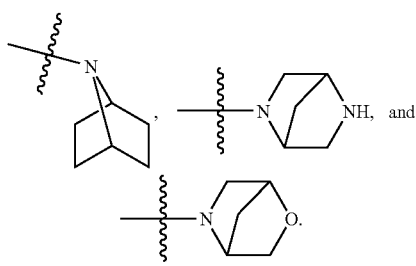

"Heterocycloalkylalkyl" refers to any alkyl group, as defined herein, substituted with any heterocycloalkyl group, as also defined herein.

"Heterocycloalkylamino" is the group RHN—, wherein R is a heterocycloalkyl, as defined herein. Examples of heterocycloalkylamino groups include, but are not limited to, azetidinylamino, benzoimidazolylamino, benzofuranylamino, benxopyrazolyl and benzotriazoylamino.

"Heterocycloalkyl-S(O)$_2$—" and "heterocycloalkylsulfonyl" refer to the group RS(O)$_2$, wherein R is heterocycloalkyl as defined herein.

"Heterocycloalkyl (C=O)" "heterocycloalkylcarbonyl" and "heterocycloalkanoyl" refer to the group RC(O)—, wherein R is heterocycloalkyl as defined herein.

"Heterocycloalkyloxy" is RO—, where R is heterocycloalkyl. "Heterocycloalkylthio" is RS—, where R is heterocycloalkyl.

"Heterocyclyl" includes the heteroaryls and the heterocycloclkyls defined herein and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclylalkyl" is an alkyl group substituted with a heterocyclyl.

"Hydroxyalkoxy" refers to an alkoxy group substituted with a hydroxy group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

"Mercapto" refers to the sulfhydryl group HS—.

"Sulphamoyl" is $NH_2$—$S(O)_2$—; "N-(alkyl)sulphamoyl" is R—NH—$S(O)_2$—; and "N,N-(alkyl)$_2$ sulphamoyl" is $R_2N$—$S(O)_2$—, where the R groups are alkyl as defined herein and are the same or different. In various embodiments, R is a $C_1$-$C_{10}$ alkyl group or a $C_1$-$C_6$ alkyl group.

"Trialkylsilyl" is the group R(R')(R")Si—, wherein R, R' and R" are each independently selected alkyl. Examples include, but are not limited to, trimethylsilyl, triethylsilyl, triisopropylsilyl, and t-butyldimethylsilyl.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, or other ingredient which is pharmaceutically-acceptable and with which a compound of the invention is administered.

"Pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-en-1-carboxylic acid, glucoheptonic acid, 4,4'-methylen-bis(3-hydroxy-2-naphthoic) acid, 3-phenylpropionic acid, trimethylacetic acid, tert-butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, there is provided a compound selected from those of Formula (I) and pharmaceutically acceptable salts thereof:

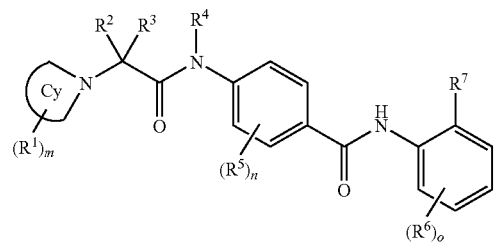

Formula (I)

wherein Cy, $R^1$, $R^2$, $R^3$, $R^4$, $R^5$, $R^6$, $R^7$, m, n and o are as defined above.

In an embodiment, Cy is heterocyclyl containing 4, 5 or 6 ring atoms, one of which is a nitrogen ring atom attached to the remaining molecule, wherein the heterocyclyl is optionally substituted with one or more $R^1$. Non-limiting examples of such heterocyclyls include pyrrolidinyl, oxopyrrolidinyl, morpholinyl, piperazinyl, piperidinyl, azetidinyl,

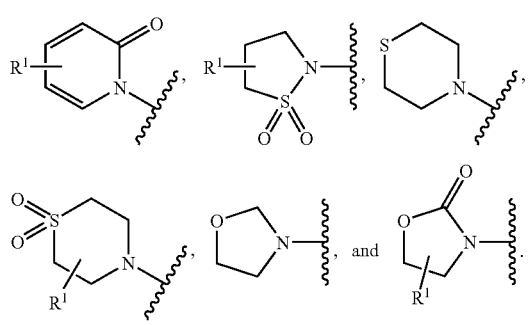

In a particular embodiment, Cy is pyrrolidinyl or pyrrolidinyl fused with a saturated or unsaturated ring structure, wherein Cy is optionally substituted with one or more $R^1$. In one embodiment, Cy is pyrrolidinyl fused with a saturated or unsaturated ring structure having 5 or 6 ring members, wherein the cyclic moiety can contain one or more heteroatoms selected from N, O and S. Non-limiting examples of such fused rings include:

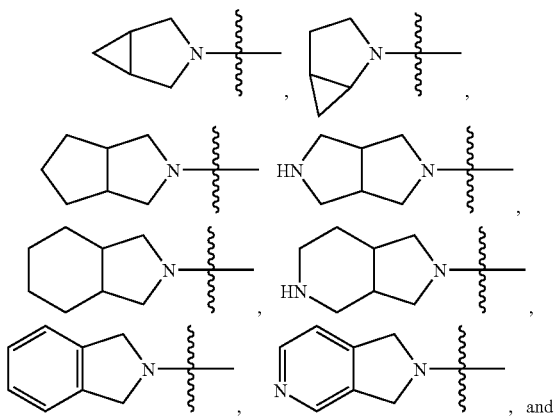

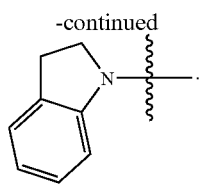

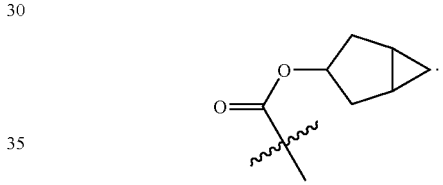

In one embodiment, substituted or unsubstituted pyrrolidinyl described herein is optionally substituted with $R^1$ which is selected from 2-oxo, 2-hydroxy, 2-methyl, 2,5-dioxo, 4-hydroxy-2-oxo, 2-dialkylamino, 2-carboxy, 2-(N,N-dialkyl)carbamoyl, 5-oxo-2-(N,N-dialkyl)carbamoyl, 2-hydroxymethyl, 2-(1-hydroxycyclopropyl), 3-fluoro, 2-methyl-2-carboxy, 3-trifluoromethyl, and 4-trifluoromethyl-2-carboxy.

In another particular embodiment, Cy is piperidinyl or piperidinyl fused with a saturated or unsaturated ring structure, wherein Cy is optionally substituted with one or more $R^1$. In one embodiment, Cy is piperidinyl fused with a saturated or unsaturated ring structure having 5 or 6 ring members, wherein the cyclic moiety can contain one or more heteroatoms selected from N, O and S. Non-limiting examples of such fused rings include:

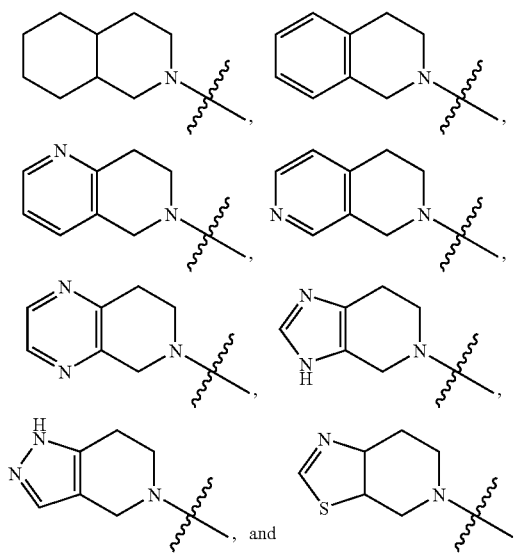

In one embodiment, substituted or unsubstituted piperidinyl described herein is substituted with $R^1$ which is selected from 4-hydroxy-4-methyl, 4-hydroxy-4-trifluoromethyl, 4-hydroxy-4-cyclopropyl, 4-(2,2,2-trifluoroethylamino), 4-(5-oxo-1,4-diazepan-1-yl), 4-acetamido, 4-(1-methylcyclopropylamino), 4-cyano, 4-carboxy-4-methyl, N,N-dimethylcarbamoylmethyl, 4-oxo, 4-phenyl, 4-pyridin-3-yl, 4-(5-trifluoromethylpyridin-3-yl), N,N-dimethylcarbamoyl, 2-aminomethyl, 3-hydroxy, 2-cyclobutyl, 2-carboxy, 4-(1-alkylpiperidin-4-yl), and 3-cyclobutylamino.

In yet another particular embodiment, Cy is piperazinyl or piperazinyl fused with a saturated or unsaturated ring structure, wherein Cy is optionally substituted with one or more $R^1$. In one embodiment, Cy is piperazinyl fused with a saturated or unsaturated ring structure having 5 or 6 ring members, wherein the cyclic moiety can contain one or more heteroatoms selected from N, O and S. Non-limiting examples of such fused rings include:

In one embodiment, substituted or unsubstituted piperazinyl described herein is optionally substituted with $R^1$ which is selected from methyl, 1-methylcyclopropyl, trifluomethyl, methoxypropyl, N,N-dimethylaminopropyl, 1-carboxycyclopropyl, N,N-dimethylcarbamoylcyclopropyl, pyridin-2-ylmethyl, 5-trifluoromethylpyridin-2-ylmethyl, N,N-dimethylcarbamoyl, morpholinylcarbonyl, t-butylcarbamoyl, morpholinoethoxycarbonyl, benzoyl, picolinoyl, quinoxa-6-linylcarbonyl, cyclopropylcarbonyl, propionyl, methoxypropanoyl, N,N-dimethylaminopropanoyl, 5-trifluoromethylpyridin-2-yl, 5-chloropyridin-2-yl, 5-cyclopropylpyridin-2-yl, 5-chloropyrimidin-2-yl, 2-methoxyphenyl, 4-carboxyphenyl, N,N-dimethylcarbamoylphenyl, 2-chlorophenyl, 1-methylcyclopropoxycarbonyl, t-butoxycarbonyl, 2-trifluoromethylprop-2-oxycarbonyl, methylsulfonyl, trifluoroethylsulfonyl, 5-trifluoromethylpyridin-3-ylsulfonyl, pyridin-3-ylsulfonyl, phenylsulfonyl, cyclopropylsulfonyl, pyridin-2-yl, 5-trifluoromethylpyridin-2-yl, phenyl, cyclopropyl, ethyl, and

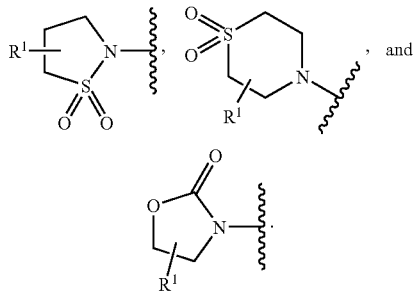

In yet another embodiment, Cy is heterocyclyl containing 4, 5 or 6 ring atoms which contain a nitrogen ring atom attached to the remaining molecule and an additional heteroatom, wherein the heterocyclyl is optionally substituted with one or more $R^1$. Non-limiting examples of such heterocyclyls include:

In another embodiment, Cy is heterocyclyl contain a bridge which connects two carbon ring atoms of the heterocyclyl, wherein the bridge is a direct bond or a divalent chain containing one or more carbons or heteroatoms selected from N, O and S, and wherein the heterocyclyl containing a bridge is optionally substituted with one or more $R^1$. Non-limiting examples of such bridged ring moieties include:

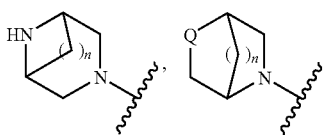

such as, for example,

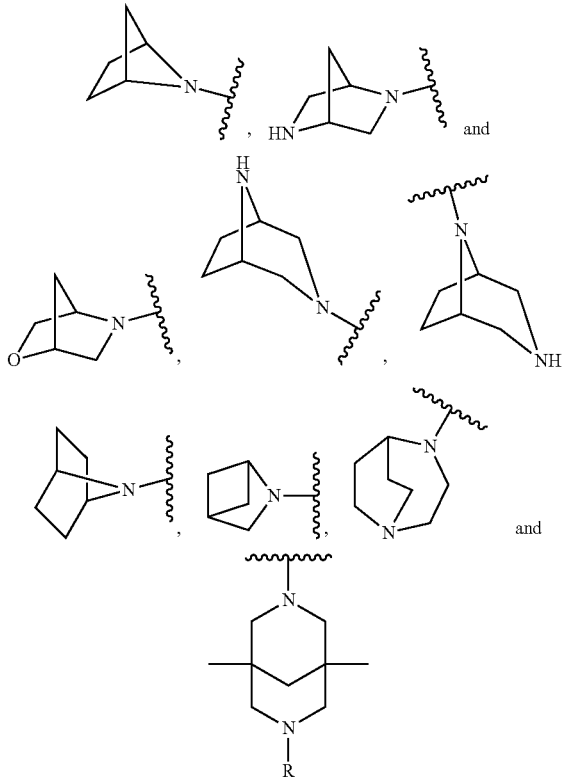

wherein n is 0, 1, 2 or 3; and Q is —NH—, —CH$_2$—, or —O—.

In various embodiments, a bridged ring as described herein is optionally substituted with one or more R$^1$, and non-limiting examples of such substituted, bridged rings include:

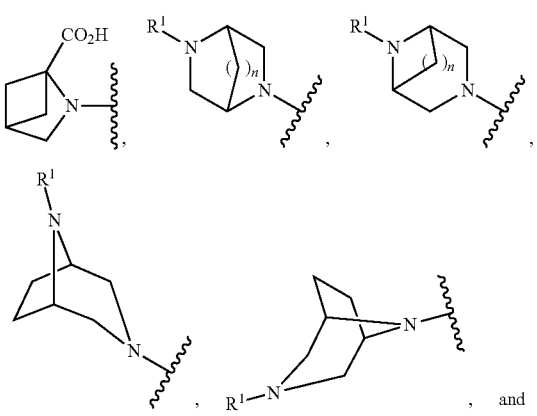

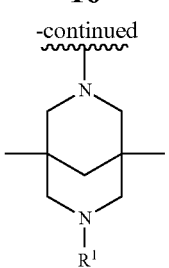

wherein n and R$^1$ are as defined above.

In yet another embodiment, two groups R$^1$ are substituted on the same carbon ring atom of Cy and together with the carbon ring atom of Cy form a ring situated on Cy in a Spiro configuration, wherein the spiro ring is cycloalkyl or heterocycloalkyl. Non-limiting examples of such spiro rings include:

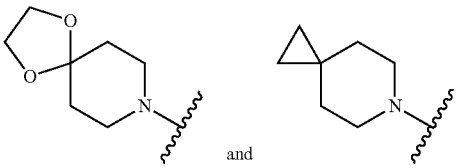

In yet another embodiment, R$^1$ is selected from the group consisting of cyano, oxo, halo, nitro, hydroxy, haloalkoxy, amino, mercapto, alkyl, aryl, cycloalkyl, heterocyclyl, heterocyclylalkyl, R$^8$—C(O)—X$^1$—, R$^8$—O—C(O)—X$^1$— and R$^8$—S(O)$_n$—X$^1$—, wherein X$^1$ is a bond, —NH—, —NH—C$_{3-6}$alkylene, —O—C$_{1-6}$ alkylene, C$_{1-6}$ alkylene, C$_{2-6}$ akenylene, C$_{2-6}$ alkynylene, C$_{3-6}$ cycloalkylene, arylene, and heterocyclylene; and R$^8$ is selected from the group consisting of H, amino, hydroxy, alkyl, haloalkyl, alkylamino, N-alkylamino, N,N-dialkylamino, cycloalkyl, heterocyclyl, and aryl; and a is 0, 1 or 2, wherein R$^1$ is optionally substituted with one or more A.

In various embodiments, R$^2$ and R$^3$ are independently selected from the group consisting of —H, cyclobutyl, methyl, isopropyl, isobutyl, cyclopentylmethyl, trifluoromethyl, methylcyclopentylmethyl, methyltetrahydrofuranylmethyl, methylhydroxymethyl, hydroxymethyl, methylmethoxymethyl, pyridinylmethyl, phenyl, pyridinyl, benzyl, cyclopentenylmethyl, methylazetidinyl, imidazolylmethyl, cyclopropylmethylimidazolylmethyl, trifluoroethylimidazolylmethyl, trifluoromethylpyridinylmethyl, fluorophenylmethyl, methoxyphenylmethyl, difluoromethoxyphenylmethyl, carboxymethyl, cyanoethyl, aminocarbonylmethyl, N,N-methoxyethylaminocarbonylmethyl, hydroxycarbonylmethyl, pyrrolidinylaminocarbonylmethyl, tert-butoxycarbonylmethyl, isopropylaminocarbonylmethyl, cyclopropylmethylaminocarbonylmethyl, N,N-dimethylcarbamoyl, pyrrolidinylcarbonyl, fluoromethylpropyl, hydroxymethylpropyl, methoxymethyl, (cyclopropylmethoxy)methyl, (trimethylsilyl)methyl, phenoxymethyl, benzyloxymethyl, N,N-dimethylaminocarbonyloxymethyl, piperidinylcarbonyloxymethyl, dimethylureidomethyl, morpholinylcarbonylaminomethyl, isobutyramidomethyl, acetamidomethyl, cyclopropylacetamidomethyl, ethyloxycarbonylaminomethyl, cyclobutylcarbonylaminomethyl, methylthioethyl, methylsulfonylethyl, cyclopropylmethylthiomethyl, cyclopropylmethylsulfonylmethyl, phenylthioethyl, phenylsulfonylethyl, indolylmethyl, isopropylindolylmethyl, chlorophenylthioethyl, oxoimidazolidinylmethyl, N,S-dimethylsulfonylaminomethyl, thiophenyl, acetamidopyrrolidinylmethyl, acetylpiperazinylmethyl, oxopiperazinylmethyl, butenylmethyl, methylbutenyl, cyclopropylpropynyl, hydroxymethylpentynyl, pyridinylmethyl, methoxybenzyl, difluorobenzyl, carboxypyrrolidinylethyl, cyanobenzyl, acetamidobenzyl, N,N-dimethylaminomethylbenzyl, N,N-dimethylaminopyridinylmethyl, carbamoylbenzyl, cyclopropylsulfamoylmethyl, dimethylpiperidinylsulfonamidomethyl, benzylsulfamoylmethyl, pyridinylmethylsulfamoylmethyl, chlorophenylsulfamoylmethyl, pyrimidinylbenzyl,

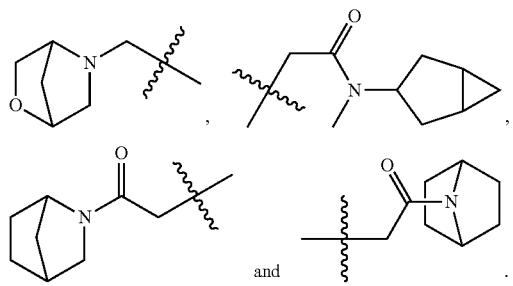

In various embodiments, $R^4$ is selected from methyl, cyclopropyl, cyclopropylmethyl, trifluoroethyl, N,N-dimethylaminoethyl, pyrrolidinylethyl, benzyl, pyridinylmethyl, ethylpyridinylmethyl, acetylpiperazinylethyl, methylsulfonamidoethyl, methoxyethyl, methoxycarbonylaminoethyl, pyrazinylaminoethyl, chlorofluorobenzyl, trifluoromethylpyridinylmethyl, imidazolylethyl, imidazolylmethyl, methyldioxopiperidinylmethyl, dioxopyrrolidinylethyl, N,N-dimethylaminocarbonylmethyl, morpholinocarbonylmethyl, hydroxymethylpropyl, fluorophenyl, and tetrahydropyranyl.

In various embodiments, $R^6$ and $R^7$ are substitutions on the phenyl ring attached to the -phenyl-C(O)—NH— linker; and $R^6$ and $R^7$ are selected to make any of the following substitutions:

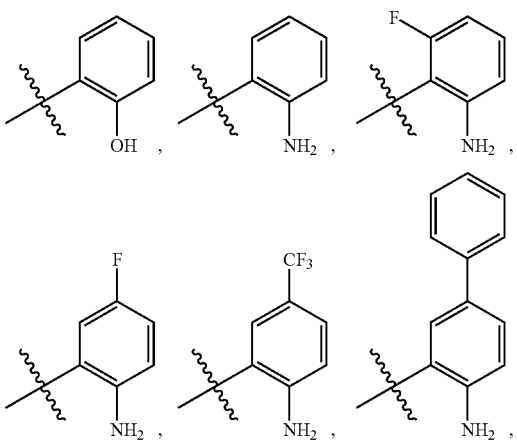

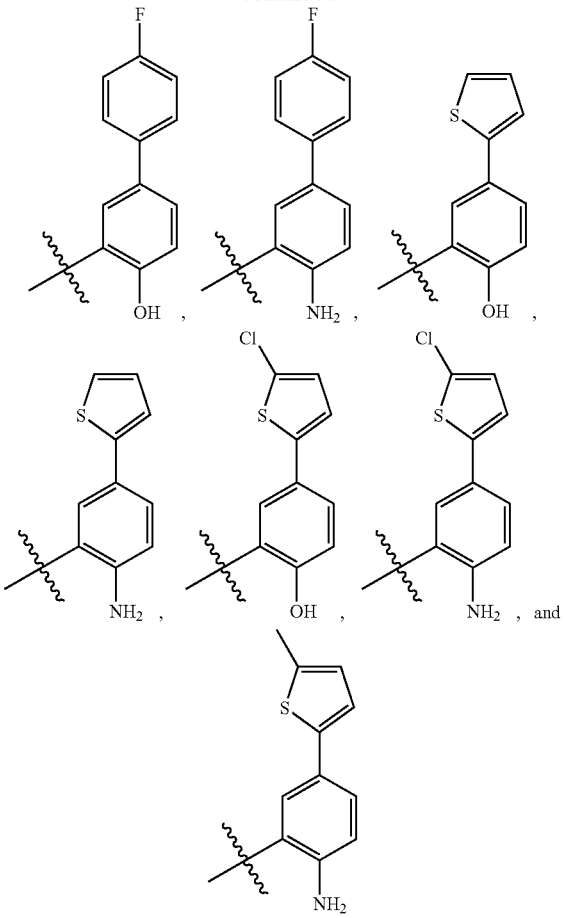

wherein the wavy line shows an attachment position to the -phenyl-C(O)—NH-linker.

In particular embodiments, compounds are selected from those of Formula (I-a) and Formula (I-b) with substituents defined as in Formula (I):

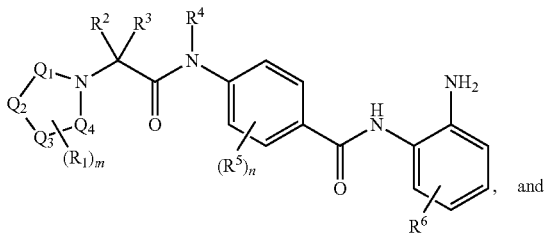

Formula (I-a)

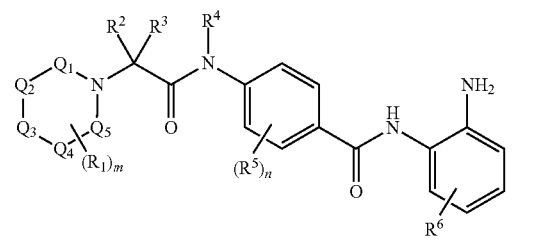

Formula (I-b)

wherein m, n, $R^1$, $R^2$, $R^3$, $R^4$, $R^5$ and $R^6$ are as defined above; and Cy is a saturated, unsaturated, or partially unsaturated ring structure containing $Q_1$, $Q_2$, $Q_3$ and $Q_4$ ring atoms, i.e., Formula (I-a) or $Q_1$, $Q_2$, $Q_3$, $Q_4$ and $Q_5$ ring atoms, i.e., Formula (I-b) which are independently selected from C, N, O and S.

Compounds defined above are useful to inhibit HDACs. In one embodiment, therefore, a compound of the invention is used in inhibiting HDAC enzymes such as, for example, mammalian HDAC. More specifically, a compound of the invention can be used to treat or inhibit HDAC-mediated diseases or abnormalities.

In an embodiment of the compounds of Formula (I), (I-a) and (I-b), one or more (including all) of the substituents $R^1$, $R^2$, $R^3$, $R^4$, $R^5$ and $R^6$ are further limited as follows:

m is 0, 1, 2, 3 or 4; and $R^1$ is selected from oxo, halo, nitro, cyano, hydroxy, hydroxyalkyl, haloalkyl, haloalkoxy, amino, azido, carboxy, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{3-8}$ cycloalkanoyl, $C_{1-10}$ alkanoyloxy, N-($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$, wherein a is 0, 1 or 2, $C_{1-10}$ alkoxycarbonyl, $NH_2$—S(O)$_2NH$—, N—($C_{1-10}$ alkyl)sulphamoyl, N,N—($C_{1-10}$ alkyl)$_2$sulphamoyl, cycloalkyl, heterocycloalkyl, aryl, heteroaryl, cycloalkylamino, heterocycloalkylamino and arylamino, wherein $R^1$ is optionally substituted by one or more A where such an optional substitution is chemically feasible;

A is independently selected from chloro, hydroxy, oxo, methyl, ethyl, propyl, methoxy, ethoxy, methoxymethyl, ethoxyethyl, propoxyethyl, methoxyethoxy, trifluoromethyl, hydroxyethoxy, N,N-dimethylamino, N,N-diethylamino, N,N-dimethylaminomethyl, N,N-diethylaminomethyl, N,N-dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-2-ylethoxy, morpholin-3-ylethoxy and morpholin-4-ylethoxy;

$R^2$ is H, alkyl, or aryl; and $R^3$ is selected from cyclobutyl, methyl, isopropyl, isobutyl, cyclopentylmethyl, trifluoromethyl, methylcyclopentylmethyl, methyltetrahydrofuranylmethyl, methylhydroxymethyl, hydroxymethyl, methylmethoxymethyl, pyridinylmethyl, phenyl, pyridinyl, benzyl, cyclopentenylmethyl, methylazetidinyl, imidazolylmethyl, cyclopropylmethylimidazolylmethyl, trifluomethylimidazolylmethyl, trifluoromethylpyridinylmethyl, fluorobenzyl, methoxybenzyl, difluoromethoxybenzyl, carboxymethyl, cyanoethyl, carbamoylmethyl, N-(methoxyethyl)carbamoylmethyl, carboxymethyl, N-(pyrrolidinyl)carbamoylmethyl, t-butanoylmethyl, N-isopropylcarbamoylmethyl, N-cyclopropylmethylcarbamoylmethyl, N,N-dimethylcarbamoyl, pyrrolidinylcarbonyl, fluoromethylpropyl, hydroxymethylpropyl, methoxymethyl, cyclopropylmethoxymethyl, trimethylsilylmethyl, phenoxymethyl, benzyloxymethyl, N,N-dimethylaminocarbonyloxymethyl, piperidinylcarbonyloxymethyl, N,N-dimethylureidomethyl, morpholinylcarbonylaminomethyl, isobutyramidomethyl, acetamidomethyl, cyclopropylacetamidomethyl, ethyloxycarbonylaminomethyl, cyclobutylcarbonylaminomethyl, methylthioethyl, methylsulfonylethyl, cyclopropylmethylthiomethyl, cyclopropylmethylsulfonylmethyl, phenylthioethyl, phenylsulfonylethyl, indolylmethyl, isopropylindolylmethyl, chlorophenylthioethyl, oxoimidazolidinylmethyl, N,S-dimethylsulfonylaminomethyl, thiophenyl, acetamidopyrrolidinylmethyl, acetylpiperazinylmethyl, oxopiperazinylmethyl, butenylmethyl, methylbutenyl, cyclopropylpropynyl, hydroxymethylpentynyl, pyridinylmethyl, methoxybenzyl, difluorobenzyl, hydroxyoxopyrrolidinylethyl, cyanobenzyl, acetamidobenzyl, N,N-dimethylaminomethylbenzyl, N,N-dimethylaminopyridinylmethyl, carbamoylbenzyl, cyclopropylsulfamoylmethyl, dimethylpiperidinesulfonamidomethyl, benzylsulfamoylmethyl, pyridinylmethylsulfamoylmethyl, chlorophenylsulfamoylmethyl, pyrimidinylbenzyl,

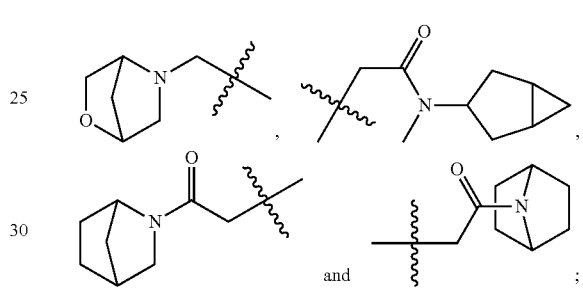

or $R^2$ is selected from methyl, methoxymethyl, and benzyl; and $R^3$ is selected from isobutyl, methoxymethyl, methoxymethyl, N,N-dimethylaminoethoxymethyl, and trifluoroethyl;

$R^4$ is selected from methyl, cyclopropyl, cyclopropylmethyl, trifluoroethyl, N,N-dimethylaminoethyl, pyrrolidinylethyl, benzyl, pyridinylmethyl, ethylpyridinylmethyl, acetylpiperazinylethyl, methylsulfonamidoethyl, methoxyethyl, methoxycarbonylaminoethyl, pyrazinylaminoethyl, chlorofluorobenzyl, trifluoromethylpyridinylmethyl, imidazolylethyl, imidazolylmethyl, (1-methyl-2,6-dioxopiperidin-4-yl)methyl, 2,5-dioxopyrrolidin-1-ylethyl, N,N-dimethylaminocarbonylmethyl, morpholinocarbonylmethyl, hydroxybutyl, fluorophenyl, and tetrahydro-2H-pyran-4-yl; and n is 0, 1, 2, 3 or 4; and $R^5$ is fluoro or haloalkyl.

In one embodiment, this disclosure provides a compound of Formula (I-a) and a pharmaceutically acceptable salt thereof:

Formula (I-a)

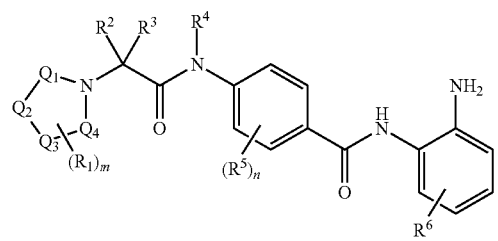

wherein $R^1$, $R^2$, $R^3$, $R^4$, $R^5$ and $R^6$ are as defined above for various aspects of Formula (I); and Cy is a saturated, unsaturated, or partially unsaturated ring structure containing $Q_1$, $Q_2$, $Q_3$ and $Q_4$ ring atoms which are independently selected from C, N, O and S.

In an embodiment of Formula (I-a), each of $Q^1$, $Q^2$, $Q^3$ and $Q^4$ is carbon ring atom, thereby having Cy being pyrrolidinyl which is optionally substituted with one or more $R^1$, wherein $R^1$ is selected from the group consisting of hydroxy, methyl, hydroxy, dialkylamino, carboxy, N,N-dialkylcarbamoyl, 5-oxo-2-(N,N-dialkyl)carbamoyl, hydroxymethyl, 1-hydroxycyclopropyl), fluoro, carboxy, and trifluoromethyl; $R^2$ is selected from H, methyl, methoxymethyl, and benzyl; and $R^3$ is selected from cyclobutyl, methyl, propyl, cyclopentylmethyl, trifluoromethyl, (1-methylcyclopent-1-yl)methyl, (3-methyltetrahydrofuran-3-yl)methyl, methylhydroxymethyl, hydroxymethyl, methylmethoxymethyl, pyridin-2-ylmethyl, phenyl, pyridin-2-yl, benzyl, cyclopentenylmethyl, 1-methylazetidin-3-yl, imidazolylmethyl, cyclopropylmethylimidazolylmethyl, (2,2,2-trifluoroethyl)imidazolylmethyl, (5-(trifluoromethyl)pyridin-2-yl)methyl, fluorobenzyl, methoxybenzyl, difluoromethoxybenzyl, carboxymethyl, cyanoethyl, carbamoylmethyl, N-(2-methoxyethyl)carbamoylmethyl, carboxymethyl, N-(pyrrolidin-3-yl)carbamoylmethyl, 2-t-butanoylmethyl, N-isopropylcarbamoylmethyl, N-cyclopropylmethylcarbamoylmethyl, N,N-dimethylcarbamoyl, pyrrolidinylcarbonyl, 2-fluoro-2-methylpropyl, 2-hydroxy-2-methylpropyl, methoxymethyl, cyclopropylmethoxymethyl, trimethylsilylmethyl, phenoxymethyl, benzyloxymethyl, N,N-dimethylaminocarbonyloxymethyl, piperidin-1-ylcarbonyloxymethyl, N,N-dimethylureidomethyl, morpholinylcarbonylaminomethyl, isobutylamidomethyl, acetamidomethyl, (2-cyclopropylacetamido)methyl, ethoxycarbonylaminomethyl, cyclobutylcarbonylaminomethyl, methylthioethyl, methylsulfonylethyl, cyclopropylmethylthiomethyl, cyclopropylmethylsulfonylmethyl, phenylthioethyl, phenylsulfonylethyl, indol-3-ylmethyl, isopropylindolylmethyl, 2-chlorophenylthioethyl, 2-oxoimidazolidin-1-ylmethyl, N,S-dimethylsulfonylaminomethyl, thiophen-2-yl, (3-acetamidopyrrolidin-1-yl)methyl, (4-acetylpiperazin-1-yl)methyl, (3-oxopiperazin-1-yl)methyl, but-2-enylmethyl, 2-methylbut-2-enyl, 3-cyclopropylprop-2-ynyl, 4-hydroxy-4-methylpent-2-ynyl, pyridin-2-ylmethyl, 4-methoxybenzyl, 2,3-difluorobenzyl, 1-hydroxy-2-oxo-2-(pyrrolidin-1-yl) ethyl, 2-cyanobenzyl, 4-acetamidobenzyl, 4-((N,N-dimethylamino)methyl)benzyl, (6-(N,N-dimethylamino)pyridin-3-yl)methyl, 4-carbamoylbenzyl, cyclopropylsulfamoylmethyl, (4,4-dimethylpiperidine-1-sulfonamido)methyl, benzylsulfamoylmethyl, ((pyridin-2-ylmethyl)sulfamoyl)methyl, ((4-chlorophenyl)sulfamoyl) methyl, and 4-(pyrimidin-2-yl)benzyl; $R^4$ is independently selected from the group consisting of methyl, cyclopropyl, cyclopropylmethyl, trifluoroethyl, N,N-dimethylaminoethyl, pyrzolidin-1-ylethyl, benzyl, pyridin-2-ylmethyl, (1-ethylpyridin-4-yl)methyl, (4-acetylpiperazin-1-yl)ethyl, methylsulfonamidoethyl, methoxyethyl, methoxycarbonylaminoethyl, (pyrazin-2-ylamino)ethyl, 2-chloro-4-fluorobenzyl, (5-(trifluoromethyl)pyridin-2-yl)methyl, imidazolylethyl, imidazolylmethyl, (1-methyl-2,6-dioxopiperidin-4-yl)methyl, 2,5-dioxopyrrolidin-1-ylethyl, (N,N-dimethylamino) carbonylmethyl, morpholinocarbonylmethyl, 2-hydroxy-2-methylpropyl, 4-fluorophenyl, tetrahydro-2H-pyran-4-yl,

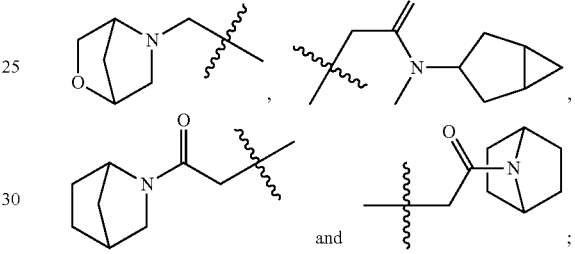
and n is 0, 1 or 2 and $R^5$ is independently selected from halo, hydroxy, alkyl and haloalkyl; and $R^6$ is selected from fluoro, trifluoromethyl, phenyl, fluorophenyl, thiophenyl, chlorothiophenyl, and methylthiophenyl.

Non-limiting examples of such compounds include compounds of Formula (I-a1) and pharmaceutically acceptable salts thereof:

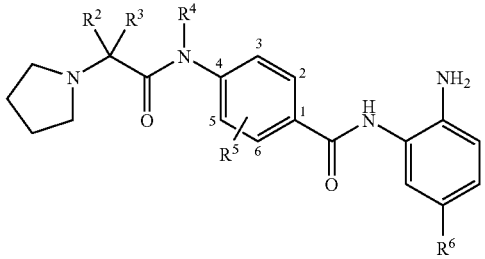

Formula (I-a1)

| Comp. No. | $R^2$ | $R^3$ | $R^4$ | $R^5$ | $R^6$ |
|---|---|---|---|---|---|
| a1-1 | H | —CH₃ | H | H | H |
| a1-2 | H | —CH₃ | —CH₃ | H | H |
| a1-3 | H | —CH₃ | H | —F (position 3) | H |
| a1-4 | H | —CH₃ | —CH₃ | —F (position 3) | H |
| a1-5 | H | —CH₃ | H | H | 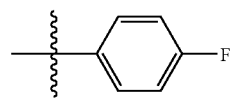 |

Formula (I-a1)
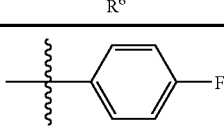
| Comp. No. | R² | R³ | R⁴ | R⁵ | R⁶ |
|---|---|---|---|---|---|
| a1-6 | H | —CH₃ | —CH₃ | H | 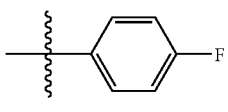 4-F-phenyl |
| a1-7 | H | —CH₃ | H | —F (position 3) | 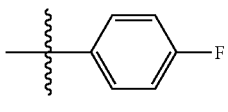 4-F-phenyl |
| a1-8 | H | —CH₃ | —CH₃ | —F (position 3) | 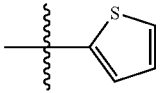 4-F-phenyl |
| a1-9 | H | —CH₃ | H | H | 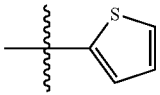 thiophen-2-yl |
| a1-10 | H | —CH₃ | —CH₃ | H | 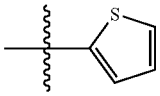 thiophen-2-yl |
| a1-11 | H | —CH₃ | H | —F (position 3) | 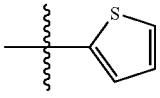 thiophen-2-yl |
| a1-12 | H | —CH₃ | —CH₃ | —F (position 3) | 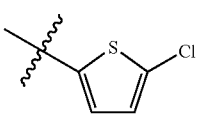 thiophen-2-yl |
| a1-13 | H | —CH₃ | H | H | 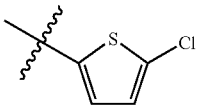 5-Cl-thiophen-2-yl |
| a1-14 | H | —CH₃ | —CH₃ | H | 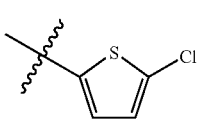 5-Cl-thiophen-2-yl |
| a1-15 | H | —CH₃ | H | —F (position 3) | 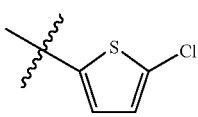 5-Cl-thiophen-2-yl |
| a1-16 | H | —CH₃ | —CH₃ | —F (position 3) | 5-Cl-thiophen-2-yl |
| a1-17 | H | phenyl | H | H | H |

-continued

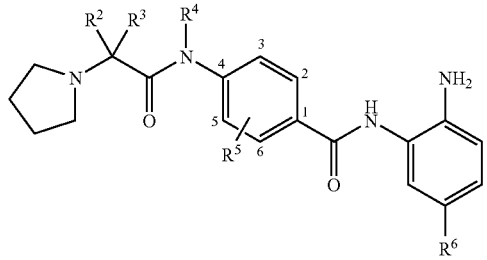

Formula (I-a1)

| Comp. No. | R² | R³ | R⁴ | R⁵ | R⁶ |
|---|---|---|---|---|---|
| a1-18 | H | phenyl | —CH₃ | H | H |
| a1-19 | H | phenyl | H | —F (position 3) | H |
| a1-20 | H | phenyl | —CH₃ | —F (position 3) | H |
| a1-21 | H | phenyl | H | H | 4-fluorophenyl |
| a1-22 | H | phenyl | —CH₃ | H | 4-fluorophenyl |
| a1-23 | H | phenyl | H | —F (position 3) | 4-fluorophenyl |
| a1-24 | H | phenyl | —CH₃ | —F (position 3) | 4-fluorophenyl |
| a1-25 | H | phenyl | H | H | 2-thienyl |
| a1-26 | H | phenyl | —CH₃ | H | 2-thienyl |
| a1-27 | H | phenyl | H | —F (position 3) | 2-thienyl |
| a1-28 | H | phenyl | —CH₃ | —F (position 3) | 2-thienyl |
| a1-29 | H | phenyl | H | H | 5-chloro-2-thienyl |
| a1-30 | H | phenyl | —CH₃ | H | 5-chloro-2-thienyl |

-continued
Formula (I-a1)
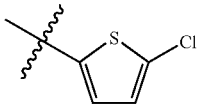
| Comp. No. | R² | R³ | R⁴ | R⁵ | R⁶ |
|---|---|---|---|---|---|
| a1-31 | H | phenyl | H | —F (position 3) | 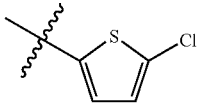 |
| a1-32 | H | phenyl | —CH₃ | —F (position 3) | 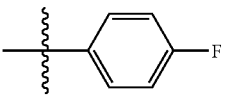 |
| a1-33 | —CH₃ | —CH₃ | H | H | H |
| a1-34 | —CH₃ | —CH₃ | —CH₃ | H | H |
| a1-35 | —CH₃ | —CH₃ | H | —F (position 3) | H |
| a1-36 | —CH₃ | —CH₃ | —CH₃ | —F (position 3) | H |
| a1-37 | —CH₃ | —CH₃ | H | H | 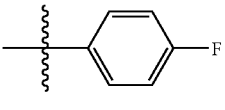 |
| a1-38 | —CH₃ | —CH₃ | —CH₃ | H | 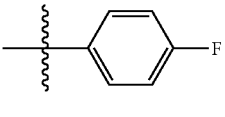 |
| a1-39 | —CH₃ | —CH₃ | H | —F (position 3) | 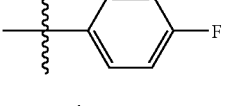 |
| a1-40 | —CH₃ | —CH₃ | —CH₃ | —F (position 3) | 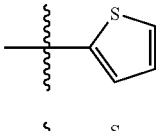 |
| a1-41 | —CH₃ | —CH₃ | H | H | 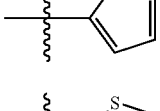 |
| a1-42 | —CH₃ | —CH₃ | —CH₃ | H | 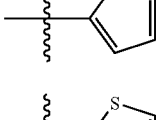 |
| a1-43 | —CH₃ | —CH₃ | H | —F (position 3) | 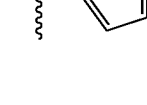 |
| a1-44 | —CH₃ | —CH₃ | —CH₃ | —F (position 3) | 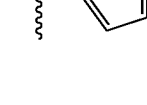 |

Formula (I-a1)

| Comp. No. | R² | R³ | R⁴ | R⁵ | R⁶ |
|---|---|---|---|---|---|
| a1-45 | —CH₃ | —CH₃ | H | H | 5-chlorothien-2-yl |
| a1-46 | —CH₃ | —CH₃ | —CH₃ | H | 5-chlorothien-2-yl |
| a1-47 | —CH₃ | —CH₃ | H | —F (position 3) | 5-chlorothien-2-yl |
| a1-48 | —CH₃ | —CH₃ | —CH₃ | —F (position 3) | 5-chlorothien-2-yl |

In an embodiment of Formula (I-a), each of $Q^1$, $Q^3$ and $Q^4$ is carbon ring atom and $Q^2$ is carbon ring atom substituted with oxo, thereby having Cy being oxopyrrolidinyl which is optionally substituted with one or more $R^1$, wherein $R^1$ is selected from the group consisting of hydroxy, methyl, oxo, hydroxy, dialkylamino, carboxy, N,N-dialkylcarbamoyl, hydroxymethyl, hydroxycyclopropyl, 3-fluoro, 2-methyl-2-carboxy, trifluoromethyl, and carboxy; and $R^2$, $R^3$, $R^4$, $R^5$ and $R^6$ are as defined above for various aspects of Formula (I-a).

Non-limiting examples of such compounds include compounds of Formula (I-a2) and pharmaceutically acceptable salts thereof:

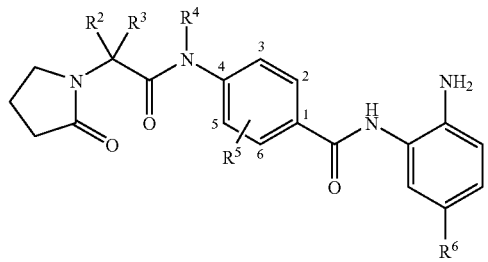

Formula (I-a2)

| Comp. No. | R² | R³ | R⁴ | R⁵ | R⁶ |
|---|---|---|---|---|---|
| a2-1 | H | —CH₃ | H | H | H |
| a2-2 | H | —CH₃ | —CH₃ | H | H |
| a2-3 | H | —CH₃ | H | —F (position 3) | H |
| a2-4 | H | —CH₃ | —CH₃ | —F (position 3) | H |

-continued
Formula (I-a2)
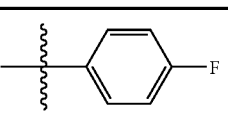
| Comp. No. | R² | R³ | R⁴ | R⁵ | R⁶ |
|---|---|---|---|---|---|
| a2-5 | H | —CH₃ | H | H | 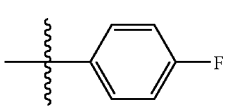 4-F-phenyl |
| a2-6 | H | —CH₃ | —CH₃ | H | 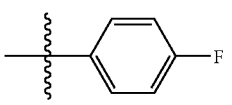 4-F-phenyl |
| a2-7 | H | —CH₃ | H | —F (position 3) | 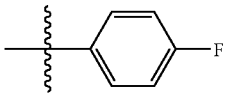 4-F-phenyl |
| a2-8 | H | —CH₃ | —CH₃ | —F (position 3) | 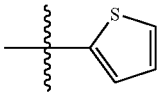 4-F-phenyl |
| a2-9 | H | —CH₃ | H | H | 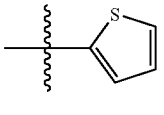 thiophene |
| a2-10 | H | —CH₃ | —CH₃ | H | 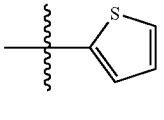 thiophene |
| a2-11 | H | —CH₃ | H | —F (position 3) | 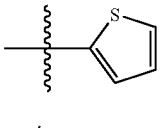 thiophene |
| a2-12 | H | —CH₃ | —CH₃ | —F (position 3) | 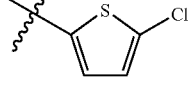 thiophene |
| a2-13 | H | —CH₃ | H | H | 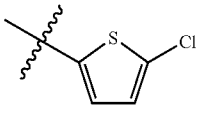 5-Cl-thiophene |
| a2-14 | H | —CH₃ | —CH₃ | H | 5-Cl-thiophene |
| a2-15 | H | —CH₃ | H | —F (position 3) | 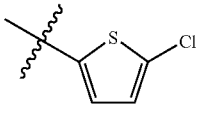 5-Cl-thiophene |

-continued
Formula (I-a2)
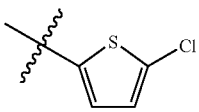
| Comp. No. | R² | R³ | R⁴ | R⁵ | R⁶ |
|---|---|---|---|---|---|
| a2-16 | H | —CH₃ | —CH₃ | —F (position 3) | 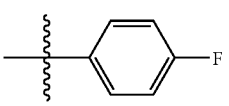 |
| a2-17 | H | phenyl | H | H | H |
| a2-18 | H | phenyl | —CH₃ | H | H |
| a2-19 | H | phenyl | H | —F (position 3) | H |
| a2-20 | H | phenyl | —CH₃ | —F (position 3) | H |
| a2-21 | H | phenyl | H | H | 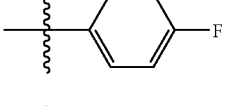 |
| a2-22 | H | phenyl | —CH₃ | H |  |
| a2-23 | H | phenyl | H | —F (position 3) | 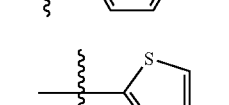 |
| a2-24 | H | phenyl | —CH₃ | —F (position 3) | 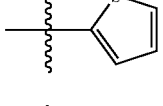 |
| a2-25 | H | phenyl | H | H | 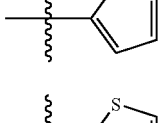 |
| a2-26 | H | phenyl | —CH₃ | H | 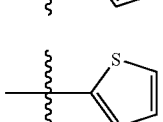 |
| a2-27 | H | phenyl | H | —F (position 3) | 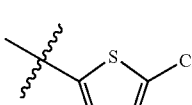 |
| a2-28 | H | phenyl | —CH₃ | —F (position 3) | 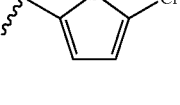 |
| a2-29 | H | phenyl | H | H |  |

-continued

Formula (I-a2)

| Comp. No. | R² | R³ | R⁴ | R⁵ | R⁶ |
|---|---|---|---|---|---|
| a2-30 | H | phenyl | —CH₃ | H | 5-chlorothiophen-2-yl |
| a2-31 | H | phenyl | H | —F (position 3) | 5-chlorothiophen-2-yl |
| a2-32 | H | phenyl | —CH₃ | —F (position 3) | 5-chlorothiophen-2-yl |
| a2-33 | —CH₃ | —CH₃ | H | H | H |
| a2-34 | —CH₃ | —CH₃ | —CH₃ | H | H |
| a2-35 | —CH₃ | —CH₃ | H | —F (position 3) | H |
| a2-36 | —CH₃ | —CH₃ | —CH₃ | —F (position 3) | H |
| a2-37 | —CH₃ | —CH₃ | H | H | 4-fluorophenyl |
| a2-38 | —CH₃ | —CH₃ | —CH₃ | H | 4-fluorophenyl |
| a2-39 | —CH₃ | —CH₃ | H | —F (position 3) | 4-fluorophenyl |
| a2-40 | —CH₃ | —CH₃ | —CH₃ | —F (position 3) | 4-fluorophenyl |
| a2-41 | —CH₃ | —CH₃ | H | H | thiophen-2-yl |
| a2-42 | —CH₃ | —CH₃ | —CH₃ | H | thiophen-2-yl |
| a2-43 | —CH₃ | —CH₃ | H | —F (position 3) | thiophen-2-yl |

-continued

Formula (I-a2)

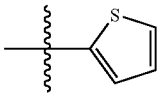

| Comp. No. | R² | R³ | R⁴ | R⁵ | R⁶ |
|---|---|---|---|---|---|
| a2-44 | —CH₃ | —CH₃ | —CH₃ | —F (position 3) | 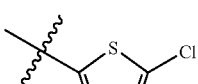 |
| a2-45 | —CH₃ | —CH₃ | H | H | 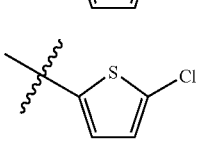 |
| a2-46 | —CH₃ | —CH₃ | —CH₃ | H | 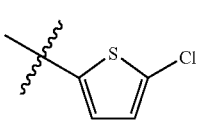 |
| a2-47 | —CH₃ | —CH₃ | H | —F (position 3) | 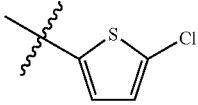 |
| a2-48 | —CH₃ | —CH₃ | —CH₃ | —F (position 3) | 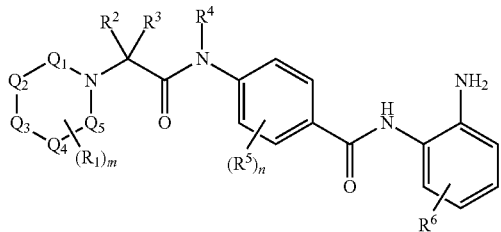 |

In one embodiment, the invention provides a compound of Formula (I-b) and a pharmaceutically acceptable salt thereof:

Formula (I-b)

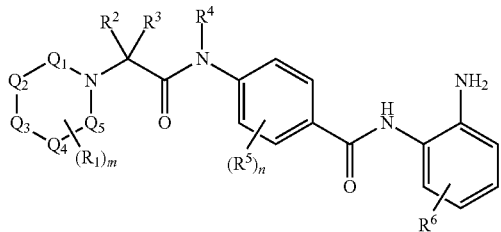

wherein m, n, $R^1$, $R^2$, $R^3$, $R^4$, $R^5$ and $R^6$ are as defined above for various aspects of Formula (I); and Cy is a saturated, unsaturated, or partially unsaturated ring structure containing $Q_1$, $Q_2$, $Q_3$, $Q_4$ and $Q_5$ ring atoms which are independently selected from C, N, O and S.

In an embodiment of Formula (I-b), each of $Q^1$, $Q^2$, $Q^4$ and $Q^5$ is carbon ring atom and $Q^3$ is oxygen ring atom, thereby having Cy being morpholinyl which is optionally substituted with one or more $R^1$, wherein $R^1$ is selected from methyl, methylcyclopropyl, trifluoroethyl, methoxypropyl, N,N-dimethylaminopropyl, carboxycyclopropyl, N,N-dimethylcarbamoylcyclopropyl, pyridinylmethyl, trifluoromethylpyridinylmethyl, N,N-dimethylcarbamoyl, morpholinocarbonyl, t-butylcarbamoyl, morpholinoethoxycarbonyl, benzoyl, picolinoyl, quinoxalinylcarbonyl, cyclopropylcarbonyl, propionyl, methoxypropanoyl, N,N-dimethylaminopropanoyl, trifluoromethylpyridinyl, chloropyridinyl, cyclopropylpyridinyl, chloropyrimidinyl, methoxyphenyl, carboxyphenyl, N,N-dimethylcarbamoylphenyl, chlorophenyl, bicyclo[3.1.0]hexanoxycarbonyl, methylcyclopropoxycarbonyl, t-butoxycarbonyl, tritluoromethylpropoxycarbonyl, methylsulfonyl, trifluoroethylsulfonyl, trifluoromethylpyridinylsulfonyl, pyridinylsulfonyl, phenylsulfonyl, cyclopropylsulfonyl, pyridinyl, trifluoromethylpyridinyl, phenyl, cyclopropyl, hydroxypropyl, trifluoromethyl, hydroxycyclopropyl, trifluoroethylamino, oxo, diazepanyl, acetamido, methylcyclopropylamino, cyano, carboxymethyl, N,N-dimethylcarbamoylmethyl, pyridinyl, trifluoromethylpyridinyl, N,N-dimethylcarbamoyl, aminomethyl, hydroxy, cyclobutyl, carboxy, alkylpiperidinyl, and cyclobutylamino; and $R^2$, $R^3$, $R^4$, $R^5$ and $R^6$ are as defined above for various aspects of Formula (I-a).

Non-limiting examples of such compounds include compounds of Formula (I-b1) and pharmaceutically acceptable salts thereof:

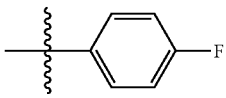
Formula (I-b1)
| Comp. No. | R² | R³ | R⁴ | R⁵ | R⁶ |
|---|---|---|---|---|---|
| b1-1 | H | —CH₃ | H | H | H |
| b1-2 | H | —CH₃ | —CH₃ | H | H |
| b1-3 | H | —CH₃ | H | —F (position 3) | H |
| b1-4 | H | —CH₃ | —CH₃ | —F (position 3) | H |
| b1-5 | H | —CH₃ | H | H | 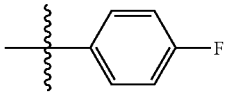 |
| b1-6 | H | —CH₃ | —CH₃ | H | 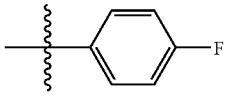 |
| b1-7 | H | —CH₃ | H | —F (position 3) | 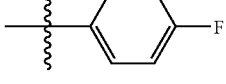 |
| b1-8 | H | —CH₃ | —CH₃ | —F (position 3) | 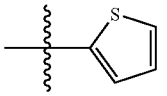 |
| b1-9 | H | —CH₃ | H | H | 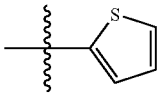 |
| b1-10 | H | —CH₃ | —CH₃ | H | 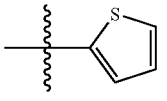 |
| b1-11 | H | —CH₃ | H | —F (position 3) | 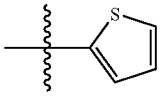 |
| b1-12 | H | —CH₃ | —CH₃ | —F (position 3) | 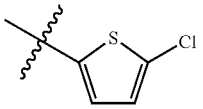 |
| b1-13 | H | —CH₃ | H | H | 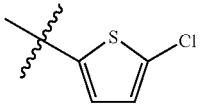 |
| b1-14 | H | —CH₃ | —CH₃ | H |  |

-continued

Formula (I-b1)

| Comp. No. | R² | R³ | R⁴ | R⁵ | R⁶ |
|---|---|---|---|---|---|
| b1-15 | H | —CH₃ | H | —F (position 3) | 5-chloro-thiophen-2-yl |
| b1-16 | H | —CH₃ | —CH₃ | —F (position 3) | 5-chloro-thiophen-2-yl |
| b1-17 | H | phenyl | H | H | H |
| b1-18 | H | phenyl | —CH₃ | H | H |
| b1-19 | H | phenyl | H | —F (position 3) | H |
| b1-20 | H | phenyl | —CH₃ | —F (position 3) | H |
| b1-21 | H | phenyl | H | H | 4-fluoro-phenyl |
| b1-22 | H | phenyl | —CH₃ | H | 4-fluoro-phenyl |
| b1-23 | H | phenyl | H | —F (position 3) | 4-fluoro-phenyl |
| b1-24 | H | phenyl | —CH₃ | —F (position 3) | 4-fluoro-phenyl |
| b1-25 | H | phenyl | H | H | thiophen-2-yl |
| b1-26 | H | phenyl | —CH₃ | H | thiophen-2-yl |
| b1-27 | H | phenyl | H | —F (position 3) | thiophen-2-yl |
| b1-28 | H | phenyl | —CH₃ | —F (position 3) | thiophen-2-yl |

-continued

Formula (I-b1)

| Comp. No. | R² | R³ | R⁴ | R⁵ | R⁶ |
|---|---|---|---|---|---|
| b1-29 | H | phenyl | H | H | 5-chlorothiophen-2-yl |
| b1-30 | H | phenyl | —CH₃ | H | 5-chlorothiophen-2-yl |
| b1-31 | H | phenyl | H | —F (position 3) | 5-chlorothiophen-2-yl |
| b1-32 | H | phenyl | —CH₃ | —F (position 3) | 5-chlorothiophen-2-yl |
| b1-33 | —CH₃ | —CH₃ | H | H | H |
| b1-34 | —CH₃ | —CH₃ | —CH₃ | H | H |
| b1-35 | —CH₃ | —CH₃ | H | —F (position 3) | H |
| b1-36 | —CH₃ | —CH₃ | —CH₃ | —F (position 3) | H |
| b1-37 | —CH₃ | —CH₃ | H | H | 4-fluorophenyl |
| b1-38 | —CH₃ | —CH₃ | —CH₃ | H | 4-fluorophenyl |
| b1-39 | —CH₃ | —CH₃ | H | —F (position 3) | 4-fluorophenyl |
| b1-40 | —CH₃ | —CH₃ | —CH₃ | —F (position 3) | 4-fluorophenyl |
| b1-41 | —CH₃ | —CH₃ | H | H | thiophen-2-yl |

-continued
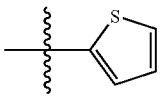
Formula (I-b1)
| Comp. No. | R² | R³ | R⁴ | R⁵ | R⁶ |
|---|---|---|---|---|---|
| b1-42 | —CH₃ | —CH₃ | —CH₃ | H | 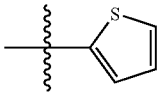 |
| b1-43 | —CH₃ | —CH₃ | H | —F (position 3) | 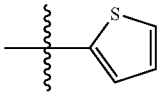 |
| b1-44 | —CH₃ | —CH₃ | —CH₃ | —F (position 3) |  |
| b1-45 | —CH₃ | —CH₃ | H | H | 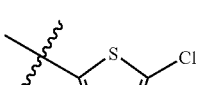 |
| b1-46 | —CH₃ | —CH₃ | —CH₃ | H | 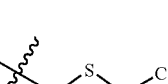 |
| b1-47 | —CH₃ | —CH₃ | H | —F (position 3) | 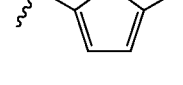 |
| b1-48 | —CH₃ | —CH₃ | —CH₃ | —F (position 3) | 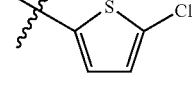 |

In an embodiment of Formula (I-b), each of $Q^1$, $Q^2$, $Q^3$, $Q^4$ and $Q^5$ is carbon ring atom, or each of $Q^1$, $Q^2$, $Q^4$ and $Q^5$ is carbon ring atom and $Q^3$ is nitrogen ring atom, thereby having Cy being piperidinyl or piperazinyl which is optionally substituted with one or more $R^1$; and $R^1$, $R^2$, $R^3$, $R^4$, $R^5$ and $R^6$ are as defined above for various aspects of Formula (I-b).

Non-limiting examples of such compounds include compounds of Formulae (I-b2) and (I-b3) and pharmaceutically accepted salts thereof:

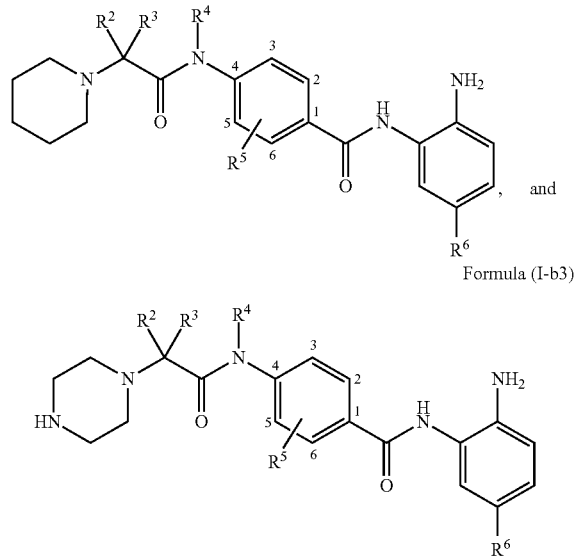

Formula (I-b2)

Formula (I-b3)

wherein $R^2$, $R^3$, $R^4$, $R^5$ and $R^6$ can be selected to have the same combination of substituents given in the table for Compounds I-b1-01 to I-b1-48.

In yet another embodiment, there is provided a compound selected from those of Formula (II) and pharmaceutically accepted salts thereof:

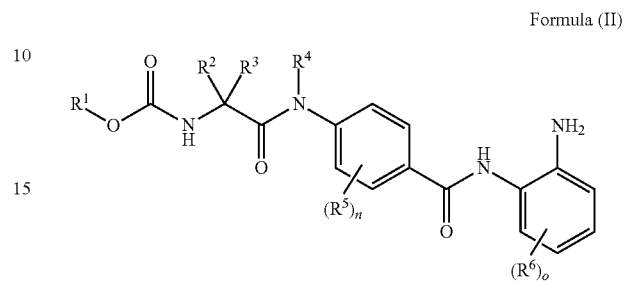

Formula (II)

wherein $R^1$ is selected from the group consisting of alkyl, aryl, aralkyl, cycloalkyl, heterocyclyl, cycloalkylalkyl, alkylcycloalkyl, haloalkyl, heteroarylalkyl, haloalkylheteroaryl, and cycloalkylheteroaryl wherein $R^1$ is optionally substituted with alkyl; and $R^2$, $R^3$, $R^4$, $R^5$, $R^6$, $R^7$, n and o are as defined above for various aspects of Formula (I).

In a particular embodiment of Formula (II), $R^1$ is selected from the group consisting of phenylalkyl, bicyclo[3.1.0]hexanyl, 1-methylcyclopropyl, t-butyl, 1,1,1-trifluoro-2-methylprop-2-oxycarbonyl, benzoxycarbonyl, pyridin-3-ylmethyl, 5-trifluoromethylpyridin-3-ylmethyl, 5-cyclopropylpyridin-3-ylmethyl, 1-phenylethyl, quinolin-3-ylmethyl, and 2-morpholinoethyl; $R^2$, $R^3$, $R^4$, $R^5$, $R^6$, and $R^7$ are as defined above for various aspects of Formula (I-a).

In an embodiment, $R^1$ is t-butyl. Non-limiting examples of such compounds include compounds of Formula (II-c1) and pharmaceutically acceptable salts thereof:

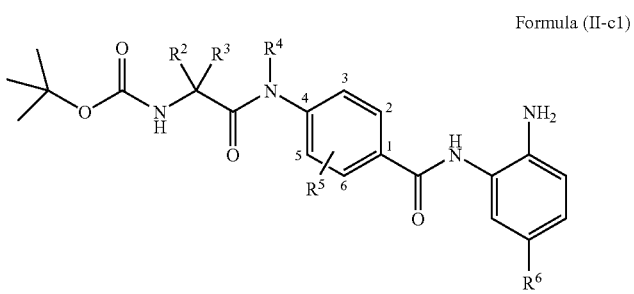

Formula (II-c1)

| Comp. No. | $R^2$ | $R^3$ | $R^4$ | $R^5$ | $R^6$ |
|---|---|---|---|---|---|
| c1-1 | H | —CH₃ | H | H | H |
| c1-2 | H | —CH₃ | —CH₃ | H | H |
| c1-3 | H | —CH₃ | H | —F (position 3) | H |
| c1-4 | H | —CH₃ | —CH₃ | —F (position 3) | H |
| c1-5 | H | —CH₃ | H | H | ![4-F-phenyl] |
| c1-6 | H | —CH₃ | —CH₃ | H | ![4-F-phenyl] |

-continued
Formula (II-c1)
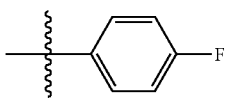
| Comp. No. | R² | R³ | R⁴ | R⁵ | R⁶ |
|---|---|---|---|---|---|
| c1-7 | H | —CH₃ | H | —F (position 3) | 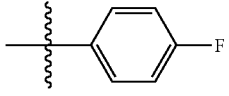 |
| c1-8 | H | —CH₃ | —CH₃ | —F (position 3) | 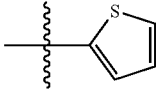 |
| c1-9 | H | —CH₃ | H | H | 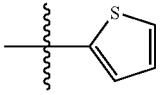 |
| c1-10 | H | —CH₃ | —CH₃ | H | 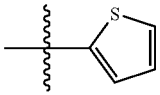 |
| c1-11 | H | —CH₃ | H | —F (position 3) | 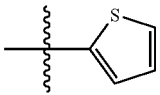 |
| c1-12 | H | —CH₃ | —CH₃ | —F (position 3) | 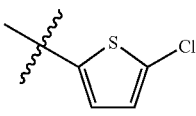 |
| c1-13 | H | —CH₃ | H | H | 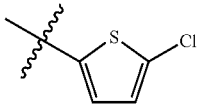 |
| c1-14 | H | —CH₃ | —CH₃ | H | 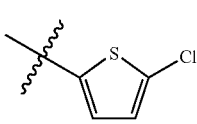 |
| c1-15 | H | —CH₃ | H | —F (position 3) | 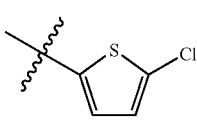 |
| c1-16 | H | —CH₃ | —CH₃ | —F (position 3) | |
| c1-17 | H | phenyl | H | H | H |
| c1-18 | H | phenyl | —CH₃ | H | H |
| c1-19 | H | phenyl | H | —F (position 3) | H |
| c1-20 | H | phenyl | —CH₃ | —F (position 3) | H |

-continued

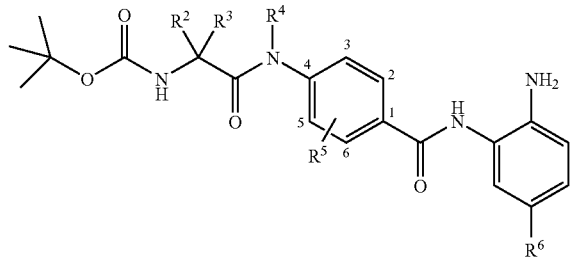

Formula (II-c1)

| Comp. No. | R² | R³ | R⁴ | R⁵ | R⁶ |
|---|---|---|---|---|---|
| c1-21 | H | phenyl | H | H | 4-fluorophenyl |
| c1-22 | H | phenyl | —CH₃ | H | 4-fluorophenyl |
| c1-23 | H | phenyl | H | —F (position 3) | 4-fluorophenyl |
| c1-24 | H | phenyl | —CH₃ | —F (position 3) | 4-fluorophenyl |
| c1-25 | H | phenyl | H | H | thiophen-2-yl |
| c1-26 | H | phenyl | —CH₃ | H | thiophen-2-yl |
| c1-27 | H | phenyl | H | —F (position 3) | thiophen-2-yl |
| c1-28 | H | phenyl | —CH₃ | —F (position 3) | thiophen-2-yl |
| c1-29 | H | phenyl | H | H | 5-chlorothiophen-2-yl |
| c1-30 | H | phenyl | —CH₃ | H | 5-chlorothiophen-2-yl |
| c1-31 | H | phenyl | H | —F (position 3) | 5-chlorothiophen-2-yl |

-continued

Formula (II-c1)

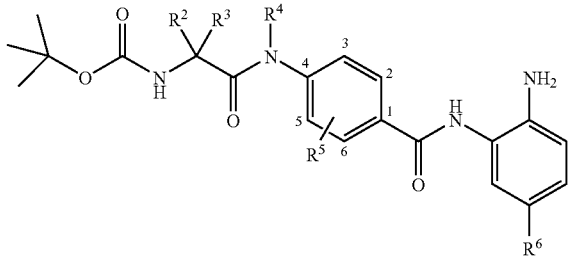

| Comp. No. | R² | R³ | R⁴ | R⁵ | R⁶ |
|---|---|---|---|---|---|
| c1-32 | H | phenyl | —CH₃ | —F (position 3) | 5-chlorothien-2-yl |
| c1-33 | —CH₃ | —CH₃ | H | H | H |
| c1-34 | —CH₃ | —CH₃ | —CH₃ | H | H |
| c1-35 | —CH₃ | —CH₃ | H | —F (position 3) | H |
| c1-36 | —CH₃ | —CH₃ | —CH₃ | —F (position 3) | H |
| c1-37 | —CH₃ | —CH₃ | H | H | 4-fluorophenyl |
| c1-38 | —CH₃ | —CH₃ | —CH₃ | H | 4-fluorophenyl |
| c1-39 | —CH₃ | —CH₃ | H | —F (position 3) | 4-fluorophenyl |
| c1-40 | —CH₃ | —CH₃ | —CH₃ | —F (position 3) | 4-fluorophenyl |
| c1-41 | —CH₃ | —CH₃ | H | H | thien-2-yl |
| c1-42 | —CH₃ | —CH₃ | —CH₃ | H | thien-2-yl |
| c1-43 | —CH₃ | —CH₃ | H | —F (position 3) | thien-2-yl |
| c1-44 | —CH₃ | —CH₃ | —CH₃ | —F (position 3) | thien-2-yl |
| c1-45 | —CH₃ | —CH₃ | H | H | 5-chlorothien-2-yl |

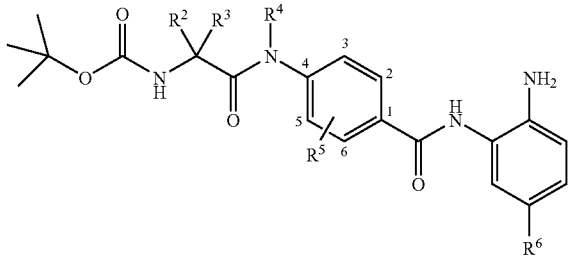

Formula (II-c1)

| Comp. No. | R² | R³ | R⁴ | R⁵ | R⁶ |
|---|---|---|---|---|---|
| c1-46 | —CH₃ | —CH₃ | —CH₃ | H | thiophene-Cl |
| c1-47 | —CH₃ | —CH₃ | H | —F (position 3) | thiophene-Cl |
| c1-48 | —CH₃ | —CH₃ | —CH₃ | —F (position 3) | thiophene-Cl |

In an embodiment of Formula (II), $R^1$ is phenylalkyl such as benzyl and phenylethyl; $R^2$, $R^3$, $R^4$, $R^5$ and $R^6$ are as defined above for various aspects of Formula (I-a).

Non-limiting examples of such compounds include compounds of Formula (II-c2) and pharmaceutically acceptable salts thereof:

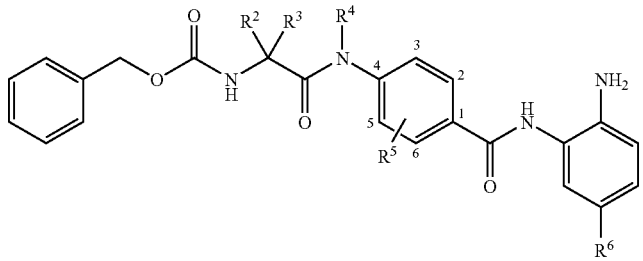

Formula (II-c2)

| Comp. No. | R² | R³ | R⁴ | R⁵ | R⁶ |
|---|---|---|---|---|---|
| c2-1 | H | —CH₃ | H | H | H |
| c2-2 | H | —CH₃ | —CH₃ | H | H |
| c2-3 | H | —CH₃ | H | —F (position 3) | H |
| c2-4 | H | —CH₃ | —CH₃ | —F (position 3) | H |
| c2-5 | H | —CH₃ | H | H | phenyl-F |
| c2-6 | H | —CH₃ | —CH₃ | H | phenyl-F |

-continued

Formula (II-c2)

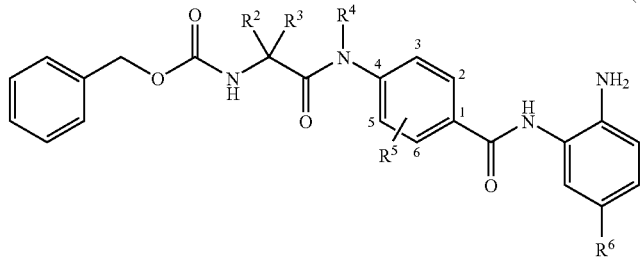

| Comp. No. | R² | R³ | R⁴ | R⁵ | R⁶ |
|---|---|---|---|---|---|
| c2-7 | H | —CH₃ | H | —F (position 3) | 4-fluorophenyl |
| c2-8 | H | —CH₃ | —CH₃ | —F (position 3) | 4-fluorophenyl |
| c2-9 | H | —CH₃ | H | H | 2-thienyl |
| c2-10 | H | —CH₃ | —CH₃ | H | 2-thienyl |
| c2-11 | H | —CH₃ | H | —F (position 3) | 2-thienyl |
| c2-12 | H | —CH₃ | —CH₃ | —F (position 3) | 2-thienyl |
| c2-13 | H | —CH₃ | H | H | 5-chloro-2-thienyl |
| c2-14 | H | —CH₃ | —CH₃ | H | 5-chloro-2-thienyl |
| c2-15 | H | —CH₃ | H | —F (position 3) | 5-chloro-2-thienyl |
| c2-16 | H | —CH₃ | —CH₃ | —F (position 3) | 5-chloro-2-thienyl |
| c2-17 | H | phenyl | H | H | H |
| c2-18 | H | phenyl | —CH₃ | H | H |
| c2-19 | H | phenyl | H | —F (position 3) | H |
| c2-20 | H | phenyl | —CH₃ | —F (position 3) | H |

-continued

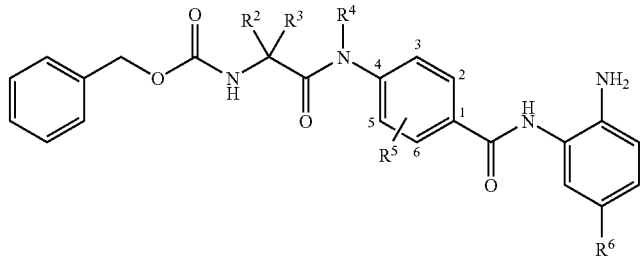

Formula (II-c2)

| Comp. No. | R² | R³ | R⁴ | R⁵ | R⁶ |
|---|---|---|---|---|---|
| c2-21 | H | phenyl | H | H | 4-fluorophenyl |
| c2-22 | H | phenyl | —CH₃ | H | 4-fluorophenyl |
| c2-23 | H | phenyl | H | —F (position 3) | 4-fluorophenyl |
| c2-24 | H | phenyl | —CH₃ | —F (position 3) | 4-fluorophenyl |
| c2-25 | H | phenyl | H | H | thiophen-2-yl |
| c2-26 | H | phenyl | —CH₃ | H | thiophen-2-yl |
| c2-27 | H | phenyl | H | —F (position 3) | thiophen-2-yl |
| c2-28 | H | phenyl | —CH₃ | —F (position 3) | thiophen-2-yl |
| c2-29 | H | phenyl | H | H | 5-chlorothiophen-2-yl |
| c2-30 | H | phenyl | —CH₃ | H | 5-chlorothiophen-2-yl |
| c2-31 | H | phenyl | H | —F (position 3) | 5-chlorothiophen-2-yl |

-continued

Formula (II-c2)

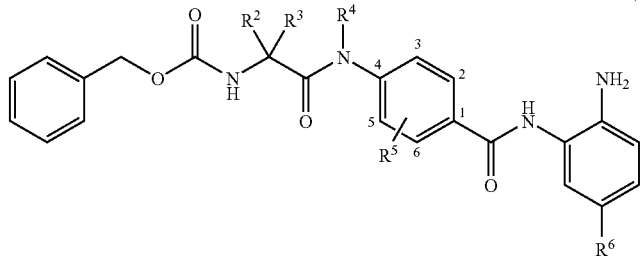

| Comp. No. | R² | R³ | R⁴ | R⁵ | R⁶ |
|---|---|---|---|---|---|
| c2-32 | H | phenyl | —CH₃ | —F (position 3) | ![thiophene-Cl] |
| c2-33 | —CH₃ | —CH₃ | H | H | H |
| c2-34 | —CH₃ | —CH₃ | —CH₃ | H | H |
| c2-35 | —CH₃ | —CH₃ | H | —F (position 3) | H |
| c2-36 | —CH₃ | —CH₃ | —CH₃ | —F (position 3) | H |
| c2-37 | —CH₃ | —CH₃ | H | H | 4-F-phenyl |
| c2-38 | —CH₃ | —CH₃ | —CH₃ | H | 4-F-phenyl |
| c2-39 | —CH₃ | —CH₃ | H | —F (position 3) | 4-F-phenyl |
| c2-40 | —CH₃ | —CH₃ | —CH₃ | —F (position 3) | 4-F-phenyl |
| c2-41 | —CH₃ | —CH₃ | H | H | thien-2-yl |
| c2-42 | —CH₃ | —CH₃ | —CH₃ | H | thien-2-yl |
| c2-43 | —CH₃ | —CH₃ | H | —F (position 3) | thien-2-yl |
| c2-44 | —CH₃ | —CH₃ | —CH₃ | —F (position 3) | thien-2-yl |
| c2-45 | —CH₃ | —CH₃ | H | H | 5-chlorothien-2-yl |

Formula (II-c2)

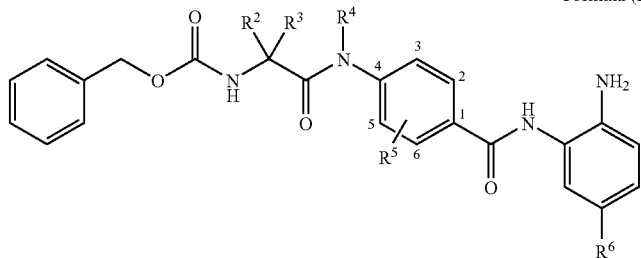

| Comp. No. | R² | R³ | R⁴ | R⁵ | R⁶ |
|---|---|---|---|---|---|
| c2-46 | —CH₃ | —CH₃ | —CH₃ | H | 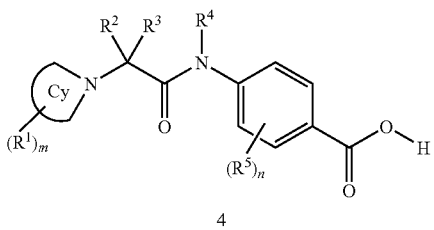 |
| c2-47 | —CH₃ | —CH₃ | H | —F (position 3) | |
| c2-48 | —CH₃ | —CH₃ | —CH₃ | —F (position 3) | |

Compound Preparation

A compound of the present invention such as those of Formulae (I), (I-a), and (I-b) can be prepared according to the schemes described below, but it shall be appreciated that modifications of the illustrated process or other processes can also be used.

Unless otherwise specified, the starting materials and intermediates of the invention such as compounds 1, 2 and 5 are either commercially available or readily prepared by synthetic modifications of the commercially available compounds, using methods known in the literature to those skilled in the art.

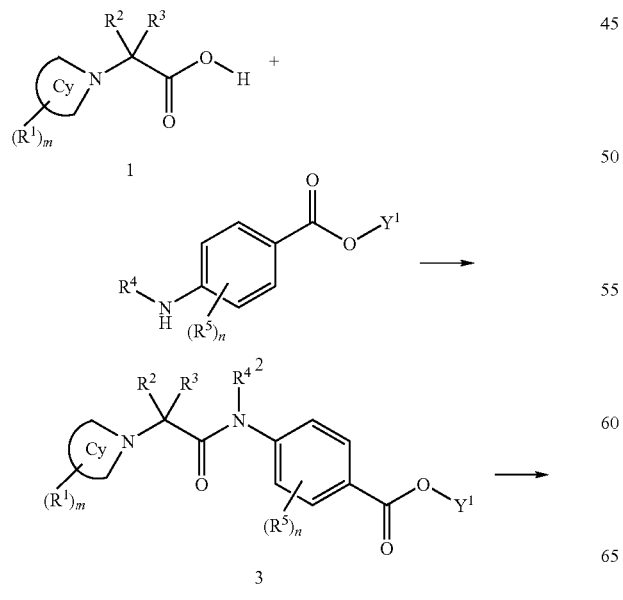

wherein Cy, $R^1$, $R^2$, $R^3$, $R^4$, $R^5$, m, and n are as defined above, and $Y^1$ is alkyl or H.

To Compound 1 in dimethylformamide (DMF) is added 2-(1H-7-azabenzotriazol-1-yl)-1,1,3,3-tetramethyl uronium hexafluorophosphate (HATU), Compound 2, and diisopropylethylamine (DIPEA). The reaction mixture is stirred, diluted with water and acetonitrile, purified by preparative high pressure liquid chromatography (HPLC), and lyophilized, yielding Compound 3.

To Compound 3 in ethanol (EtOH) is added sodium hydroxide (NaOH). The reaction mixture is stirred, concentrated, neutralized with hydrochloric acid (HCl), and extracted with ethyl acetate (EtOAc). The combined organic fractions are then washed with brine and dried over magnesium sulfate (MgSO₄). Filtration and concentration yields Compound 4, which can be used for the next step without purification.

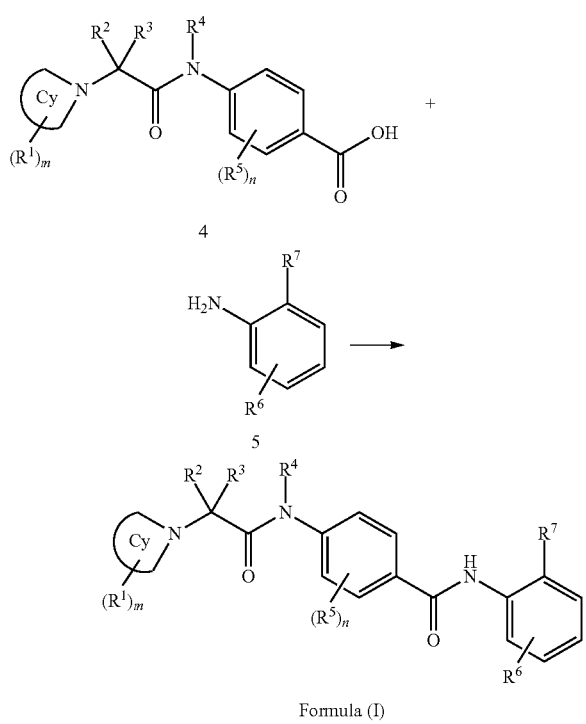

Formula (I)

wherein R⁶ and R⁷ are as defined above.

To Compound 4 in DMF is added HATU, Compound 5, and DIPEA. The reaction mixture is stirred, diluted with water and acetonitrile, directly purified by preparative HPLC, and lyophilized to yield a compound of Formula (I). Determining the suitability of the method (and any necessary routine adaptations) or making a particular intermediate is generally within the skill of those in the art after reading this patent.

The compounds of the present invention inhibit HDAC and are useful to treat or ameliorate diseases mediated directly or indirectly by HDAC. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, at least one pharmaceutically-acceptable diluent, adjuvant, excipient, or carrier. The composition can take any suitable form for the desired route of administration. Where the composition is to be administered orally, any suitable orally deliverable dosage form can be used, including without limitation tablets, capsules (solid- or liquid-filled), powders, granules, syrups and other liquids, elixirs, inhalants, troches, lozenges, and solutions. Injectable compositions or i.v. infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC. Examples of such active ingredients are, without limitation, agents to treat or inhibit cancer, Huntington's disease, cystic fibrosis, liver fibrosis, renal fibrosis, pulmonary fibrosis, skin fibrosis, rheumatoid arthritis, diabetes, stroke, amyotrophic lateral sclerosis, cardiac hypertrophy, heart failure or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hoiniones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitors such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase inhibitors, histone deacetylase 10 inhibitors, and histone deacetylase 11 inhibitors.

Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC since the compounds of the present invention have inhibitory activity against those molecules. In some embodiments, therefore, a method of the present invention is used in inhibiting or treating HDAC-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as Rheumatoid arthritis, diabetes, acute and chronic neurological diseases such as stroke, hypertrophy such as cardiac hypertrophy, heart failure including congestive heart failure, amyotrophic lateral sclerosis, and Alzheimer's disease.

In an embodiment, a method according to the present invention is applied to a patient with cancer, cystic fibrosis, renal fibrosis or pulmonary fibrosis. In some embodiments, a method using a compound according to the present invention is used to treat or inhibit a cancer selected from bladder

Example 1

N-(2-Amino-phenyl)-4-(2-pyrrolidin-1-yl-propionylamino)-benzamide

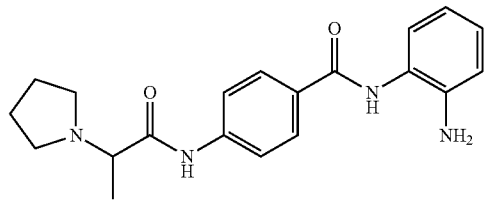

To the 2-pyrrolidin-1-yl-propanoic acid (200 mg, 1.4 mmol) in DMF (10 mL), was added HATU (586 mg, 1.5 mmol), 4-amino-benzoic acid ethyl ester (231 mg, 1.4 mmol) and DIPEA (0.5 mL, 2.8 mmol). The reaction mixture was stirred at room temperature for 16 hours, diluted with water and acetonitrile, purified by preparative HPLC, and lyophilized to give ethyl 4-(2-(pyrrolidin-1-yl)propanamido) benzoate.

To the above ester (207 mg, 0.713 mmol) in ethanol (7 mL) was added 1 N NaOH (7 mL) and stirred at room temperature for 4 hours. The reaction mixture was concentrated, neutralized with 1N HCl and extracted thrice with ethyl acetate. The combined organic layers were then washed with brine, dried over magnesium sulfate, filtered and concentrated to give the acid which was used for the next step without purification.

To the above acid (71 mg, 0.27 mmol) in DMF (3 mL), was added HATU (154 mg, 0.41 mmol), 1,2-phenylenediamine (59 mg, 0.54 mmol) and DIPEA (0.15 mL, 2.8 mmol) and stirred at room temperature for 2 hours. The reaction mixture was diluted with ethylacetate, washed with 1N HCl and water. The organic layer was then concentrated and diluted with water and acetonitrile and directly purified by preparative HPLC, and lyophilized to give the title compound. $C_{20}H_{24}N_4O_2$ 352.9 (M+1). $^1$H-NMR (400 MHz, DMSO-d$_6$): δ 10.12 (s, 1H); 9.68 (s, 1H); 8.08 (d, J=8.4 Hz, 2H); 7.91 (d, J=8.4 Hz, 2H); 7.29 (d, J=7.6 Hz, 1H); 7.09 (t, J=7.2 Hz, 1H); 6.91 (d, J=7.2 Hz, 1H); 6.74 (t, J=8 Hz, 1H); 5.00 (brs, 1H); 3.45 (m, 1H); 2.82 (m, 4H); 1.87 (m, 4H); 1.44 (d, J=6.4 Hz, 3H).

Example 2

N-(2-Amino-5-(4-fluorophenyl)phenyl)-4-(2-(pyrrolidin-1-yl)propanamido)benzamide

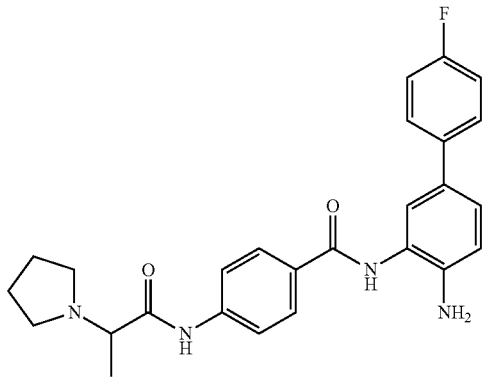

To the 2-pyrrolidin-1-yl-propanoic acid (508 mg, 3.55 mmol) in DMF (10 mL), was added HATU (1.62 g, 4.26 mmol), 4-Amino-benzoic acid ethyl ester (645 mg, 3.90 mmol) and NMM (1.2 mL, 10.65 mmol) and stirred at 50° C. for 16 hours. The reaction mixture was diluted with ethyl acetate (50 mL) and washed with 1 N HCl, saturated NaHCO$_3$, water, brine and dried over MgSO$_4$. Filtration and concentration gave ethyl 4-(2-(pyrrolidin-1-yl)propanamido) benzoate.

To the crude ester in ethanol (7 mL) was added 1 N NaOH (7 mL) and stirred at room temperature for 14 hours. The reaction mixture was concentrated, neutralized with 1N HCl and extracted thrice with ethyl acetate. The combined organic layers were then washed with brine and dried over MgSO$_4$. Filtration and concentration gave the acid which was used for the next step without purification.

To the acid (200 mg, 0.76 mmol) in DMF (5 mL), was added HATU (433 mg, 1.52 mmol), (3-amino-4'-fluoro-biphenyl-4-yl)carbamic acid tert-butyl ester (459 mg, 1.52 mmol) and NMM (0.25 mL, 2.28 mmol) and stirred at room temperature for 48 hours. The reaction mixture was diluted with water and acetonitrile, directly purified by preparative HPLC, and lyophilized to give {4'-fluoro-3-[4-(2-pyrrolidin-1-ylpropionylamino)benzoylamino]-biphenyl-4-yl}carbamic acid tert-butyl ester.

To the BOC-protected compound was added 4.0 M HCl dioxane and stirred at room temperature for 1 hour. The reaction mixture was then concentrated and diluted with water and acetonitrile, directly purified by preparative HPLC, and lyophilized to give the title compound. $C_{26}H_{27}N_4O_2F$ 447.1 (M+1). $^1$H-NMR (400 MHz, DMSO-d$_6$): δ 10.27 (s, 1H); 9.62 (s, 1H); 7.97 (d, J=8.8 Hz, 2H); 7.75 (d, J=8.8 Hz, 2H); 7.56-7.45 (m, 3H); 7.28-7.18 (m, 3H); 6.84 (d, J=8.4 Hz, 1H); 5.05 (brs, 2H); 3.30 (m, 1H); 2.91-2.86 (m, 4H); 1.79 (m, 4H); 1.38 (d, J=6.4 Hz, 3H).

cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES

The following examples are merely illustrative, and do not limit this disclosure in any way.

Example 3

N-(2-Amino-5-(thiophen-2-yl)phenyl)-4-(2-(pyrrolidin-1-yl)propanamido)benzamide

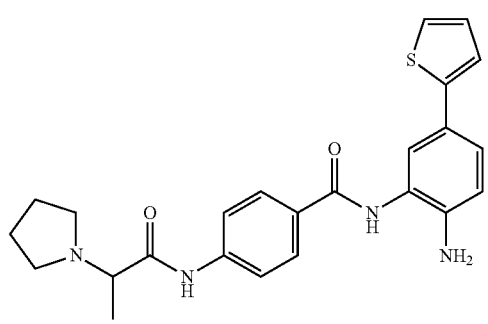

Similar procedure from Example 2 was followed to obtain the title compound using (2-amino-4-thiophen-2-yl-phenyl) carbamic acid tert-butyl ester. $C_{24}H_{26}N_4O_2S$ 435.1 (M+1). $^1$H-NMR (400 MHz, DMSO-d$_6$): δ 9.93 (s, 1H); 9.58 (s, 1H); 7.91 (d, J=8.8 Hz, 2H); 7.73 (d, J=8.8 Hz, 2H); 7.40-7.17 (m, 4H); 6.99-6.97 (m, 1H); 6.75 (d, J=8.4 Hz, 1H); 5.05 (brs, 2H); 3.09 (q, J=6.4 Hz, 1H); 2.57-2.43 (m, 4H); 1.67 (m, 4H); 1.24 (d, J=6.4 Hz, 3H).

Example 4

N-(2-Aminophenyl)-4-(2-(2-oxopyrrolidin-1-yl)propanamido)benzamide

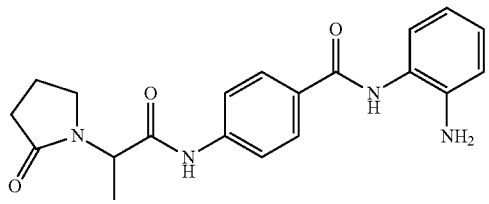

Similar procedure from Example 1 was followed to obtain the title compound using 2-(2)-oxopyrrolidin-1-ylpropanoic acid and 1,2-phenylenediamine. $C_{20}H_{22}N_4O_3$ 367.1 (M+1). $^1$H-NMR (400 MHz, DMSO-d$_6$): δ 10.25 (s, 1H); 9.54 (s, 1H); 7.94 (d, J=8.8 Hz, 2H); 7.72 (d, J=8.8 Hz, 2H); 7.13 (d, J=7.6 Hz, 1H); 6.94 (t, J=7.2 Hz, 1H); 6.75 (d, J=6.8 Hz, 1H); 6.57 (t, J=8 Hz, 1H); 4.71 (q, J=7.2 Hz, 1H); 3.57-3.41 (m, 2H); 2.26 (m, 2H); 1.98-1.91 (m, 2H); 1.36 (d, J=7.2 Hz, 3H).

Example 5

N-(2-Amino-5-(thiophen-2-yl)phenyl)-4-(2-(2-oxopyrrolidin-1-yl)propanamido)benzamide

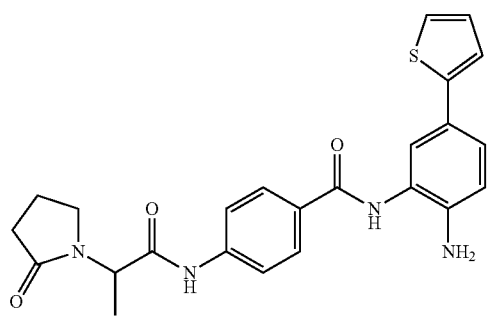

Similar procedure from Example 2 was followed to obtain the title compound using 2-(2)-oxopyrrolidin-1-ylpropanoic acid and (2-amino-4-thiophen-2-yl-phenyl)carbamic acid tert-butyl ester. $C_{24}H_{24}N_4O_3S$ 448.8 (M+1). $^1$H-NMR (400 MHz, DMSO-d$_6$): δ 10.21 (s, 1H); 9.59 (s, 1H); 7.92 (d, J=8.8 Hz, 2H); 7.67 (d, J=8.8 Hz, 2H); 7.40-7.17 (m, 4H); 6.99 (m, 1H); 6.75 (d, J=8.4 Hz, 1H); 5.07 (brs, 2H); 4.68 (q, J=7.2 Hz, 1H); 3.54 (m, 1H); 3.36 (m, 1H); 2.23 (m, 2H); 1.86 (m, 2H); 1.33 (d, J=7.2 Hz, 3H).

Example 6

N-(2-aminophenyl)-4-(2-morpholino-2-phenylacetamido)benzamide

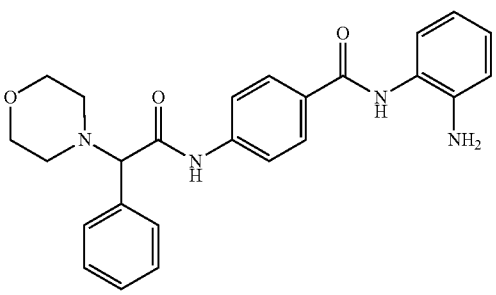

Similar procedure from Example 1 was followed to obtain the title compound using 2-morpholino-2-phenylacetic acid and 1,2-phenylenediamine. $C_{25}H_{26}N_4O_3$ 431.2 (M+1). $^1$H NMR (400 MHz, DMSO-d$_6$): δ 10.33 (s, 1H); 9.53 (s, 1H); 7.89 (d, J=8.8 Hz, 2H); 7.71 (d, J=8.8 Hz, 2H); 7.51 (d, J=7.6 Hz, 1H); 7.36-7.10 (m, 3H); 7.12 (d, J=7.2 Hz, 1H); 6.94 (t, J=7.2 Hz, 1H); 6.75 (d, J=6.8 Hz, 1H); 6.55 (t, J=8 Hz, 1H); 4.02 (s, 1H); 3.60 (m, 4H); 2.37 (m, 4H).

Example 7

N-(2-Amino-5-(4-fluorophenyl)phenyl)-4-(2-(2-oxopyrrolidin-1-yl)propanamido)benzamide

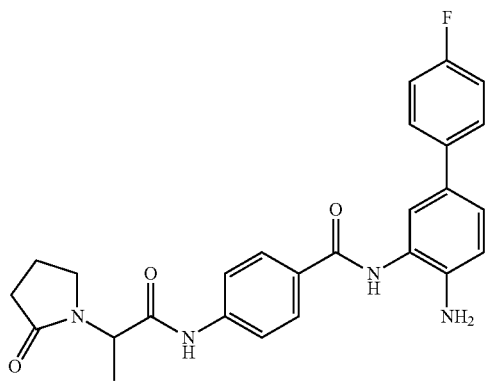

Similar procedure from Example 2 was followed to obtain the title compound using 2-(2)-oxopyrrolidin-1-ylpropanoic acid and 3-amino-4'-fluoro-biphenyl-4-ylcarbamic acid tert-butyl ester. $C_{26}H_{25}N_4O_3F$ 460.9 (M+1). $^1$H-NMR (400 MHz, DMSO-$d_6$): δ 10.24 (s, 1H); 9.60 (s, 1H); 7.95 (d, J=8.8 Hz, 2H); 7.70 (d, J=8.8 Hz, 2H); 7.56-7.45 (m, 2H); 7.27-7.15 (m, 3H); 6.83 (d, J=8.4 Hz, 1H); 5.04 (brs, 2H); 4.72 (q, J=7.2 Hz, 1H); 3.57 (m, 1H); 3.42 (m, 1H); 2.26 (m, 2H); 1.96 (m, 2H); 1.36 (d, J=7.2 Hz, 3H).

Example 8

N-(2-Amino-5-(thiophen-2-yl)phenyl)-4-(2-morpholinopropanamido)benzamide

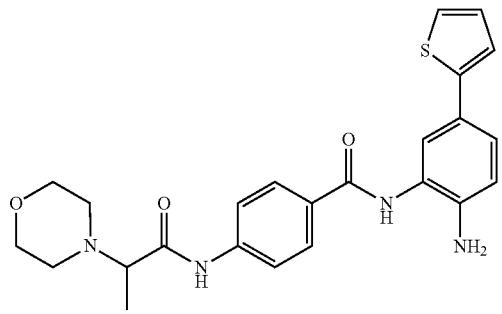

Similar procedure from Example 2 was followed to obtain the title compound using 2-morpholinopropanoic acid and 2-amino-4-thiophen-2-yl-phenylcarbamic acid tert-butyl ester. $C_{24}H_{26}N_4O_3S$ 450.8 (M+1). $^1$H-NMR (400 MHz, DMSO-$d_6$): δ 9.63 (s, 1H); 7.97 (d, J=8.8 Hz, 2H); 7.75 (d, J=8.8 Hz, 2H); 7.44-7.20 (m, 4H); 7.02 (m, 1H); 6.79 (d, J=8.4 Hz, 1H); 3.65 (m, 5H); 2.75 (m, 4H); 126 (m, 3H).

Example 9

N-(2-Amino-5-(4-fluorophenyl)phenyl)-4-(2-morpholinopropanamido)benzamide

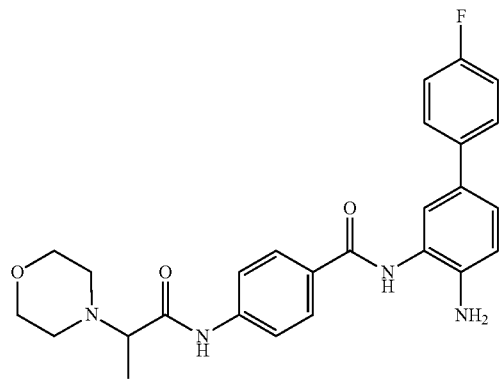

Similar procedure from Example 2 was followed to obtain the title compound using 2-morpholinopropanoic acid and (S)-p-fluorophenyl-1,2-phenylenediamine $C_{26}H_{27}N_4O_3F$ 450.8 (M+1). $^1$H-NMR (400 MHz, DMSO-$d_6$): δ 11.29 (s, 10.19 (s, 1H); 8.09 (d, J=8.4 Hz, 2H); 7.79 (d, J=8.4 Hz, 2H); 7.66-7.61 (m, 3H); 7.44 (m, 1H); 7.26 (m, 3H); 4.24-3.74 (m, 5H); 3.35 (m, 4H); 1.57 (d, J=6.8 Hz, 3H).

Example 10

N-(2-Amino-5-(4-fluorophenyl)phenyl)-4-(2-methyl-2-morpholinopropanamido)benzamide Similar procedure from Example 2 was followed to obtain the title compound using 2-methyl-2-morpholinopropanoic acid and (3-amino-4'-fluoro-biphenyl-4-yl)carbamic acid tert-butyl ester. $C_{27}H_{29}N_4O_3F$ 476.9 (M+1). $^1$H-NMR (400 MHz, DMSO-$d_6$): δ 10.67 (s, 1H); 10.24 (s, 1H); 8.09 (d, J=8.4 Hz, 2H); 7.85 (d, J=8.4 Hz, 2H); 7.68-7.62 (m, 3H); 7.46 (d, J=8.0 Hz, 1H); 7.276 (m, 3H); 3.96-3.42 (m, 8H); 1.71 (s, 6H).

Example 11

N-(2-Amino-5-(thiophen-2-yl)phenyl)-3-fluoro-4-(2-(2-oxopyrrolidin-1-yl)propanamido)benzamide

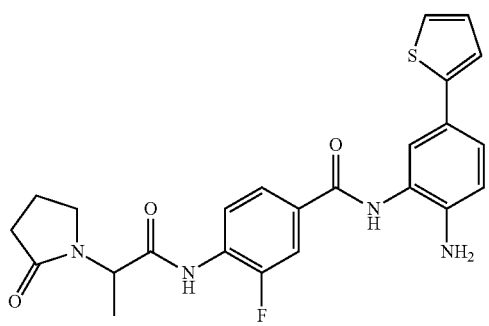

Similar procedure from Example 2 was followed to obtain the title compound using ethyl-4-amino-3-fluorobenzoate, 2-(2)-oxopyrrolidin-1-yl-propanoic acid and 2-amino-4-thiophen-2-yl-phenylcarbamic acid tert-butyl ester. $C_{24}H_{23}FN_4O_3S$ 466.9 (M+1). $^1$H-NMR (400 MHz, DMSO-$d_6$): δ 9.96 (s, 1H); 9.70 (s, 1H); 7.98-7.79 (m, 3H); 7.41 (s, 1H); 7.32-7.20 (m, 3H); 7.01 (m, 1H); 6.78 (d, J=8.8 Hz, 1H); 5.15 (brs, 2H); 4.84 (q, J=7.2 Hz, 1H); 3.53-3.43 (m, 2H); 2.26-2.22 (m, 2H); 1.96-1.91 (m, 2H); 1.36 (d, J=7.2 Hz, 3H).

Example 12

N-(2-Amino-5-(5-chlorothiophen-2-yl)phenyl)-4-(2-(2-oxopyrrolidin-1-yl)propanamido)benzamide

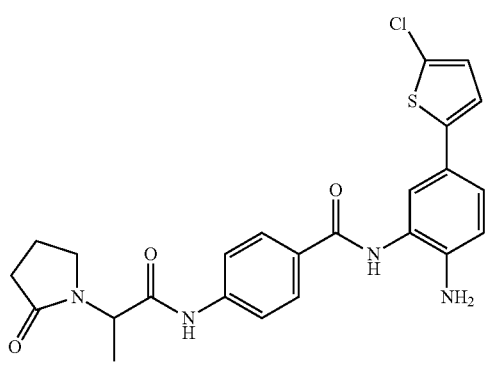

Similar procedure from Example 2 was followed to obtain the title compound using 2-(2)-oxopyrrolidin-1-yl-propanoic acid and 2-amino-4-(5-chloro-thiophen-2-yl)phenyl-carbamic acid tert-butyl ester. $C_{26}H_{23}ClN_4O_3S$ 482.9 (M+1). $^1$H NMR (400 MHz, DMSO-$d_6$): δ 10.24 (s, 1H); 9.61 (s, 1H); 7.94 (d, J=8.4 Hz, 2H); 7.70 (d, J=8.4 Hz, 2H); 7.37 (m, 1H); 7.21 (m, 1H); 7.08 (m, 2H); 6.78 (d, J=8.4 Hz, 1H); 5.18 (brs, 2H); 4.70 (q, J=7.2 Hz, 1H); 3.55 (m, 1H); 3.51 (m, 1H); 2.24 (m, 2H); 1.96 (m, 2H); 1.36 (d, J=7.2 Hz, 3H).

Example 13

N-(2-Aminophenyl)-4-(2-(4-(5-(trifluoromethyl) pyridin-2-yl)piperazin-1yl)propanamido)benzamide

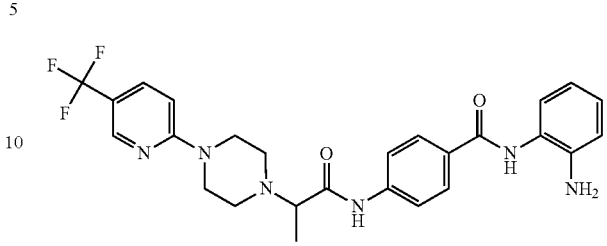

To a solution of 1-[5-(trifluoromethyl)pyrid-2-yl]piperazine (2.00 g, 8.65 mmol) in ethanol (25 mL) and DIPEA (3.3 mL, 19.0 mmol) was added ethyl 2-bromopropionate (1.20 mL, 9.51 mmol). The reaction mixture was heated to 70° C. After 14 hours, the reaction mixture was cooled to room temperature, concentrated and purified by flash chromatography on silica gel with elution using 50% ethyl acetate/hexanes to give 2-[4-(5-trifluoromethyl-pyridin-2-yl)-piperazin-1-yl]propionic acid ethyl ester.

The above ester (416 mgs) was then treated with 1 N HCl and heated in a sealed tube at 100° C. After 48 hours the reaction mixture was cooled to room temperature and concentrated to give an acid which was used for next step without purification.

To the above acid (230 mg, 0.610 mmol) in DMF (2 mL), was added HATU (232 mg, 0.610 mmol), 2-(4-amino-benzoylamino)-phenylcarbamic acid tert-butyl ester (154 mgs, 0.471 mmol) and NMM (0.300 mL, 2.36 mmol). The reaction mixture stirred at 50° C. for 16 hours and diluted with water and acetonitrile. The resulting solid was filtered, washed with water, and dried to give [2-(4-{2-[4-(5-trifluoromethyl-pyridin-2-yl)-piperazin-1-yl]-propionylamino}-benzoylamino)-phenyl]-carbamic acid tert-butyl ester.

To this BOC-protected compound was added 4.0 M HCl dioxane and the resulting reaction mixture was stirred at room temperature for 1 hour. The reaction mixture was then concentrated, diluted with water and acetonitrile, directly purified by preparative HPLC, and lyophilized to give the title compound. $C_{26}H_{27}N_6O_2F_3$ 512.89 (M+1). $^1$H-NMR (400 MHz, DMSO-$d_6$): δ 10.03 (s, 1H); 9.50 (s, 1H); 8.33 (s, 1H); 7.90 (d, J=8.4 Hz, 2H); 7.72 (m, 3H); 7.09 (d, J=7.6 Hz, 1H); 6.91 (m, 2H); 6.72 (d, J=7.2 Hz, 1H); 6.54 (m, 1H); 4.80 (brs, 2H); 3.62 (m, 4H); 3.35 (q, J=6.8 Hz, 3H); 2.62 (m, 4H); 1.17 (d, J=6.8 Hz, 3H).

Example 14

N-(4-Amino-4'-fluorobiphenyl-3-yl)-4-(2-(4-(5-(trifluoromethyl)pyridin-2-yl)piperazin-1-yl)propanamido)benzamide

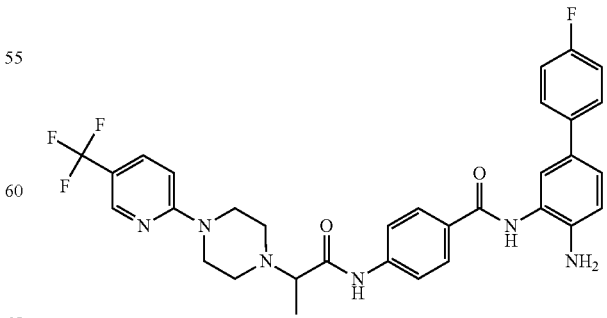

Similar procedure from Example 13 was followed to obtain the title compound using (3-amino-4'-fluoro-biphenyl-4-yl)

carbamic acid tert-butyl ester. $C_{32}H_{30}N_6O_2F_4$ 606.92 (M+1). $^1$H-NMR (400 MHz, DMSO-$d_6$): δ 10.07 (s, 1H); 9.61 (s, 1H); 8.37 (s, 1H); 7.96 (d, J=8.8 Hz, 2H); 7.77 (m, 3H); 7.56 (m, 3H); 7.27-7.15 (m, 3H); 6.93-6.81 (m, 2H); 5.04 (brs, 2H); 3.67 (m, 4H); 3.34 (q, J=6.8 Hz, 3H); 2.66 (m, 4H); 1.21 (d, J=6.8 Hz, 3H).

Example 15

N-(4-Amino-4'-fluorobiphenyl-3-yl)-3-fluoro-4-[2-(2-oxo-pyrrolidin-1-yl)-propionylamino]-benzamide

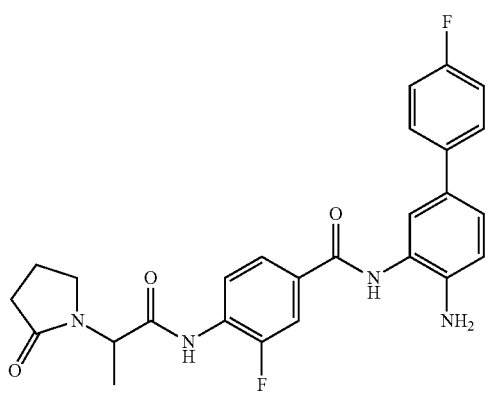

Similar procedure from Example 2 was followed to obtain the title compound using 2-(2-oxopyrrolidin-1-yl)propanoic acid and tert-butyl 3-(4-amino-3-fluorobenzamido)-4'-fluorobiphenyl-4-ylcarbamate. $C_{26}H_{24}F_2N_4O_3$ 478.9 (M+1). $^1$H NMR (400 MHz, DMSO-$d_6$): δ 10.32 (s, 1H); 10.02 (s, 1H); 8.03-7.87 (m, 3H); 7.68-7.63 (m, 3H); 7.51-7.49 (m, 1H); 7.49-7.23 (m, 3H); 4.86 (q, J=7.6 Hz, 1H); 3.54-3.42 (m, 2H); 2.26-2.22 (m, 2H); 1.97-1.92 (m, 2H); 1.37 (d, J=7.6 Hz, 3H).

Example 16

N-(4-Amino-4'-fluorobiphenyl-3-yl)-4-(2-methyl-2-(piperazin-1-yl)-propanamido)benzamide

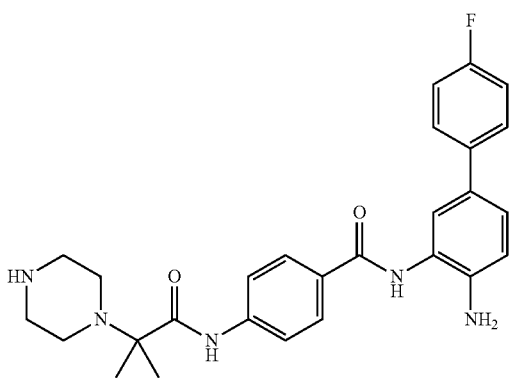

Similar procedure from Example 2 was followed to obtain the title compound using 4-(1-Carboxy-1-methyl-ethyl)-piperazine-1-carboxylic acid tert-butyl ester [3-(4-Amino-benzoylamino)-4'-fluoro-biphenyl-4-yl]-carbamic acid tert-butyl ester. $C_{27}H_{30}FN_5O_2$ 475.9 (M+1). $^1$H NMR (400 MHz, DMSO-$d_6$): δ 10.38 (s, 1H); 9.90 (brs, 1H); 9.09 (brs, 1H); 8.10 (d, J=8.4 Hz, 2H); 7.85 (d, J=8.8 Hz, 2H); 7.76 (s, 1H); 7.68-7.64 (m, 2H); 7.54-7.25 (m, 3H); 3.70 (m, 4H); 3.23 (m, 4H); 1.23 (s, 6H).

Example 17

N-(4-Amino-4',6-difluorobiphenyl-3-yl)-4-(2-(2-oxopyrrolidin-1-yl)propanamido)benzamide

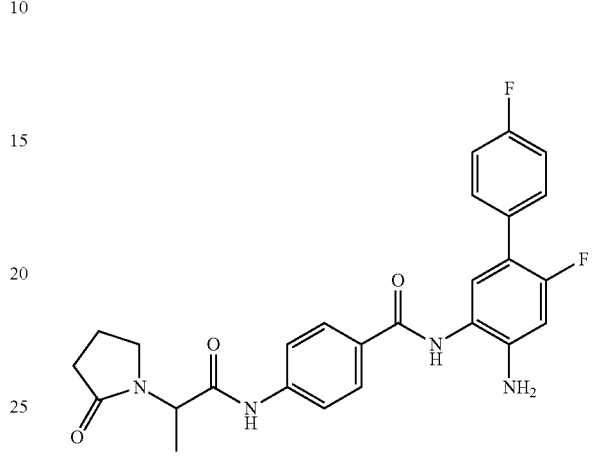

To 2-(2)-oxopyrrolidin-1-ylpropanoic acid (0.95 g, 6.04 mmol) in DMF (5 mL) was added HATU (3.2 g, 8.5 mmol), tert-butyl 4-aminobenzoate (1.2 g, 2.12 mmol) and NMM (1.4 mL, 13.30 mmol). The reaction mixture was stirred at 55° C. for 2 hours and then diluted with Acetonitrile/water (2:1, 30 mL) and the resulting solid was stirred and filtered and washed with water and dried to give tert-butyl 4-(2-(2-oxopyrrolidin-1-yl)propanamido)benzoate which was used for the next step with out purification.

To the above ester in DCM (26 mL) was added TFA (8.7 mL) and stirred at room temperature. After 3 hours, the reaction mixture was concentrated and treated with $Et_2O$. The solid formed was then filtered and washed with ether and dried to give 4-(2-(2-oxopyrrolidin-1-yl)propanamido)benzoic acid.

To the above acid (414 mgs, 1.5 mmol) in DMF (2 mL), was added HATU (495 mg, 1.53 mmol), tert-butyl 5-amino-2,4'-difluorobiphenyl-4-ylcarbamate (320 mg, 1.00 mmol) and NMM (0.2 mL, 2.0 mmol) and stirred at 55° C. for 18 hours. The reaction mixture was then diluted with water and acetonitrile and the precipitate formed was then filtered, washed with water and dried. The solid was then purified by column chromatography on silica gel with elution using 80% ethyl acetate/hexanes to give tert-butyl 2,4'-difluoro-5-(4-(2-(2-oxopyrrolidin-1-yl)propanamido)benzamido)biphenyl-4-ylcarbamate.

To the above bis-BOC protected compound, 4.0 M HCl dioxane (10 mL) was added and stirred at room temperature for 1 hour. The reaction mixture was then diluted with $Et_2O$ and stirred. The resulting solid was filtered, washed with ether, and diluted with water and acetonitrile and purified by preparative HPLC, and lyophilized to give the title compound. $C_{26}H_{24}F_2N_4O_3$ 479.0 (M+1). NMR (400 MHz, DMSO-$d_6$): δ 10.19 (s, 1H); 9.52 (s, 1H); 7.91 (d, J=8.4 Hz, 2H); 7.66 (d, J=8.4 Hz, 2H); 7.43-7.40 (m, 2H); 7.23-7.17 (m, 3H); 6.59 (d, J=13.2 Hz, 1H); 5.30 (s, 2H); 4.68 (q, J=7.2 Hz, 1H); 3.54-3.37 (m, 2H); 2.22-2.18 (m, 2H); 1.94-1.87 (m, 2H); 1.32 (d, J=7.2 Hz, 3H).

Example 18

N-(2-amino-5-fluorophenyl)-4-(2-(2-oxopyrrolidin-1-yl)propanamido)benzamide

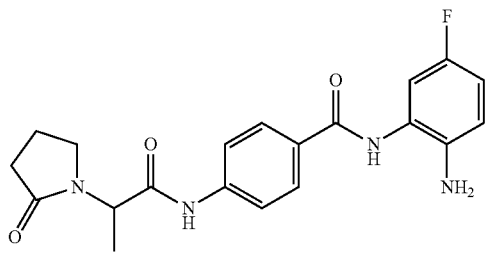

To the 4-(2-(2-oxopyrrolidin-1-yl)propanamido)benzoic acid (210 mgs, 0.76 mmol) in DMF (2 mL), was added HATU (375 mg, 0.99 mmol), tert-butyl 2-amino-4-fluorophenylcarbamate (172 mg, 0.76 mmol) and NMM (0.3 mL, 2.3 mmol) and stirred at 55° C. for 40 hours. The reaction mixture was then diluted with water and acetonitrile and the precipitate formed was then filtered, washed with water and dried. The solid was then purified by column chromatography on silica gel with elution using 80% ethyl acetate/hexanes to give tert-butyl 4-fluoro-2-(4-(2-(2-oxopyrrolidin-1-yl)propanamido)benzamido)phenylcarbamate.

To the above bis-BOC protected compound, 4.0 M HCl dioxane (7 mL) was added and stirred at room temperature for 1 hour. The reaction mixture was then diluted with ether and stirred. The resulting solid was filtered, washed with ether, and diluted with 1N HCl and acetonitrile and lyophilized to give the title compound. $C_{20}H_{21}FN_4O_3$ 384.9 (M+1). $^1$H NMR (400 MHz, DMSO-$d_6$): δ 10.50 (s, 1H); 10.39 (s, 1H); 8.08 (d, J=8.0 Hz, 2H); 7.77-7.73 (m, 2H); 7.50-7.47 (m, 2H); 7.19-7.14 (m, 1H); 4.68 (q, J=7.2 Hz, 1H); 3.57-3.52 (m, 1H); 3.45-3.41 (n, 1H); 2.25-2.21 (m, 2H); 1.97-1.87 (m, 2H); 1.37 (d, J=7.2 Hz, 3H).

Example 19

N-(2-amino-4,6-difluorophenyl)-4-(2-(2-oxopyrrolidin-1-yl)propanamido)benzamide

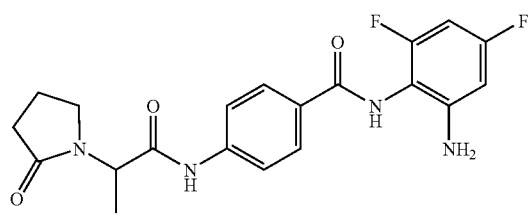

Similar procedure from Example 2 was followed to obtain the title compound using tert-butyl 2-amino-3,5-difluorophenylcarbamate. $C_{20}H_{20}F_2N_4O_3$ 402.9 (M+1). $^1$H NMR (400 MHz, DMSO-$d_6$): δ 10.30 (s, 1H); 9.37 (s, 1H); 7.94 (d, J=8.4 Hz, 2H); 7.70 (d, J=8.4 Hz, 2H); 6.37-6.32 (m, 2H); 4.71 (brs, NH); 4.71 (q, J=7.2 Hz, 1H); 3.57-3.51 (m, 1H); 3.44-3.39 (m, 1H); 2.25-2.21 (m, 2H); 1.97-1.89 (m, 2H); 1.36 (d, J=7.2 Hz, 3H).

Example 20

N-(4-amino-4'-fluorobiphenyl-3-yl)-4-(2-(2-oxopyrrolidin-1-yl)acetamido)benzamide

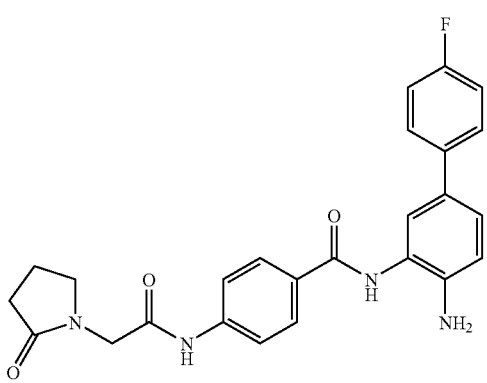

To the 2-(2-oxopyrrolidin-1-yl)acetic acid (186 mgs, 1.3 mmol) in DMF (3 mL), was added HATU (570 mg, 1.5 mmol), tert-butyl 3-(4-aminobenzamido)-4'-fluorobiphenyl-4-ylcarbamate (421 mg, 1.0 mmol) and NMM (0.3 mL, 3.0 mmol) and stirred at 55° C. for 40 hours. The reaction mixture was then diluted with water and acetonitrile and the precipitate was filtered, washed with water and dried and used further without purification. To the above BOC protected compound, 4.0 M HCl dioxane (7 mL) was added and stirred at room temperature for 2 hour. The reaction mixture was then diluted with ether and stirred. The resulting solid was filtered, washed with ether and dried to give the title compound. $C_{25}H_{23}FN_4O_3$ 446.9 (M+1). $^1$H NMR (400 MHz, DMSO-$d_6$): δ 10.60 (s, 2H); 8.12 (d, J=8.4 Hz, 2H); 7.86 (s, 1H); 7.75 (d, J=8.4 Hz, 2H); 7.73-7.68 (m, 2H); 7.61-7.56 (m, 2H); 7.31 (m, 2H); 4.07 (s, 2H); 3.43-3.40 (m, 2H); 3.44-3.39 (m, 1H); 2.24-2.22 (m, 2H); 1.98-1.92 (m, 2H).

Example 21

N-(2-aminophenyl)-4-(2-methyl-2-(4-(5-(trifluoromethyl)pyridin-2-yl)piperazin-1-yl)propanamido)benzamide

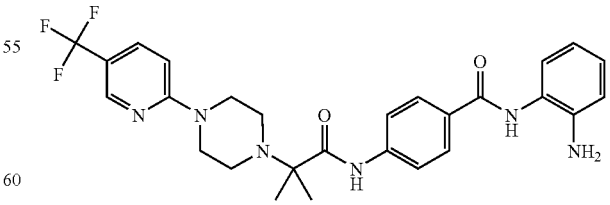

To a solution of 1-[5-(trifluoromethyl)pyrid-2-yl]piperazine (554 mgs, 2.4 mmol) in CH$_3$CN (5 mL) and K$_2$CO$_3$ (1.1 g, 8.0 mmol) was added benzyl 2-bromo-2-methylpropanoate (512 mgs, 2.0 mmol). The reaction mixture was heated to 80° C. After 14 hours, the reaction mixture was cooled to room temperature, diluted with EtOAc, stirred and filtered. The filtrate was then concentrated and purified by flash chromatography on silica gel with elution using 3% MeOH/CH$_2$Cl$_2$ to give Benzyl 2-methyl-2-(4-(5-(trifluoromethyl)pyridin-2-yl)piperazin-1-yl)propanoate.

To the above Benzyl ester (381 mgs) in EtOAc (6 mL) was added 1,4-cyclohexadiene (1.0 mL) and 10% Pd/C (100 mgs) and the reaction mixture was heated in microwave (Biotage) at 100° C. for 30 min. The reaction mixture was then diluted with EtOAc and MeOH, filtered and concentrated to give 2-methyl-2-(4-(5-(trifluoromethyl)pyridin-2-yl)piperazin-1-yl)propanoic acid which was used further without purification.

To the above acid (220 mgs, 0.69 mmol) in DMF (2 mL), was added HATU (396 mg, 1.04 mmol), tert-butyl 2-(4-aminobenzamido)phenylcarbamate (227 mg, 0.69 mmol) and NMM (0.23 mL, 2.08 mmol) and stirred at 55° C. for 40 hours. The reaction mixture was then diluted with water and acetonitrile and the precipitate was filtered, washed with water and dried. The solid was then purified by column chromatography on silica gel with elution using 60% ethyl acetate/hexanes to give tert-butyl 2-(4-(2-methyl-2-(4-(5-(trifluoromethyl)pyridin-2-yl)piperazin-1-yl)propanamido)benzamido)phenylcarbamate.

To the above BOC protected compound, 4.0 M HCl dioxane (5 mL) was added and stirred at room temperature for 1 hour. The reaction mixture was then diluted with ether and stirred. The resulting solid was filtered, washed with ether, and diluted with 1N HCl and acetonitrile and lyophilized to give the title compound. C$_{27}$H$_{29}$F$_3$N$_6$O$_2$ 527.1 (M+1). $^1$H NMR (400 MHz, DMSO-d$_6$): δ 10.85 (brs, 2H); 10.54 (s, 1H); 8.45 (s, 1H); 8.14 (d, J=8.4 Hz, 2H); 7.90-7.86 (m, 3H); 7.60-7.29 (m, 4H); 7.05 (d, J=8.8 Hz, 1H); 4.58-4.55 (m, 4H); 3.63-3.51 (m, 4H); 1.74 (s, 6H).

Example 22

N-(4-amino-4'-fluorobiphenyl-3-yl)-4-(2-(4-cyclopropylpiperazin-1-yl)-2-methylpropanamido)benzamide

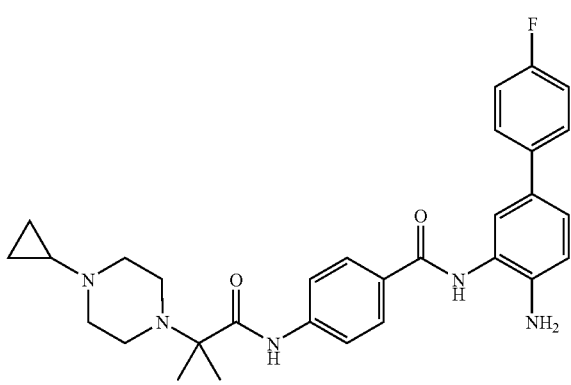

Similar procedure from Example 21 was followed to obtain the title compound using 1-cyclopropylpiperazine and tert-butyl 3-(4-aminobenzamido)-4'-fluorobiphenyl-4-ylcarbamate instead of 1-[5-(trifluoromethyl)pyrid-2-yl]piperazine and tert-butyl 2-(4-aminobenzamido)phenylcarbamate. C$_{30}$H$_{34}$FN$_5$O$_2$ 516.1 (M+1). $^1$H NMR (400 MHz, DMSO-d$_6$): δ 10.70 (brs, 1H); 10.34 (s, 1H); 9.89 (brs, 1H); 8.45 (s, 1H); 8.10 (d, J=8.4 Hz, 2H); 7.86 (d, J=8.4 Hz, 2H); 7.75-7.64 (m, 2H); 7.51-7.26 (m, 5H); 3.61 (m, 4H); 2.77 (m, 4H); 2.63 (m, 1H); 1.23 (s, 6H); 1.09 (m, 2H); 0.76 (m, 2H).

Example 23

N-(4-amino-4'-fluorobiphenyl-3-yl)-4-(2-methyl-2-(2-oxopyrrolidin-1-yl)propanamido)benzamide

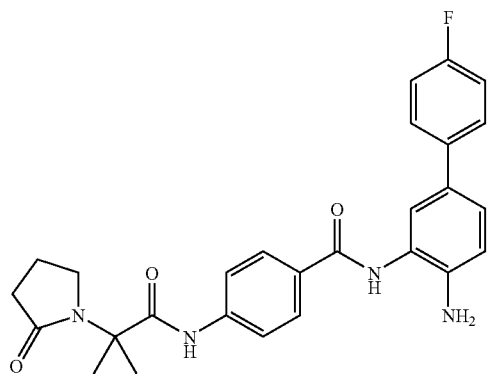

To a solution of methyl α-aminoisobutyrate hydrochloride (1.25 g, 8.1 mmol) in DCM (10 mL) and pyridine (2.6 mL, 32.4 mmol), 4-chlorobutyryl chloride (1.0 mL, 8.9 mmol) in DCM (5 mL) was added slowly at 0° C. The reaction mixture was gradually warmed to room temperature and stirred for 16 hours. The reaction mixture was diluted with DCM (30 mL), and quenched with saturated NaHCO$_3$ (30 mL). The organic layer was separated and the aqueous layer was extracted twice with DCM. The combined organic layers were then washed with saturated aqueous NaHCO$_3$ and brine, dried over MgSO$_4$, filtered and concentrated and was used further without purification.

The intermediate from above in dry THF (15 mL) was added to a suspension of NaH (454 mgs, 11.34 mmol) in dry THF (5 mL) and stirred at room temperature for 16 hours. The reaction mixture was then quenched with 3N NaOH (13.5 mL) and stirred at rt. After 12 hours, the reaction mixture was concentrated, diluted with water and neutralized with 6 N HCl. The aqueous layer was extracted twice with EtOAc and the combined organic layers were then washed with and brine, dried over MgSO$_4$, filtered and concentrated to give the acid which required no further purification.

To the above acid (171 mgs, 0.69 mmol) in DMF (2 mL), was added HATU (468 mg, 1.23 mmol), tert-butyl 3-(4-aminobenzamido)-4'-fluorobiphenyl-4-ylcarbamate (324 mg, 0.77 mmol) and NMM (0.4 mL, 3.85 mmol) and stirred at 55° C. for 40 hours. The reaction mixture was then diluted with water and acetonitrile and the precipitate was filtered, washed with water and dried. The solid was then purified by column chromatography on silica gel with elution using 80% ethyl acetate/hexanes to give tert-butyl-4'-fluoro-3-(4-(2-methyl-2-(2-oxopyrrolidin-1 yl)propanamido)benzamido)biphenyl-4-ylcarbamate.

To the above BOC protected compound, 4.0 M HCl dioxane (12 mL) was added and stirred at room temperature for 2 hour. The reaction mixture was then diluted with ether and stirred. The resulting solid was filtered, washed with ether, and diluted with water and acetonitrile purified by preparative HPLC, and lyophilized to give the title compound. C$_{27}$H$_{27}$FN$_4$O$_3$ 474.9 (M+1). $^1$H NMR (400 MHz, DMSO-d$_6$): δ 9.61 (s, 1H); 9.43 (s, 1H); 7.94 (d, J=8.8 Hz, 2H); 7.70

(d, J=8.8 Hz, 2H); 7.56-7.53 (m, 2H); 7.46 (s, 1H); 7.27-7.17 (m, 3H); 6.84 (d, J=8.0 Hz, 1H); 5.04 (brs, 2H); 3.49-3.44 (m, 2H); 2.21-2.17 (m, 2H); 1.99-1.97 (m, 2H); 1.36 (s, 6H).

Example 24

N-(2-amino-5-(cyclopropylethynyl)phenyl)-4-(2-(2-oxopyrrolidin-1-yl)propanamido)benzamide

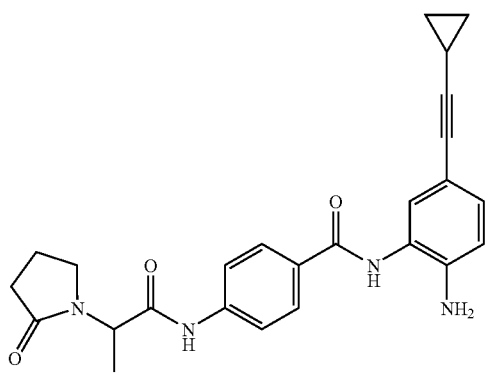

Similar procedure from Example 2 was followed to obtain the title compound using tert-butyl 2-amino-4-(cyclopropylethynyl)phenylcarbamate. $C_{25}H_{26}N_4O_3$ 430.9 (M+1). $^1$H NMR (400 MHz, DMSO-$d_6$): δ 10.23 (s, 1H); 9.46 (s, 1H); 7.91 (d, J=8.4 Hz, 2H); 7.68 (d, J=8.4 Hz, 2H); 7.14 (s, 1H); 6.93 (d, J=8.0 Hz, 2H); 6.65 (d, J=8.0 Hz, 2H); 5.18 (s, 2H); 4.68 (q, J=7.2 Hz, 1H); 3.55-3.53 (m, 1H); 3.43-3.41 (m, 1H); 2.24-2.22 (m, 2H); 1.92-1.90 (m, 2H); 1.35 (m, 1H); 1.33 (d, J=7.2 Hz, 3H); 0.79-0.76 (m, 2H); 0.63-0.60 (m, 2H).

Example 25

N-(2-amino-5-(phenylethynyl)phenyl)-4-(2-(2-oxopyrrolidin-1-yl)propanamido)benzamide

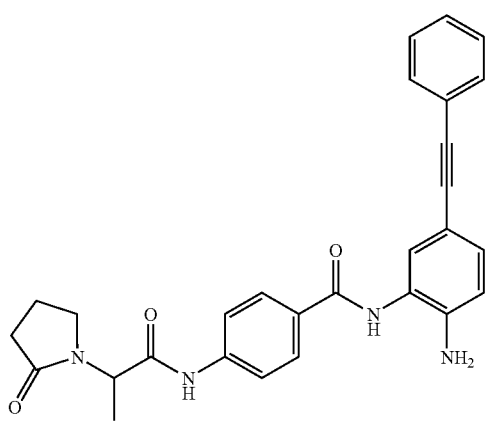

Similar procedure from Example 2 was followed to obtain the title compound using tert-butyl 2-amino-4-(phenylethynyl)phenylcarbamate. $C_{28}H_{26}N_4O_3$ 466.9 (M+1). $^1$H NMR (400 MHz, DMSO-$d_6$): δ 10.23 (s, 1H); 9.50 (s, 1H); 7.91 (d, J=8.4 Hz, 2H); 7.67 (d, J=8.4 Hz, 2H); 7.42-7.28 (m, 6H); 7.10-7.08 (m, 1H); 6.72 (d, J=8.0 Hz, 2H); 5.40 (brs, 2H); 4.66 (q, J=7.2 Hz, 1H); 3.54-3.50 (m, 1H); 3.42-3.37 (m, 1H); 2.23-2.19 (m, 2H); 1.95-1.87 (m, 2H); 1.32 (d, J=7.2 Hz, 3H).

Example 26

(S)—N-(2-aminophenyl)-4-(3,3-dimethyl-2-(2-oxopyrrolidin-1-yl)butanamido)benzamide

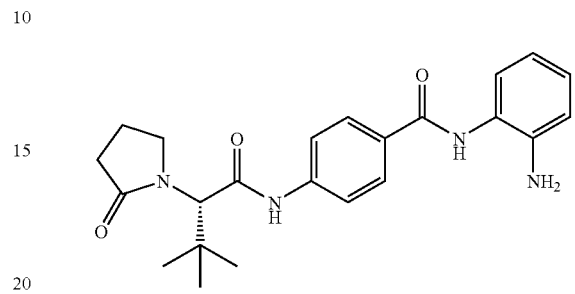

Similar procedure from Example 23 was followed to obtain the title compound using (S)-methyl 2-amino-3,3-dimethylbutanoate hydrochloride and tert-butyl 2-(4-aminobenzamido)phenylcarbamate instead of methyl α-aminoisobutyrate hydrochloride and tert-butyl 3-(4-aminobenzamido)-4'-fluorobiphenyl-4-ylcarbamate. $C_{23}H_{28}N_4O_3$ 408.9 (M+1). $^1$H NMR (400 MHz, DMSO-$d_6$): δ 10.46 (s, 1H); 9.54 (s, 1H); 7.92 (d, J=8.4 Hz, 2H); 7.71 (d, J=8.4 Hz, 2H); 7.12 (d, J=7.2 Hz, 1H); 6.95-6.91 (m, 1H); 6.75-6.73 (m, 1H); 6.58-6.53 (m, 1H); 4.84 (brs, 2H); 4.64 (s, 1H); 3.75-3.65 (m, 2H); 2.27-2.22 (m, 2H); 1.90-1.88 (m, 2H); 1.00 (s, 9H).

Example 27

(S)—N-(4-amino-4'-fluorobiphenyl-3-yl)-4-(3,3-dimethyl-2-(2-oxopyrrolidin-1-yl)butanamido)benzamide

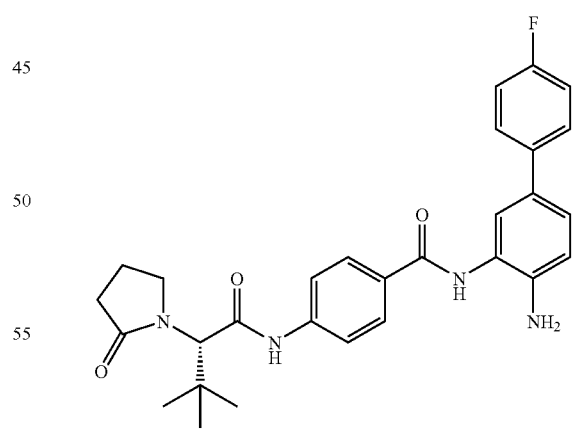

Similar procedure from Example 23 was followed to obtain the title compound using (S)-methyl 2-amino-3,3-dimethylbutanoate hydrochloride and tert-butyl 3-(4-aminobenzamido)-4'-fluorobiphenyl-4-ylcarbamate. $C_{29}H_{31}N_4O_3F$ 503.0 (M+1). $^1$H NMR (400 MHz, DMSO-$d_6$): δ 10.47 (s, 1H); 9.62 (s, 1H); 7.94 (d, J=8.4 Hz, 2H); 7.73 (d, J=8.4 Hz, 2H); 7.56-7.52 (m, 2H); 7.45 (s, 1H); 7.27-7.17 (m, 3H); 6.83

(d, J=8.0 Hz, 1H); 5.05 (brs, 2H); 4.65 (s, 1H); 3.77-3.63 (m, 2H); 2.27-2.22 (m, 2H); 1.92-1.88 (m, 2H); 1.00 (s, 9H).

Example 28

N-(4-amino-4'-fluorobiphenyl-3-yl)-4-(2-morpholinoacetamido)benzamide

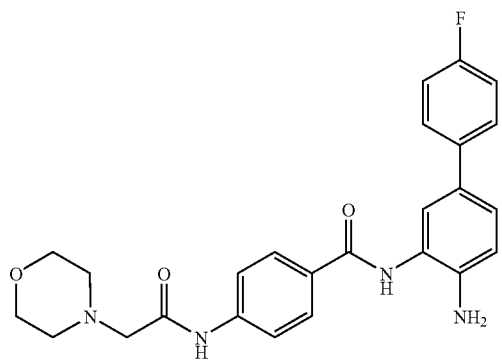

Similar procedure from Example 20 was followed to obtain the title compound using 2-morpholinoacetic acid instead of 2-(2-oxopyrrolidin-1-yl)acetic acid. $C_{25}H_{25}FN_4O_3$ 449.1 (M+1), $^1$H NMR (400 MHz, DMSO-$d_6$): δ 9.97 (s, 1H); 9.62 (s, 1H); 7.93 (d, J=8.4 Hz, 2H); 7.75 (d, J=8.4 Hz, 2H); 7.56-7.52 (m, 2H); 7.44 (s, 1H); 7.27-7.17 (m, 3H); 6.83 (d, J=8.4 Hz, 1H); 5.05 (s, 2H); 3.62-3.60 (m, 4H); 3.29 (m, 4H); 3.14 (s, 2H).

Example 29

N-(4-amino-4'-fluorobiphenyl-3-yl)-4-(2-(4-ethylpiperazin-1-yl)acetamido)benzamide

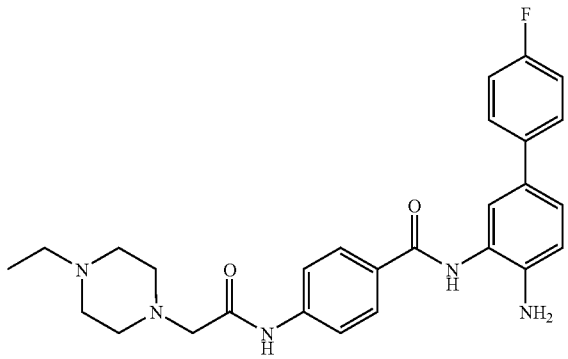

Similar procedure from Example 20 was followed to obtain the title compound using 2-(4-ethylpiperazin-1-yl)acetic acid instead of 2-(2-oxopyrrolidin-1-yl)acetic acid. $C_{27}H_{30}FN_5O_2$ 476.2 (M+1). $^1$H NMR (400 MHz, DMSO-$d_6$): δ 9.93 (s, 1H); 9.62 (s, 1H); 7.95 (d, J=8.4 Hz, 2H); 7.74 (d, J=8.4 Hz, 2H); 7.56-7.52 (m, 2H); 7.45 (s, 1H); 7.27-7.17 (m, 3H); 6.83 (d, J=8.4 Hz, 1H); 5.05 (s, 2H); 3.13 (s, 2H); 2.52-2.36 (m, 10H); 1.00 (d, J=7.2 Hz, 3H).

Example 30

N-(4-amino-4'-fluorobiphenyl-3-yl)-4-(2-(2-oxopiperidin-1-yl)acetamido)benzamide

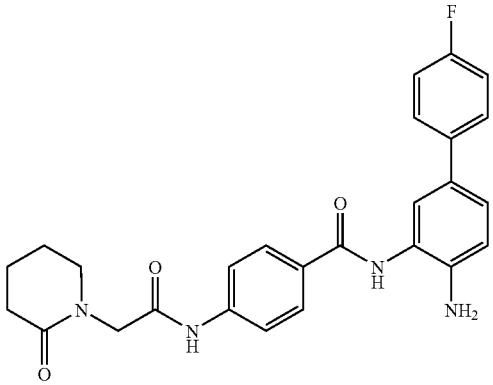

Similar procedure from Example 20 was followed to obtain the title compound using 2-(2-oxopiperidin-1-yl)acetic acid instead of 2-(2-oxopyrrolidin-1-yl)acetic acid. $C_{26}H_{25}FN_4O_3$ 461.0 (M+1). $^1$H NMR (400 MHz, DMSO-$d_6$): δ 10.27 (s, 1H); 9.62 (s, 1H); 7.95 (d, J=8.4 Hz, 2H); 7.68 (d, J=8.4 Hz, 2H); 7.56-7.52 (m, 2H); 7.44 (s, 1H); 7.27-7.17 (m, 3H); 6.83 (d, J=8.4 Hz, 1H); 5.05 (s, 2H); 4.09 (s, 2H); 3.34 (m, 2H); 2.29 (m, 2H); 1.73 (m, 4H).

Example 31

N-(4'-fluoro-4-(prop-2-ynylamino)biphenyl-3-yl)-4-(2-(2-oxopyrrolidin-1-yl)propanamido)benzamide

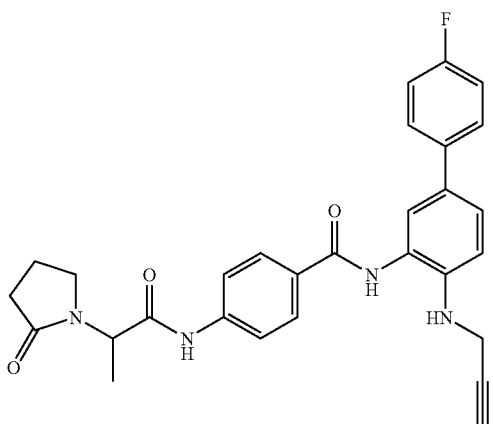

Similar procedure from Example 2 was followed to obtain the title compound using 2-(2-oxopyrrolidin-1-yl)propanoic acid and tert-butyl 3-(4-aminobenzamido)-4'-fluorobiphenyl-4-yl(prop-2-ynyl)carbamate. $C_{29}H_{27}N_4O_2F$ 499.1 (M+1). $^1$H NMR (400 MHz, DMSO-$d_6$): δ 10.20 (s, 1H); 9.57 (s, 1H); 7.94 (d, J=8.8 Hz, 2H); 7.67 (d, J=8.8 Hz, 2H); 7.56-7.54 (m, 2H); 7.42 (s, 1H); 7.39-7.37 (m, 1H); 7.17 (m, 2H); 6.82 (d, J=8.4 Hz, 1H); 5.62 (d, J=5.6 Hz, 1H); 4.68 (q, J=7.2 Hz, 1H); 3.91(dd, J=5.6 Hz, 2.0 Hz, 2H); 3.54-3.52 (m, 1H); 3.42-3.36 (m, 1H); 3.04 (t, J=2.0 Hz, 1H); 2.23-2.19 (m, 2H); 1.95-1.87 (m, 2H); 1.33 (d, J=7.2 Hz, 3H).

Example 32

N-(4'-fluoro-4-(2-methoxyethylamino)biphenyl-3-yl)-4-(2-(2-oxopyrrolidin-1-yl)propanamido)benzamide

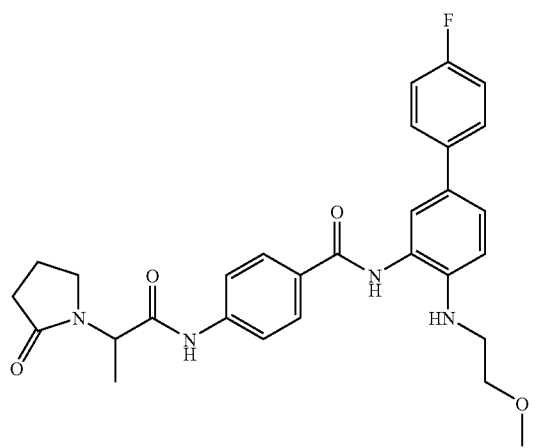

Similar procedure from Example 2 was followed to obtain the title compound using 2-(2-oxopyrrolidin-1-yl)propanoic acid and tert-butyl 3-(4-aminobenzamido)-4'-fluorobiphenyl-4-yl(2-methoxyethyl)carbamate. $C_{29}H_{31}N_4O_4F$ 519.0 (M+1). $^1H$ NMR (400 MHz, DMSO-$d_6$): δ 10.32 (s, 1H); 9.91 (s, 1H); 7.99 (d, J=8.8 Hz, 2H); 7.73 (d, J=8.8 Hz, 2H); 7.62-7.58 (m, 2H); 7.54 (s, 1H); 7.47-7.44 (m, 1H); 7.23 (m, 2H); 7.01 (d, J=8.4 Hz, 1H); 5.01 (brs, NH); 4.72 (q, J=7.2 Hz, 1H); 3.55-3.28 (m, 6H); 3.21 (s, 3H); 2.26-2.22 (m, 2H); 1.96-1.91 (m, 2H); 1.36 (d, J=7.2 Hz, 3H).

Example 33

N-(4-amino-4'-fluorobiphenyl-3-yl)-3-(2-(2-oxopyrrolidin-1-yl)propanamido)benzamide

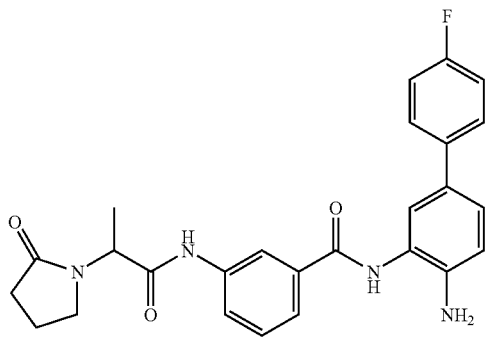

Similar procedure from Example 2 was followed to obtain the title compound using 2-(2-oxopyrrolidin-1-yl)propanoic acid and ten-butyl 3-(3-aminobenzamido)-4'-fluorobiphenyl-4-ylcarbamate. $C_{26}H_{25}N_4O_3F$ 460.9 (M+1). $^1H$ NMR (400 MHz, DMSO-$d_6$): δ 10.33 (s, 1H); 10.22 (s, 1H); 8.24 (s, 1H); 7.80-7.77 (m, 2H); 7.69-7.64 (m, 3H); 7.53-7.43 (m, 2H); 7.32-7.24 (m, 3H); 4.69 (q, J=7.2 Hz, 1H); 3.55 (m, 1H); 3.43 (m, 1H); 2.25-2.23 (m, 2H); 1.96-1.91 (m, 2H); 1.36 (d, J=7.2 Hz, 3H).

Example 34

(R)—N-(4-amino-4'-fluorobiphenyl-3-yl)-4-(2-(2-oxopyrrolidin-1-yl)propanamido)benzamide and (S)—N-(4-amino-4'-fluorobiphenyl-3-yl)-4-(2-(2-oxopyrrolidin-1-yl)propanamido)benzamide

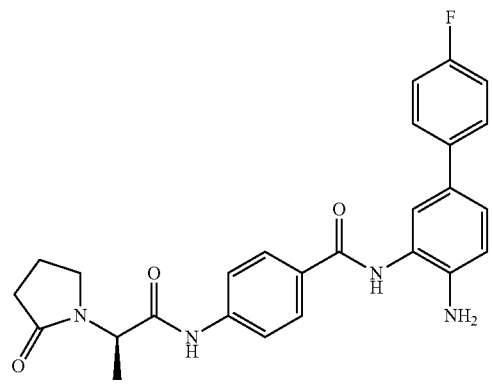

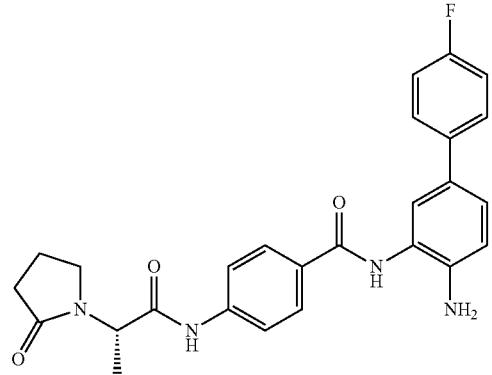

The enantiomers of Example 7 were separated by chiral preparative HPLC using Chiralcel OD-H with Acetonitrile as the mobile phase.

Chiralcel OD-H Retention time: 11.72 min: $C_{26}H_{25}N_4O_3F$ 460.9 (M+1). $^1H$ NMR (400 MHz, DMSO-$d_6$): δ 10.23 (s, 1H); 9.61 (s, 1H); 7.95 (d, J=8.4 Hz, 2H); 7.70 (d, J=8.4 Hz, 2H); 7.56-7.52 (m, 2H); 7.45 (s, 1H); 7.27-7.17 (m, 3H); 6.83 (d, J=8.4 Hz, 1H); 5.04 (s, 2H); 4.70 (q, J=7.2 Hz, 1H); 3.55 (m, 1H); 3.42 (m, 1H); 2.26-2.22 (m, 2H); 1.96-1.91 (m, 2H); 1.36 (d, J=7.2 Hz, 3H).

Chiralcel OD-H Retention time: 9.12 min: $C_{26}H_{25}N_4O_3F$ 460.9 (M+1). $^1H$ NMR (400 MHz, DMSO-$d_6$): δ 10.23 (s, 1H); 9.61 (s, 1H); 7.95 (d, J=8.4 Hz, 2H); 7.70 (d, J=8.4 Hz, 2H); 7.56-7.52 (m, 2H); 7.45 (s, 1H); 7.27-7.17 (m, 3H); 6.83 (d, J=8.4 Hz, 1H); 5.04 (s, 2H); 4.70 (q, J=7.2 Hz, 1H); 3.55 (m, 1H); 3.42 (m, 1H); 2.26-2.22 (m, 2H); 1.96-1.91 (m, 2H); 1.36 (d, J=7.2 Hz, 3H).

Example 35

N-(4-amino-4'-fluorobiphenyl-3-yl)-4-(N-methyl-2-(2-oxopyrrolidin-1-yl)propanamido)benzamide

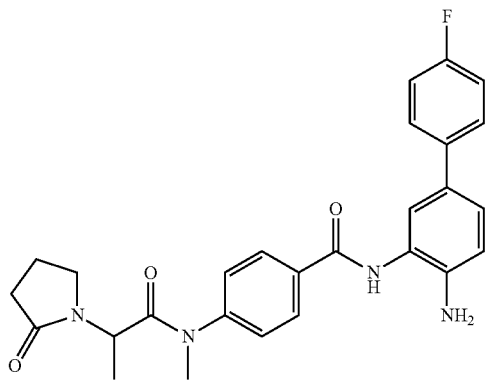

To 2-(2-oxopyrrolidin-1-yl)propanoic acid (942 mgs, 6.0 mmol) in DMF (8 mL), was added HATU (2.4 g, 6.4 mmol), 4-Amino-benzoic acid methyl ester (660 mg, 4.0 mmol) and NMM (1.8 mL, 16.0 mmol) and stirred at 55° C. for 16 hours. The reaction mixture was diluted with ethyl acetate (100 mL) and washed with 1 N HCl, saturated NaHCO$_3$, water, brine and dried over MgSO$_4$. Filtration and concentration gave methyl 4-(N-methyl-2-(2-oxopyrrolidin-1-yl)propanamido)benzoate.

To the crude ester in methanol (6 mL) was added 3 N NaOH (6.5 mL) and stirred at room temperature for 2 hours. The reaction mixture was concentrated, diluted with water and washed twice with ether and the aqueous layer was neutralized with 1N HCl and extracted thrice with ethyl acetate. The combined organic layers were then washed with brine and dried over MgSO$_4$. Filtration and concentration gave the acid which was used for the next step without purification.

To the above acid (325 mg, 1.12 mmol) in DMF (3 mL), was added HATU (639 mg, 1.68 mmol), (3-amino-4'-fluorobiphenyl-4-yl)carbamic acid tert-butyl ester (338 mg, 1.12 mmol) and NMM (0.6 mL, 5.6 mmol) and stirred at 55° C. for 16 hours. The reaction mixture was then diluted with water and acetonitrile and the precipitate was filtered, washed with water and dried. The solid was then purified by column chromatography on silica gel with elution using 60% ethyl acetate/hexanes to give tert-butyl 4'-fluoro-3-(4-(N-methyl-2-(2-oxopyrrolidin-1-yl)propanamido)benzamido)biphenyl-4-ylcarbamate.

To the above BOC protected compound in DCM (4 mL), TFA (0.4 mL) was added and stirred at room temperature for 16 hour. The reaction mixture was then diluted with DCM and washed saturated NaHCO$_3$, water, brine and dried over MgSO$_4$. Filtration and concentration followed by preparative HPLC purification gave the title compound. $C_{27}H_{27}N_4O_3F$ 475.1 (M+1). $^1$H NMR (400 MHz, DMSO-d$_6$): δ 9.72 (s, 1H); 8.01 (d, J=8.0 Hz, 2H); 7.53-7.43 (m, 5H); 7.25-7.14 (m, 3H); 6.81 (d, J=8.4 Hz, 1H); 5.05 (brs, 2H); 4.61 (m, 1H); 3.40 (m, 2H); 3.13 (s, 3H); 2.04 (m, 2H); 1.84-1.79 (m, 2H); 1.08 (d, J=7.2 Hz, 3H).

Example 36

N-(3-amino-6-phenylpyridin-2-yl)-4-(2-(2-oxopyrrolidin-1-yl)propanamido)benzamide

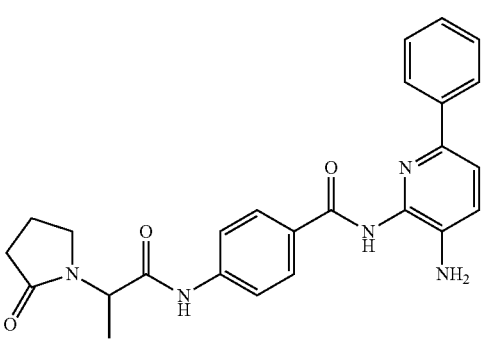

Similar procedure from Example 2 was followed to obtain benzyl 2-(4-(2-(2-oxopyrrolidin-1-yl)propanamido)benzamido)-6-phenylpyridin-3-ylcarbamate using 4-(2-(2-oxopyrrolidin-1-yl)propanamido)benzoic acid and benzyl 2-amino-6-phenylpyridin-3-ylcarbamate. The Cbz group was then deprotected under standard hydrogenation conditions to give the title compound. $C_{25}H_{25}N_5O_3$ 444.0 (M+1). $^1$H NMR (400 MHz, DMSO-d$_6$): δ 10.29 (s, 1H); 10.25 (s, 1H); 8.01 (d, J=8.8 Hz, 2H); 7.92 (d, J=8.8 Hz, 2H); 7.71 (d, J=8.4 Hz, 2H); 7.65 (d, J=8.4 Hz, 1H); 7.38-7.35 (m, 2H); 7.27-7.22 (m, 2H); 5.11 (s, 2H); 4.70 (q, J=7.2 Hz, 1H); 3.55 (m, 1H); 3.44 (m, 1H); 2.26-2.23 (m, 2H); 1.97-1.91 (m, 2H); 1.36 (d, J=7.2 Hz, 3H).

Example 37

Biological Assays

HDAC inhibitory activity of the compound of Example 1 was measured by an assay in which HDAC-1 or -3 were used as a target molecule. The test compound was suspended in and titrated in DMSO. It was then spotted into a 384-well test plate. The enzyme, HDAC-1 or -3, was diluted in assay buffer containing 25 mM Tris-HCl (pH 8.0), 137 mM NaCl, 2.7 mM KCl, and 0.01% Tween-20 and added to the pre-spotted compound. The enzyme/compound mix was incubated at room temperature for 2 hours. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The following table shows IC$_{50}$ data for the compound tested with the protocols described above.

TABLE 1

| | IC$_{50}$ of HDAC inhibitor compound | |
|---|---|---|
| Compound | HDAC-1 inhibitory activity (IC$_{50}$ [μM]) | HDAC-3 inhibitory activity (IC$_{50}$ [μM]) |
| Example 1 | 0.2010 | — |
| Example 2 | 0.0030 | 3.1100 |
| Example 3 | 0.0030 | 2.1000 |
| Example 4 | 0.0915 | 0.2997 |

TABLE 1-continued

| | IC$_{50}$ of HDAC inhibitor compound | |
|---|---|---|
| Compound | HDAC-1 inhibitory activity (IC$_{50}$ [μM]) | HDAC-3 inhibitory activity (IC$_{50}$ [μM]) |
| Example 5 | 0.0016 | 1.0446 |
| Example 6 | 0.0253 | 0.1436 |
| Example 7 | 0.0027 | 1.5377 |
| Example 8 | 0.0028 | 1.3545 |
| Example 9 | 0.0047 | 3.0612 |
| Example 10 | 0.0041 | 3.6257 |
| Example 11 | 0.0019 | 1.0365 |
| Example 12 | 0.0071 | 2.2293 |

The assay results with HDAC-1 and -3 substrates indicate that the compounds have inhibitory activity against HDAC enzymes and thus can be useful to treat or inhibit diseases caused by abnormal activities of HDAC.

All patents and publications cited herein are incorporated by reference into this application in their entirety.

What is claimed is:
1. A compound of Formula (I):

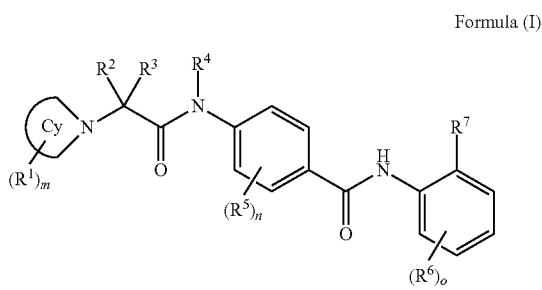

Formula (I)

wherein
Cy is heterocyclyl selected from the group consisting of pyrrolidinyl, piperidinyl, morpholinyl, and piperazinyl;
m is 0, 1 or 2;
$R^1$ is independently selected from the group consisting of hydrogen, cyano, oxo, halo, nitro, hydroxy, alkoxy, amino, alkyl, aryl, cycloalkyl, heterocyclyl and heteroaralkyl;
  wherein the alkyl, aryl, cycloalkyl, heterocyclyl and heteroaralkyl moieties are optionally substituted by alkyl of 1-6 carbon atoms, alkoxy of 1-6 carbon atoms, haloalkyl of 1-6 carbon atoms, and haloalkoxy of 1-6 carbon atoms;
$R^2$ and $R^3$ are independently selected from the group consisting of hydrogen, alkyl, and phenyl;
$R^4$ is selected from the group consisting of hydrogen, alkyl, and cycloalkyl;
$R^5$ is independently selected from the group consisting of hydrogen, halo, and $C_{1-4}$alkyl;
n is 0, 1, or 2;
$R^6$ is independently selected from the group consisting of hydrogen, halo, haloalkyl, aryl, $C_2$-$C_3$alkynylaryl, $C_2$-$C_3$alkynyl-$C_3$-$C_5$cycloalkyl, and heteroaryl, wherein the aryl or heteroaryl is optionally substituted with one or more substituents selected from amino, halo, alkyl, haloalkyl, cycloalkyl, heterocycloalkyl, aryl and heteroaryl;
o is 0, 1, or 2;

$R^7$ is OH or NHZ, where Z is hydrogen, —CH$_2$-alkoxy of 2-4 carbon atoms or —CH$_2$-acetylene of 2-4 carbon atoms;
or a pharmaceutically acceptable salt thereof.
2. The compound of claim 1, wherein $R^2$ and $R^3$ are independently hydrogen, alkyl of 1-4 carbon atoms, or phenyl.
3. The compound of claim 2, wherein $R^7$ is —NHZ, wherein Z is hydrogen, —CH$_2$-alkoxy or —CH$_2$-acetylene.
4. The compound of claim 3, wherein $R^6$ is hydrogen, halo, optionally substituted phenyl, optionally substituted heteroaryl, cyclopropylalkynyl, phenylalkynyl, and o is 1 or 2.
5. The compound of claim 4, wherein $R^4$ is hydrogen or methyl, $R^5$ is hydrogen or halo, and n is 0 or 1.
6. The compound of claim 5, wherein Cy is pyrrolidinyl.
7. The compound of claim 6, chosen from:
N-(2-aminophenyl)-4-(2-(pyrrolidin-1-yl)propanamido)benzamide;
N-(4-amino-4'-fluorobiphenyl-3-yl)-4-(2-(pyrrolidin-1-yl)propanamido)benzamide; and
N-(2-amino-5-(thiophen-2-yl)phenyl)-4-(2-(pyrrolidin-1-yl)propanamido)benzamide.
8. The compound of claim 5, wherein Cy is oxopyrrolidinyl.
9. The compound of claim 8, chosen from:
N-(2-aminophenyl)-4-(2-(2-oxopyrrolidin-1-yl)propanamido)benzamide;
N-(2-amino-5-(thiophen-2-yl)phenyl)-4-(2-(2-oxopyrrolidin-1-yl)propanamido)benzamide;
N-(4-amino-4'-fluorobiphenyl-3-yl)-4-(2-(2-oxopyrrolidin-1-yl)propanamido)benzamide;
N-(2-amino-5-(thiophen-2-yl)phenyl)-3-fluoro-4-(2-(2-oxopyrrolidin-1-yl)propanamido)benzamide;
N-(2-amino-5-(5-chlorothiophen-2-yl)phenyl)-4-(2-(2-oxopyrrolidin-1-yl)propanamido)benzamide;
N-(4-amino-4'-fluorobiphenyl-3-yl)-3-fluoro-4-(2-(2-oxopyrrolidin-1-yl)propanamido)benzamide;
N-(4-amino-4',6-difluorobiphenyl-3-yl)-4-(2-(2-oxopyrrolidin-1-yl)propanamido)benzamide;
N-(2-amino-5-fluorophenyl)-4-(2-(2-oxopyrrolidin-1-yl)propanamido)benzamide;
N-(2-amino-4,6-difluorophenyl)-4-(2-(2-oxopyrrolidin-1-yl)propanamido)benzamide;
N-(4-amino-4'-fluorobiphenyl-3-yl)-4-(2-(2-oxopyrrolidin-1-yl)acetamido)benzamide;
N-(4-amino-4'-fluorobiphenyl-3-yl)-4-(2-methyl-2-(2-oxopyrrolidin-1-yl)propanamido)benzamide;
N-(2-amino-5-(cyclopropylethynyl)phenyl)-4-(2-(2-oxopyrrolidin-1-yl)propanamido)benzamide;
N-(2-amino-5-(phenylethynyl)phenyl)-4-(2-(2-oxopyrrolidin-1-yl)propanamido)benzamide;
(S)-N-(2-aminophenyl)-4-(3,3-dimethyl-2-(2-oxopyrrolidin-1-yl)butanamido)benzamide;
(S)-N-(4-amino-4'-fluorobiphenyl-3-yl)-4-(3,3-dimethyl-2-(2-oxopyrrolidin-1-yl)butanamido)benzamide;
N-(4'-fluoro-4-(prop-2-ynylamino)biphenyl-3-yl)-4-(2-(2-oxopyrrolidin-1-yl)propanamido)benzamide;
N-(4'-fluoro-4-(2-methoxyethylamino)biphenyl-3-yl)-4-(2-(2-oxopyrrolidin-1-yl)propanamido)benzamide;
N-(4-amino-4'-fluorobiphenyl-3 -yl)-3-(2-(2-oxopyrrolidin-1-yl)propanamido)benzamide;
N-(4-amino-4'-fluorobiphenyl-3-yl)-4-(N-methyl-2-(2-oxopyrrolidin-1-yl)propanamido)benzamide;
(R)-N-(4-amino-4'-fluorobiphenyl-3-yl)-4-(2-(2-oxopyrrolidin-1-yl)propanamido)benzamide;
(S)-N-(4-amino-4'-fluorobiphenyl-3-yl)-4-(2-(2-oxopyrrolidin-1-yl)propanamido)benzamide; and N-(3-amino-6-phenylpyridin-2-yl)-4-(2-(2-oxopyrrolidin-1-yl)propanamido)benzamide.

10. The compound of claim 5, wherein Cy is morpholinyl.
11. The compound of claim 10, chosen from:
N-(2-aminophenyl)-4-(2-morpholino-2-phenylacetamido)benzamide;
N-(2-amino-5-(thiophen-2-yl)phenyl)-4-(2-morpholinopropanamido)benzamide
N-(4-amino-4'-fluorobiphenyl-3-yl)-4-(2-morpholinopropanamido)benzamide;
N-(4-amino-4'-fluorobiphenyl-3-yl)-4-(2-methyl-2-morpholinopropanamido)benzamide; and
N-(4-amino-4'-fluorobiphenyl-3-yl)-4-(2-morpholinoacetamido)benzamide.
12. The compound of claim 5, wherein Cy is piperazinyl.
13. The compound of claim 12, chosen from:
N-(2-aminophenyl)-4-(2-(4-(5-(trifluoromethyl)pyridin-2-yl)piperazin-1-yl)propanamido)benzamide;
N-(4-amino-4'-fluorobiphenyl-3-yl)-4-(2-methyl-2-(piperazin-1-yl)propanamido)benzamide;
N-(4-amino-4'-fluorobiphenyl-3-yl)-4-(2-(4-(5-(trifluoromethyl)pyridin-2-yl)piperazin-1-yl)propanamido)benzamide;
N-(2-aminophenyl)-4-(2-methyl-2-(4-(5-(trifluoromethyl)pyridin-2-yl)piperazin-1-yl)propanamido)benzamide;
N-(4-amino-4'-fluorobiphenyl-3-yl)-4-(2-(4-cyclopropylpiperazin-1-yl)-2-methylpropanamido)benzamide; and
N-(4-amino-4'-fluorobiphenyl-3-yl)-4-(2-(4-ethylpiperazin-1-yl)acetamido)benzamide.
14. The compound of claim 5, wherein Cy is oxopiperidinyl, namely N-(4-amino-4'-fluorobiphenyl-3-yl)-4-(2-(2-oxopiperidin-1-yl)acetamido)benzamide.
15. A pharmaceutical composition comprising a pharmaceutically effective amount of one or more compounds according to claim 1 and a pharmaceutically-acceptable carrier.
16. The pharmaceutical composition according to claim 15, further comprising one or more anti-cancer agents.
17. The pharmaceutical composition according to claim 16, wherein the one or more anti-cancer agents are selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

* * * * *